United States Patent
Hermkens et al.

(10) Patent No.: US 8,124,647 B2
(45) Date of Patent: Feb. 28, 2012

(54) NON-STEROIDAL ANDROGENS COMPOUNDS

(75) Inventors: Pedro Harold Han Hermkens, Oss (NL); Herman Thijs Stock, Oss (NL); Jaap Van Der Louw, Oss (NL); Neeltje Miranda Teerhuis, Oss (NL); Johannes Petrus Maria Lommerse, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 12/875,295

(22) Filed: Sep. 3, 2010

(65) Prior Publication Data

US 2011/0065768 A1  Mar. 17, 2011

Related U.S. Application Data

(62) Division of application No. 10/534,945, filed as application No. PCT/EP03/050783 on Nov. 3, 2003, now Pat. No. 7,795,280.

(60) Provisional application No. 60/424,579, filed on Nov. 7, 2002.

(30) Foreign Application Priority Data

Nov. 7, 2002 (EP) .................................. 02079648

(51) Int. Cl.
*A61K 31/404* (2006.01)
*C07D 209/30* (2006.01)

(52) U.S. Cl. ........................................ 514/418; 548/484

(58) Field of Classification Search ................... 548/484; 514/418
See application file for complete search history.

(56) References Cited

U.S. PATENT DOCUMENTS 5,767,139 A * 6/1998 Maw et al. ..................... 514/381

* cited by examiner

*Primary Examiner* — Patricia Morris
(74) *Attorney, Agent, or Firm* — Janet E. Fair; John C. Todaro

(57) ABSTRACT

This invention provides non-steroidal compounds with affinity for the androgen receptor and utility for androgen-receptor related treatments, having a structure according to the formula

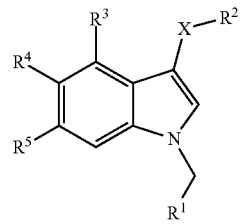

or a salt or hydrate form thereof.

18 Claims, No Drawings

NON-STEROIDAL ANDROGENS COMPOUNDS

RELATED APPLICATIONS

This application is a divisional of U.S. application Ser. No. 10/534,945 filed on May 6, 2005, now U.S. Pat. No. 7,795,280 which is a national stage entry under 35 U.S.C. §371 of PCT/EP2003/050783 filed on Nov. 3, 2003 which claims priority to U.S. Application No. 60/424,579 filed on Nov. 7, 2002.

The invention relates to indole derivatives, their preparation and their use for the treatment of androgen-receptor related conditions, disorders or diseases and other androgen related treatments.

Compounds possessing androgenic activity are useful in the treatment of men with low endogenous levels of circulating androgenic hormones or men with suppressed androgenic effects. Such treatments are prescribed to older men, to hypogonadal men or men treated with progestagens for male contraception. In addition, potent androgens suppress spermatogenesis and can be used as male contraceptives.

It is thus important to obtain compounds with high affinity for the androgen receptor. Non-steroidal compounds with high affinity for the androgen receptor are particularly useful since they may have different tissue distribution characteristics than steroidal androgens and can be designed by proper choice of substituents to be more or less selective for certain tissues. For example, an action in the brain is usually prevented when compounds are strongly hydrophilic or carry an ionic charge.

The subject invention provides non-steroidal compounds with affinity for the androgen receptor. These compounds are potentially useful for the treatment of androgen-receptor related disorders or disorders which can be treated with androgens. The compounds of the subject invention have a structure according to formula I:

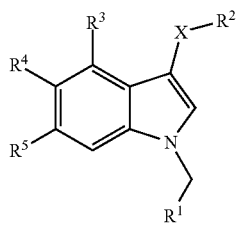

wherein

X is S, SO or $SO_2$;

$R^1$ is a 5- or 6-membered monocyclic, hetero- or homocyclic, saturated or unsaturated ring structure optionally substituted with one or more substituents selected from the group consisting of halogen, CN, (1C-4C)fluoroalkyl, nitro, (1C-4C)alkyl, (1C-4C)alkoxy or (1C-4C)fluoroalkoxy;

$R^2$ is 2-nitrophenyl, 2-cyanophenyl, 2-hydroxymethyl-phenyl, pyridin-2-yl, pyridin-2-yl-N-oxide, 2-benzamide, 2-benzoic acid methyl ester or 2-methoxyphenyl;

$R^3$ is H, halogen or (1C-4C)alkyl;

$R^4$ is H, OH, (1C-4C)alkoxy, or halogen;

$R^5$ is H, OH, (1C-4C)alkoxy, $NH_2$, CN, halogen, (1C-4C)fluoroalkyl, $NO_2$, hydroxy(1C-4C)alkyl, $CO_2H$, $CO_2$(1C-6C)alkyl, or $R^5$ is $NHR^6$, wherein $R^6$ is (1C-6C)acyl optionally substituted with one or more halogens, $S(O)_2$(1C-4C)alkyl, or $S(O)_2$aryl optionally substituted with (1C-4C)alkyl or one or more halogens, or $R^5$ is $C(O)N(R^8,R^9)$, wherein $R^8$ and $R^9$ each independently are H, (3C-6C)cycloalkyl, or $CH_2R^{10}$, wherein $R^{10}$ is H, (1C-5C)alkyl, (1C-5C)alkenyl, hydroxy(1C-3C)alkyl, (1C-4C)alkylester of carboxy(1C-4C)alkyl, (1C-3C)alkoxy(1C-3C)alkyl, (mono- or di(1C-4C) alkyl)aminomethyl, (mono- or di(1C-4C)alkyl)aminocarbonyl, or a 3-, 4-, 5- or 6-membered monocyclic, homo- or heterocyclic, aromatic or non-aromatic ring, or $R^8$ and $R^9$ form together with the N a heterocyclic 5- or 6-membered saturated or unsaturated ring optionally substituted with (1C-4C)alkyl;

or a salt or hydrate form thereof.

In one embodiment $R^1$ is a 5- or 6-membered monocyclic, hetero- or homocyclic, saturated or unsaturated ring structure optionally substituted with one or more substituents selected from the group consisting of halogen, CN, $CF_3$, nitro, methoxy, trifluoromethoxy or methyl; $R^2$ is 2-nitrophenyl, 2-cyanophenyl, 2-hydroxymethyl-phenyl, pyridin-2-yl, pyridin-2-yl-N-oxide, 2-benzamide, 2-benzoic acid methyl ester or 2-methoxyphenyl; $R^3$ is H, halogen or (1C-2C)alkyl; $R^4$ is H or F.

In another embodiment $R^5$ is H, OH, (1C-4C)alkoxy, CN, halogen, (1C-4C)fluoroalkyl, $NO_2$, hydroxy(1C-4C)alkyl, $CO_2$(1C-6C)alkyl, or $R^5$ is $NHR^6$, wherein $R^6$ is (1C-6C)acyl optionally substituted with one or more halogens, $S(O)_2$(1C-4C)alkyl, or $S(O)_2$aryl optionally substituted with (1C-4C)alkyl or one or more halogens, or $R^5$ is $C(O)N(R^8,R^9)$, wherein $R^8$ and $R^9$ each independently are H, (3C-6C)cycloalkyl, or $CH_2R^{10}$, wherein $R^{10}$ is H, (1C-5C)alkyl, (1C-5C)alkenyl, hydroxy(1C-3C)alkyl, (1C-4C)alkylester of carboxy(1C-4C)alkyl, (1C-3C)alkoxy (1C-3C)alkyl, (mono- or di(1C-4C)alkyl)aminomethyl, (mono- or di(1C-4C)alkyl)-aminocarbonyl, or a 3-, 4-, 5- or 6-membered monocyclic, homo- or heterocyclic, aromatic or non-aromatic ring, or $R^8$ and $R^9$ form together with the N a heterocyclic 5- or 6-membered saturated or unsaturated ring optionally substituted with (1C-4C)alkyl.

In yet another embodiment $R^3$ is H or halogen; $R^4$ is H; $R^5$ is H, OH, (1C-4C)alkoxy, CN, F, Cl, $CF_3$, $NO_2$, hydroxy(1C-4C)alkyl, $CO_2$(1C-6C)alkyl, or $R^5$ is $NHR^6$, wherein $R^6$ is (1C-3C)acyl optionally substituted with one or more halogens or $R^5$ is $C(O)N(R^8,R^9)$, wherein $R^8$ and $R^9$ each independently are H, (3C-5C)cycloalkyl, or $CH_2R^{10}$, wherein $R^{10}$ is H, (1C-5C)alkyl, (1C-5C)alkenyl, hydroxy(1C-3C)alkyl, (1C-2C)alkylester of carboxy(1C-2C)alkyl, (1C-3C)alkoxy (1C-3C)alkyl, (mono- or di(1C-4C)alkyl)aminomethyl, (mono- or di(1C-4C)alkyl)aminocarbonyl, (3C-5C)cycloalkyl, or a 5-membered heterocyclic ring.

In yet another embodiment X is S or $SO_2$; $R^2$ is 2-nitrophenyl, 2-hydroxymethyl-phenyl, 2-benzamide, 2-methoxyphenyl, 2-cyanophenyl or pyridin-2-yl; $R^3$ is H or F; $R^5$ is H, OH, (1C-2C)alkoxy, CN, F, Cl, $CF_3$, $NO_2$, hydroxy(1C-4C)alkyl, $CO_2$(1C-4C)alkyl, or $R^5$ is $NHR^6$, wherein $R^6$ is formyl, acetyl, fluoroacetyl, difluoroacetyl, or trifluoroacetyl, or $R^5$ is $C(O)N(R^8,R^9)$, wherein $R^8$ is H, and $R^9$ is H, cyclopropyl or $R^9$ is $CH_2R^{10}$, wherein $R^{10}$ is H, (1C-2C)alkyl, hydroxy(1C-2C)alkyl, methoxy(1C-2C)alkyl, cyclopropyl.

In yet another embodiment X is S; $R^1$ is 3,5-difluorophenyl, pyridin-2-yl, pyridin-3-yl, pyrimidin-5-yl, pyrazin-4-yl, pyrazin-2-yl, 3-fluorophenyl, 3-cyanophenyl, or 3-nitrophenyl; $R^2$ is 2-nitrophenyl, 2-hydroxymethyl-phenyl, 2-methoxyphenyl, 2-cyanophenyl or pyridin-2-yl; $R^3$ is H; $R^5$ is OH, (1C-2C)alkoxy, CN, $CF_3$, $NO_2$, hydroxy(1C-4C)alkyl, $CO_2$(1C-4C)alkyl, or $NHR^6$, wherein $R^6$ is formyl, acetyl, fluoroacetyl, difluoroacetyl, or trifluoroacetyl.

In yet another embodiment $R^1$ is 3,5-difluorophenyl, pyridin-2-yl, pyridin-3-yl, pyrimidin-5-yl, pyrimidin-4-yl, or pyrazin-2-yl; $R^2$ is 2-nitrophenyl, or 2-hydroxymethyl-phenyl; $R^5$ is OH, (1C-2C)alkoxy, CN, hydroxy(1C-4C)alkyl, or NHR$^6$, wherein $R^6$ is formyl, acetyl, fluoroacetyl, difluoroacetyl, or trifluoroacetyl.

In yet another embodiment $R^1$ is 3,5-difluorophenyl, pyridin-2-yl, pyridin-3-yl, pyrimidin-5-yl, or pyrimidin-4-yl; $R^2$ is 2-nitrophenyl; $R^5$ is OH, (1C-2C)alkoxy, CN, or NHR$^6$, wherein $R^6$ is formyl, acetyl, fluoroacetyl, difluoroacetyl, or trifluoroacetyl.

In a specific embodiment the subject invention provides the compounds 6-Methoxy-3-(2-nitro-phenylsulfanyl)-1-pyrimidin-5-ylmethyl-1H-indole, 3-(2-Nitro-phenylsulfanyl)-1-pyridin-2-ylmethyl-1H-indole-6-carbonitrile, 3-(2-Nitro-phenylsulfanyl)-1-pyridin-2-ylmethyl-1H-indole-6-carbonitrile-hydrochloride, 3-(2-Nitro-phenylsulfanyl)-1-pyrimidin-5-ylmethyl-1H-indole-6-carbonitrile, 3-(2-Nitro-phenylsulfanyl)-1-pyrimidin-4-ylmethyl-1H-indole-6-carbonitrile, N-[1-(3,5-Difluoro-benzyl)-3-(2-nitro-phenylsulfanyl)-1H-indol-6-yl]-2-fluoro-acetamide, and N-[3-(2-Nitro-phenylsulfanyl)-1-pyrimidin-5-ylmethyl-1H-indol-6-yl]-formamide.

In another embodiment X is S; $R^1$ is 3,5-difluorophenyl, pyridin-2-yl, pyridin-3-yl, 3-fluorophenyl, 3-cyanophenyl, or 3-nitrophenyl; $R^2$ is 2-nitrophenyl, 2-hydroxymethyl-phenyl, 2-methoxyphenyl, 2-cyanophenyl or pyridin-2-yl; $R^3$ is H; $R^5$ is C(O)N($R^8$,$R^9$), wherein $R^8$ is H, and $R^9$ is H, or CH$_2$R$^{10}$, wherein $R^{10}$ is H, (1C-2C)alkyl, hydroxy(1C-2C)alkyl, or methoxy(1C-2C)alkyl.

In yet another embodiment $R^1$ is 3,5-difluorophenyl, pyridin-2-yl, or pyridin-3-yl; $R^2$ is 2-nitrophenyl, or 2-hydroxymethyl-phenyl; $R^5$ is C(O)N($R^8$,$R^9$), wherein $R^8$ is H, and $R^9$ is CH$_2$R$^{10}$, wherein $R^{10}$ is H, or (1C-2C)alkyl.

In a specific embodiment the subject invention provides the compound 1-(3,5-Difluoro-benzyl)-3-(2-nitro-phenylsulfanyl)-1H-indole-6-carboxylic acid methylamide.

In yet another embodiment X is S; $R^1$ is 3,5-difluorophenyl, pyridin-2-yl, pyridin-3-yl, 3-fluorophenyl, 3-cyanophenyl, or 3-nitrophenyl; $R^2$ is 2-nitrophenyl, 2-hydroxymethyl-phenyl, 2-methoxyphenyl, 2-cyanophenyl or pyridin-2-yl; $R^3$ is H; $R^5$ is C(O)N($R^8$,$R^9$), wherein $R^8$ and $R^9$ each independently are H or CH$_2$R$^{10}$, wherein $R^{10}$ is H, (1C-5C)alkyl, (1C-5C)alkenyl, hydroxy(1C-3C)alkyl, (1C-3C)alkoxy(1C-3C)alkyl, or (mono- or di(1C-4C)alkyl)aminomethyl.

In yet another embodiment $R^1$ is 3,5-difluorophenyl, pyridin-2-yl, or pyridin-3-yl; $R^2$ is 2-nitrophenyl, or 2-hydroxymethyl-phenyl; $R^5$ is C(O)N($R^8$,$R^9$), wherein $R^8$ and $R^9$ each independently are H, or CH$_2$R$^{10}$, wherein $R^{10}$ is H, (1C-5C)alkyl, hydroxy(1C-3C)alkyl, or (1C-3C)alkoxy(1C-3C)alkyl.

In a specific embodiment the subject invention provides the compound 1-(3,5-Difluoro-benzyl)-3-(2-nitro-phenylsulfanyl)-1H-indole-6-carboxylic acid dimethylamide.

In those cases that a compound of the invention contains a basic amine function, the compound may be used as a free base or as a pharmaceutically acceptable salt such as hydrochloride, acetate, oxalate, tartrate, citrate, phosphate, maleate or fumarate.

A compound according to the invention is a compound as defined above, a salt thereof, a hydrate thereof or a prodrug thereof.

The terms used in this description have the following meaning:

alkyl is a branched or unbranched alkyl group, for example methyl, ethyl, propyl, isopropyl, butyl, sec-butyl, tert-butyl, hexyl, and the like;
   fluoroalkyl is an alkyl group substituted with one or more fluorine atoms;
   cycloalkyl is a cyclized unbranched alkyl group, such as cyclopropyl, cyclobutyl, cyclopentyl and the like;
   alkenyl is a branched or unbranched alkenyl group, such as ethenyl, 2-butenyl, etc.;
   alkoxy is a branched or unbranched alkyloxy group, for example methyloxy, ethyloxy, propyloxy, isopropyloxy, butyloxy, sec-butyloxy, tert-butyloxy and the like;
   fluoroalkoxy is a alkoxy group substituted with one or more fluorine atoms;
   aryl is a mono- or polycyclic, homo- or heterocyclic aromatic ring system, such as phenyl, naphtyl or pyridyl; a monocyclic ring with 6 atoms is preferred for use;
   acyl is a (substituent-)carbonyl group, such as an aroyl or alkanoyl;
   aroyl is arylcarbonyl such as a benzoyl group;
   alkanoyl means a formyl or alkylcarbonyl group such as formyl, acetyl and propanoyl;
   carboxy is a —COOH substituent, making the compound an organic acid;
   carboxylate is a salt of a carboxyl substituent.

The prefixes (1C-4C), (2C-4C) etc. have the usual meaning to restrict the meaning of the indicated group to those with 1 to 4, 2 to 4 etc. carbon atoms;

halogen refers to fluorine, chlorine, bromine and iodine.

The androgen receptor affinity and efficacy of the compounds according to the invention make them suitable for use in the treatment of androgen-receptor related disorders, disorders which can be treated with androgens, and in diagnostic methods focussed on the amount and/or location of androgen receptors in various tissues. For the latter purpose it can be preferred to make labelled variants of the compounds according to the invention. Typical androgen receptor-related treatments are those for male contraception and male or female hormone replacement therapy. Thus the invention also pertains to a method of treatment of androgen insufficiency, by administering to a male or female human or animal an effective amount of any of the compounds of the subject invention. The subject invention also lies in the use of any of its compounds for the preparation of a medicine for treating androgen insufficiency. In the context of the invention, the term "androgen insufficiency" is to be understood to pertain to all kinds of diseases, disorders, and symptoms in which a male or a female suffers from too low a testosterone level, such as in hypogonadal men or boys. In particular, the androgen insufficiency to be treated by a compound of the invention is the reduction of the testosterone level which a male individual incurs as a result of age (the compound of the invention is then used for male hormone replacement therapy), or when he is subject to male contraception. In the context of male contraception, the compound of the invention especially serves to neutralize the effect of regimens of male hormone contraception in which a sterilitant such as a progestagen or LHRH (luteinizing hormone releasing hormone) is administered regularly, e.g. daily, or it is used as the sole male contraceptive substance.

Thus, the subject invention provides any one of the compounds of the subject invention for use in therapy.

The subject invention further encompasses a pharmaceutical composition comprising a compound of the subject invention and a pharmaceutically acceptable carrier. In an embodiment of the subject invention, the pharmaceutical composition is for the treatment of a disorder selected from the group consisting of an androgen-receptor related disorder, an androgen related disorder and androgen insufficiency.

The subject invention further provides a use of a compound of the invention for the manufacture of a medicament for the treatment of androgen-receptor related disorders, androgen related disorders and androgen insufficiency.

The subject invention further envisions a method of treating a disorder selected from the group consisting of an androgen-receptor related disorder, an androgen related disorder and androgen insufficiency comprising administering a pharmaceutically effective amount of a compound according to the invention to a subject in need thereof.

The compounds of the invention may further be useful for the treatment of osteoporosis, as well as other bone disorders, bone fraction repair, sarcopenia, frailty, skin aging, male hypogonadism, female sexual dysfunction, postmenopausal symptoms, atherosclerosis, aplastic anemia, muscular atrophy, lipodystrophy, reduced muscle strength and function, side effects of chemotherapy, chronic fatigue syndrome, benign prostate hyperplasia (BPH), cachexia, chronic catabolic state, cognitive impairment, male contraception, and others.

The compounds of the invention may be administered in conjunction with estrogens, progestogen and other androgens.

The compounds of the invention can be produced by various methods known in the art of organic chemistry in general. More specifically the routes of synthesis as illustrated in the following schemes and examples can be used. In the schemes and examples the following abbreviations were used:

DMF=dimethylformamide
mCPBA=meta chloro perbenzoic acid
THF=tetrahydrofuran
TBTU=2-(1H-benzotriazol-1-yl)-1,1,3,3-tetramethyluronium tetrafluoroborate
DIPEA=diisopropylethylamine
EDCI=1-(3-dimethylaminopropyl)-3-ethylcarbodiimide hydrochloride
HOBt=1-hydroxybenzotriazole
NMM=N-methylmorpholine
SPE=solid phase extraction
RP-SPE=reversed phase solid phase extraction
DMSO=dimethylsulfoxide
DCM=dichloromethane
DHT=5α-dihydrotestosterone
NMP=1-methyl-2-pyrrolidinone
DMS=dimethyl sulfide With regard to nomenclature the following trivial names are used interchangeably for substituents $R^1$ and $R^2$:

| Trivial name | Official name |
| --- | --- |
| 2-pyridyl | pyridin-2-yl |
| 3-pyridyl | pyridyl-3-yl |
| 4-pyridyl | pyridyl-4-yl |
| 3,5-pyrimidyl | pyrimidin-5-yl |
| 2,4-pyrimidyl | pyrimidin-4-yl |
| 2,5-pyrazyl | pyrazin-2-yl |
| etc. | |

In each of the Schemes I-VII the meanings of the symbols correspond to the definitions given in the previous paragraphs.

Substituted indole compounds of structure 3 were prepared in two steps from the correctly substituted indoles of structure 1, via two different routes. In the first route a correctly substituted indole of structure 1 is N-alkylated with a halide of type $R^1CH_2Y$, where Y is a halogen, mesylate or tosylate, with NaH or $Cs_2CO_3$ as a base in DMF or NMP at 0° C. to room temperature, to give a compound of structure 2. Structure 2 is then sulfonylated at the C-3 position of the indole ring by reaction with a sulfenyl chloride in either $CH_2Cl_2$ or diethyl ether at room temperature, to give structure 3. In the second route the two steps of the first route are reversed: the correctly substituted indole of structure 1 is first sulfonylated at the C-3 position of the indole to give structure 4, followed by N-alkylation with $R^1CH_2Y$ to give structure 3 (Scheme I).

Scheme I

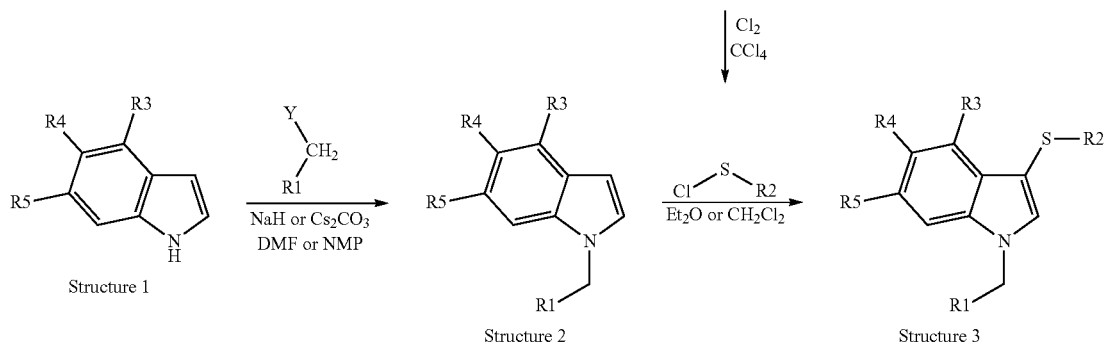

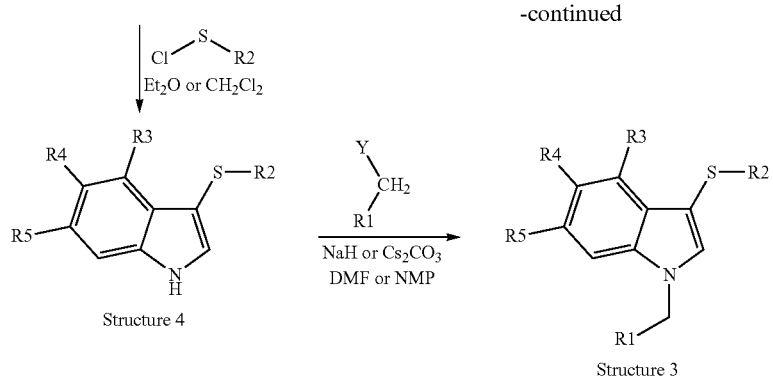

Sulfoxides of structure 5 can be obtained by oxidation of the corresponding sulfide (Structure 3) by reaction with e.g. 0.9 equivalents of mCPBA. Sulfones of structure 6 can be obtained by oxidation of the corresponding sulfide (Structure 3) by reaction with e.g. 3 equivalents of mCPBA (Scheme II).

Scheme II

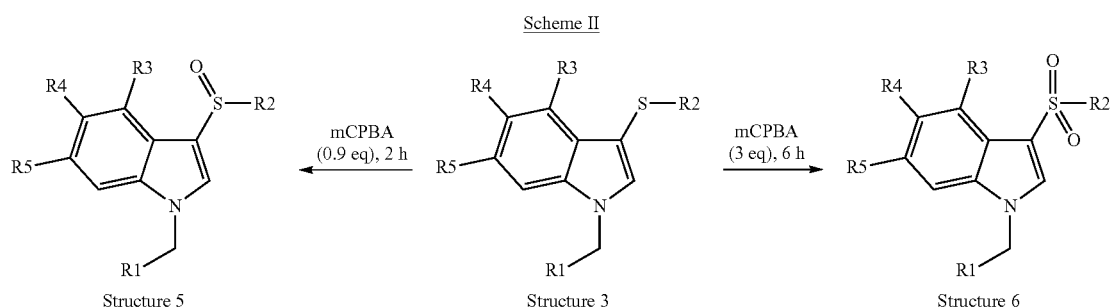

Scheme III describes the synthesis of compounds of structure 3, in which the $R^2$ group is a phenyl ring substituted on the 2-position with either $CO_2Me$ (Structure 7), $CH_2OH$ (Structure 8), $CO_2H$ (Structure 9), CONHMe (Structure 10), $CONH_2$ (Structure 11) or CN (Structure 12).

Scheme III

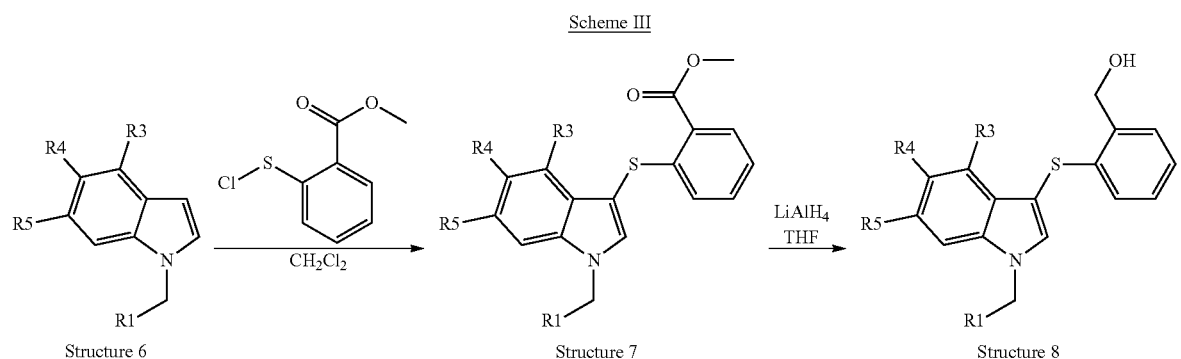

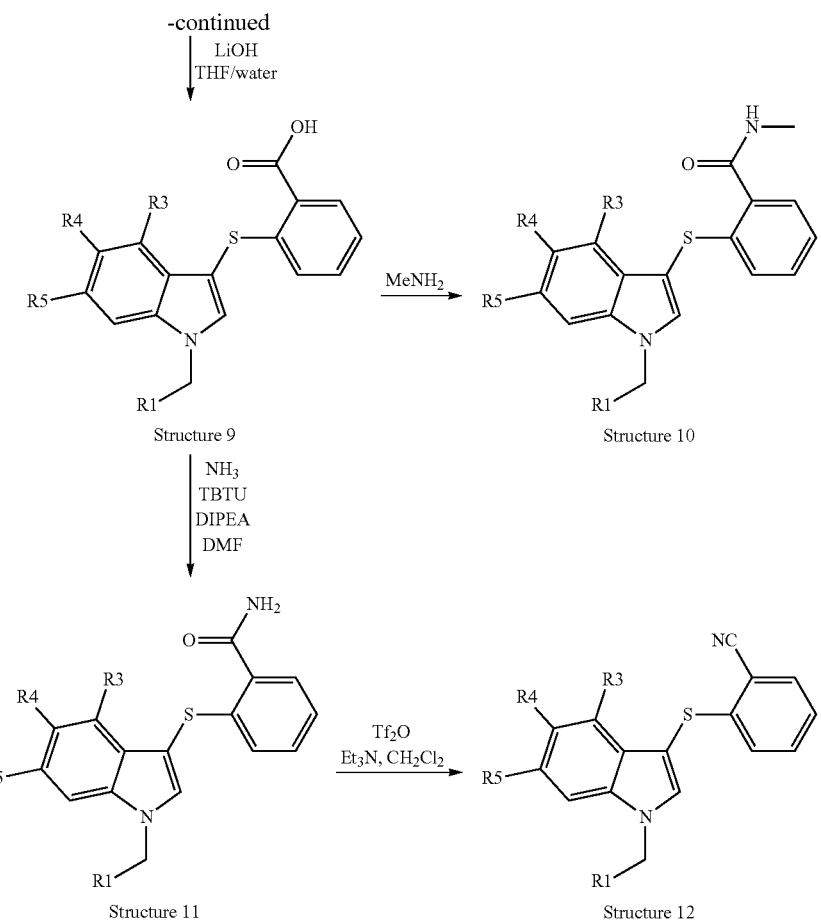

In the first step a substituted indole of structure 6 is sulfonylated at the 3-position with 2-(carboxymethyl)-phenylsulfenyl chloride, which was prepared from methylthiosalicylate and chlorine gas, to give a compound of structure 7. Reduction of the methyl ester moiety of compounds of structure 7 with LiAlH$_4$ gave the corresponding hydroxymethyl compounds of structure 8. Saponification of the methyl ester moiety of compounds of structure 7 with lithium hydroxide gave the corresponding carboxylic acid compounds of structure 9. The carboxylic acid moiety of compounds of structure 9 can be converted to the corresponding carboxamide by reaction with an amine, TBTU and DIPEA in DMF at room temperature. By this method structure 10 was obtained when methylamine was used as the amine and structure 11 was obtained when NH$_3$ was used as the amine. Dehydration of the benzamide moiety of structure 11 with Tf$_2$O and triethylamine in CH$_2$Cl$_2$ afforded the corresponding benzonitrile compound of structure 12 (Scheme III).

-continued

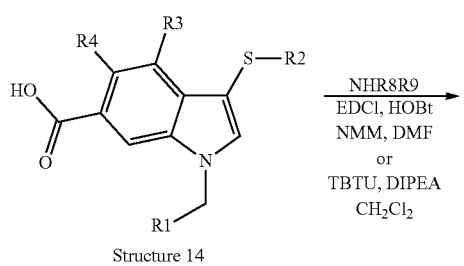

Scheme IV

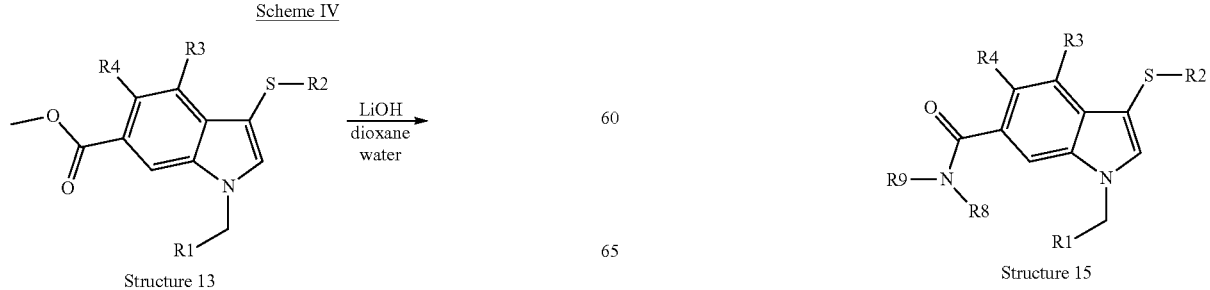

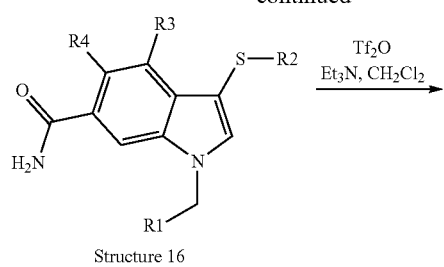

Structure 16

CONR⁸R⁹ (Structure 15), CONH$_2$ (Structure 16) or CN (Structure 17). Saponification of the methyl ester moiety of structure 13 with lithium hydroxide afforded the corresponding carboxylic acid of structure 14. The carboxylic acid moiety of structure 14 can be converted to the corresponding carboxamides of structures 15 and 16 by reaction with an amine or amine salt, in the presence of EDCI and HOBt in a mixture of NMM and DMF or in the presence of TBTU and DIPEA in CH$_2$Cl$_2$ at room temperature. Dehydration of the benzamide moiety of structure 16 with Tf$_2$O and triethylamine in CH$_2$Cl$_2$ afforded the corresponding benzonitrile compound of structure 17 (Scheme IV).

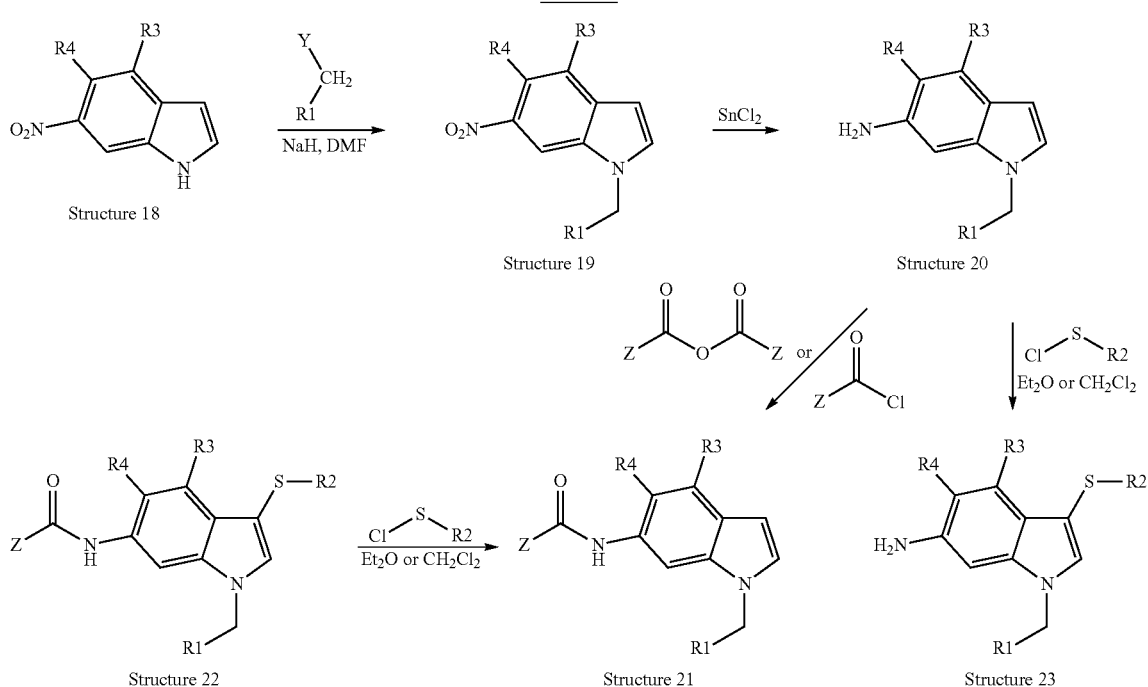

Scheme V

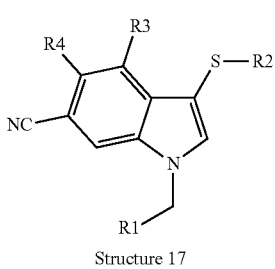

Structure 17

Scheme IV describes the synthesis of compounds of structure 3, in which the indole ring is substituted at the 6-position with either CO$_2$Me (Structure 13), CO$_2$H (Structure 14), Scheme V describes the synthesis of compounds of structure 22 containing an acylated amine functionality on the 6-position of the indole ring. These compounds can be synthesised from 6-nitro indoles of structure 18 in 4 steps. In the first step the indole of structure 18 is alkylated on the nitrogen atom by reaction of a halide of type R¹CH$_2$Y, in which Y is halogen, mesylate or tosylate, with NaH as a base in DMF to give compounds of structure 19. In the second step the nitro group of structure 19 is reduced to an amine group by SnCl$_2$ to give structure 20. Subsequent acylation of the amine group with an acid chloride of type ZCOCl afforded structure 21, which was then sulfonylated at the 3-position of the indole ring by reaction with a sulfenyl chloride in either CH$_2$Cl$_2$ or Et$_2$O as a solvent, at room temperature, to give compounds of structure 22. Direct sulfonylation of a compound of structure 20 with a sulfenyl chloride afforded structure 23

In Scheme VI is described how methyl ethers of structure 24 can be cleaved with e.g. BF$_3$.DMS in THF at room temperature to hydroxy compounds of structure 25.

Scheme VI

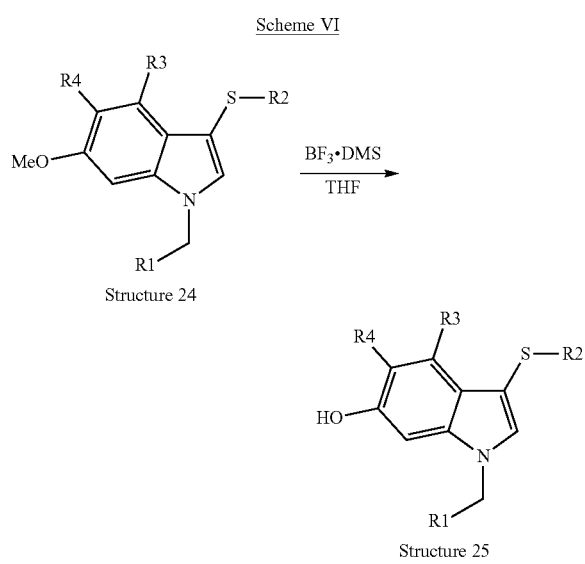

Scheme VII describes the synthesis of compounds containing either an acylated amine functionality (structure 28) or a sulfonamide functionality (structure 29) at the 6-position of the indole ring. These compounds can be prepared from 6-nitro indoles of structure 18 in 6 steps. In the first step the indole of structure 18 is alkylated on N–1 by reaction of a halide of type $R^1CH_2Y$, in which Y is a halogen, mesylate or tosylate, with NaH or $Cs_2CO_3$ as a base in either NMP or DMF to give compounds of structure 19. In the second step the nitro group of structure 19 is reduced to an amine group with Fe and $NH_4Cl$ in an ethanol/water mixture to give structure 20. Subsequent acylation of the amine group with di-tert-butyl dicarbonate afforded structure 26 which was then sulfonylated at the 3-position of the indole ring by reaction with a sulfenyl chloride in either $CH_2Cl_2$ or $Et_2O$ to give compounds of structure 27. Then the amide functionality at the 6-position of the indole was cleaved with trifluoroacetic acid or HCOOH to give amines of structure 23. These amines can be converted into amides of structure 28 by reaction with either triethylamine and an acid chloride in $CH_2Cl_2$ (method a) or an acid, TBTU and DIPEA in $CH_2Cl_2$ (method b). Sulfonamides of structure 29 can be prepared by reaction of amines of structure 23 with sulfonyl chlorides (method c).

Scheme VII

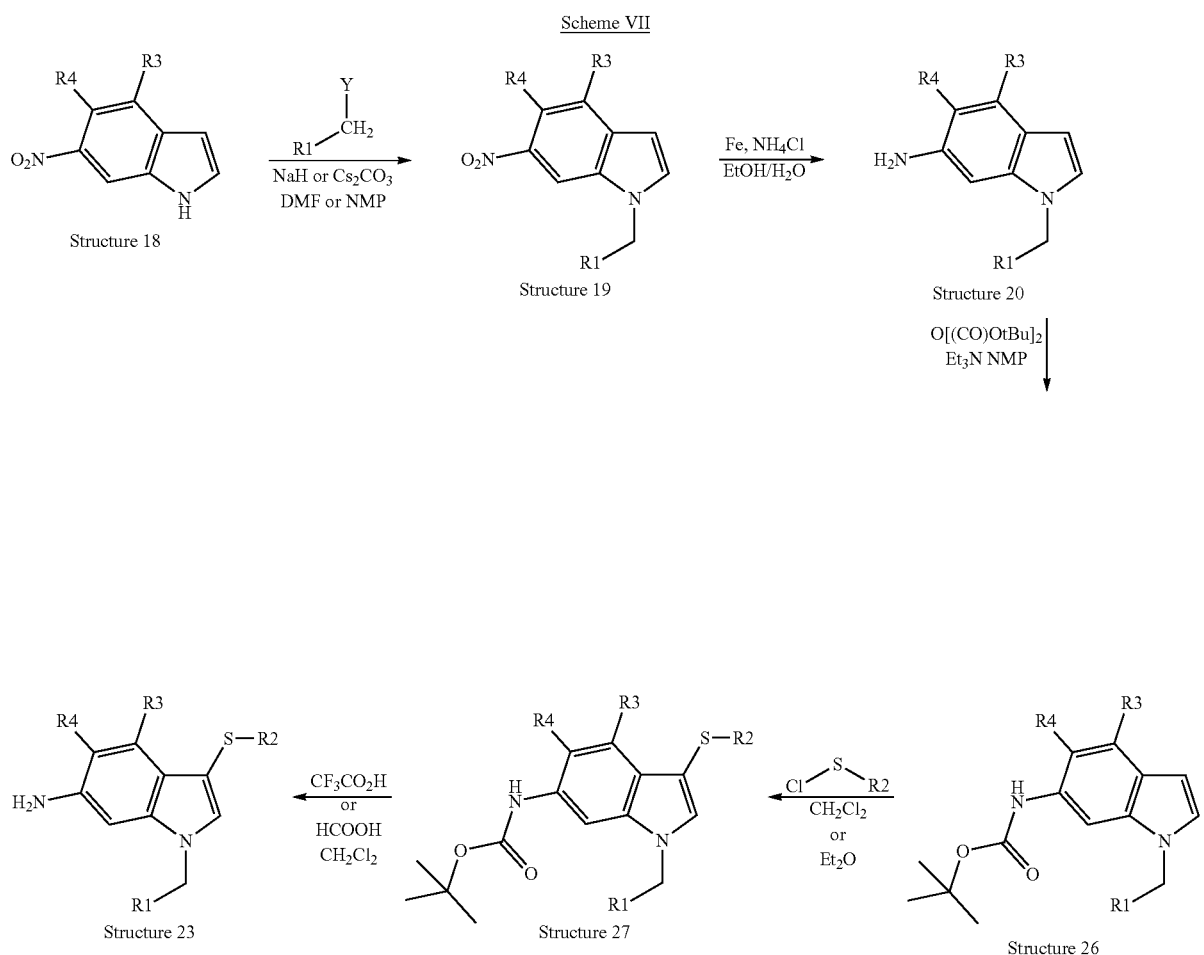

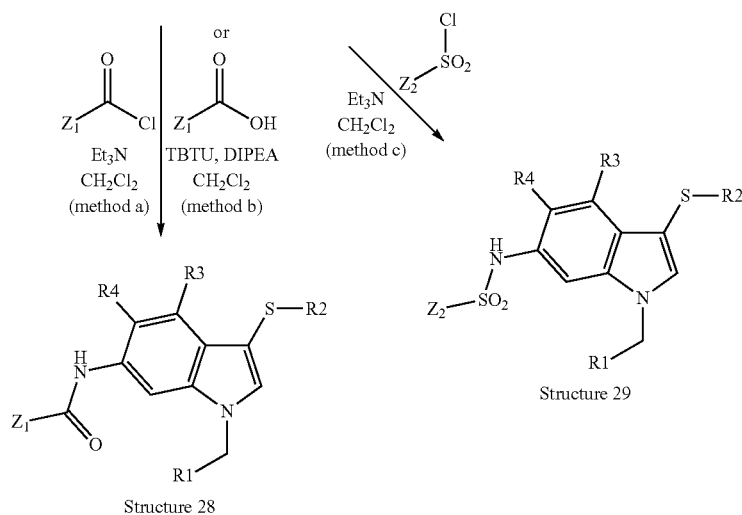

The present invention also relates to a pharmaceutical composition comprising the non-steroidal compound according to the invention mixed with a pharmaceutically acceptable auxiliary, such as described in the standard reference Gennaro et al, *Remmington: The Science and Practice of Pharmacy*, (20th ed., Lippincott Williams & Wilkins, 2000, see especially Part 5: Pharmaceutical Manufacturing). Suitable auxiliaries are made available in e.g. the Handbook of Pharmaceutical Excipients ($2^{nd}$ Edition, Editors A. Wade and P. J. Weller; American Pharmaceutical Association; Washington; The Pharmaceutical Press; London, 1994). The mixture of a compound according to the invention and a pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

The dosage amounts of the present compounds will be of the normal order for pharmaceutically active compounds, e.g. of the order of 0.001 to 50 mg/kg body weight of the recipient per administration. The recipient can be a human or an animal in need of an androgen receptor-related treatment or an androgen treatment.

The invention is illustrated by the following examples.

EXAMPLES

Example 1

1-(3,5-Difluoro-benzyl)-6-methoxy-3-(2-nitro-phenylsulfanyl)-1H-indole (Compound 63, Structure 3 of Scheme I, where $R^1$=3,5-difluorophenyl, $R^2$=2-nitrophenyl, $R^3$=$R^4$=H, $R^5$=OMe)

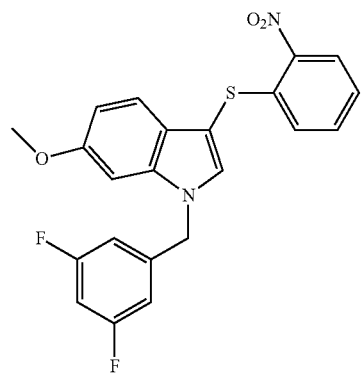

General method 1: N-alkylation of a (un)substituted indole of structure 1 to give N-alkylated indole of structure 2, followed by 3-sulfonylation to give substituted indoles of structure 3 (Scheme I).

(a) 1-(3,5-Difluoro-benzyl)-6-methoxy-1H-indole (Structure 2 of Scheme I, where $R^1$=3,5-difluorophenyl $R^3$=$R^4$=H, $R^5$=OMe)

Under a nitrogen atmosphere: to a cooled (0° C.) solution of 6-methoxyindole (863 mg, 5.86 mmol) in DMF (40 mL) was added NaH (60% in oil; 281 mg, 7.03 mmol) in small portions over a 3 minute period. The resulting green suspension was stirred at 0° C. for 10 min. Then 3,5-difluorobenzyl bromide (0.91 mL, 7.03 mmol) was added. The mixture was stirred at 0° C. for 1 h and then at room temperature for another 21 h. Ethyl acetate (50 mL) was added and the mixture was washed with 3% aqueous citric acid (3×50 mL) and brine (50 mL). The organic phase was dried (MgSO$_4$) and concentrated in vacuo to give a green oil (1.43 g). The crude product was purified over a 20 g silica SPE cartridge (ethyl acetate/heptane 1:9) to give the title compound as a colourless oil (1.23 g, yield=77%).

LCMS: 4.01 min (96.3%, MR$^+$=274); TLC (ethyl acetate/heptane 1:4): R$_f$=0.46; $^1$H NMR (CDCl$_3$): δ 3.80 (s, 3H, OCH$_3$), 5.24 (s, 2H, NCH$_2$Ar), 6.51 (dd, 1H, J1=3.5 Hz, J2=0.8 Hz), 6.57-6.60 (m, 2H), 6.65 (d, 1H, J=3.1 Hz), 6.66-6.72 (m, 1H), 6.81 (dd, 1H, J1=8.6 Hz, J2=3.1 Hz), 7.01 (d, 1H, J=3.5 Hz), 7.53 (d, 1H, J=8.6 Hz).

(b) 1-(3,5-Difluoro-benzyl)-6-methoxy-3-(2-nitrophenylsulfanyl)-1H-indole (Compound 63, Structure 3 of Scheme I, where $R^1$=3,5-difluorophenyl, $R^2$=2-nitrophenyl, $R^3$=$R^4$=H, $R^5$=OMe)

To a solution of 1-(3,5-Difluoro-benzyl)-6-methoxy-1H-indole (900 mg, 3.29 mmol) in diethyl ether (20 mL) was added dropwise at room temperature a suspension of 2-nitrobenzenesulfenyl chloride (627 mg, 3.31 mmol) in diethyl ether (10 mL) over a period of 2 min. After stirring at room temperature for 1 h ethyl acetate (50 mL) was added and the mixture was washed with saturated NaHCO$_3$ solution (2×50 mL) and brine (50 mL). The organic phase was dried (MgSO$_4$) and concentrated in vacuo to give an orange-red oil (1.54 g). The crude product was crystallised from toluene/acetone to give the title compound as orange-red crystalline solid (900 mg, yield=64%).

LCMS: 4.25 min (100%, MH$^+$=427); HPLC: 4.86 min (98.7%); $^1$H NMR (CDCl$_3$): δ 3.82 (s, 3H, OCH$_3$), 5.32 (s, 2H, NCH$_2$Ar), 6.63-6.69 (m, 2H), 6.72-6.79 (m, 1H), 6.75 (d, 1H, J=2.7 Hz), 6.85 (dd, 1H, J1=8.2 Hz, J2=2.7 Hz), 6.98 (dd, 1H, J1=6.7 Hz, J2=1.2 Hz), 7.16-7.20 (m, 1H), 7.26-7.30 (m, 1H) 7.34 (s, 1H), 7.39 (d, 1H, J=8.2 Hz), 8.27 (dd, 1H, J1=8.2 Hz, J2=1.6 Hz).

According to General method 1 the following compounds were prepared:

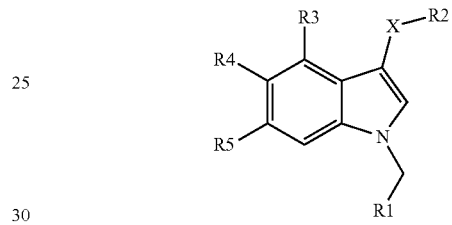

TABLE 1

Compounds synthesised according to General Method 1

| Compound number | X | $R^1$ | $R^2$ | $R^3$ | $R^4$ | $R^5$ | MWt | LCMS (MH+) | LCMS ret. Time[a] (min) |
|---|---|---|---|---|---|---|---|---|---|
| 21 | S | 3,5-difluorophenyl | 2-methoxyphenyl | H | H | OMe | 411.47 | 446[c] | 5.14[b] |
| 22 | S | 3,5-difluorophenyl | 2-nitrophenyl | H | H | Br | 475.32 | 476 | 4.89 |
| 23 | S | 3,5-difluorophenyl | 2-nitrophenyl | H | H | CF3 | 464.41 | 465 | 5.34[b] |
| 24 | S | 3,5-difluorophenyl | 2-nitrophenyl | H | H | CH2OH | 426.44 | Nd | 3.88[b] |
| 25 | S | 3,5-difluorophenyl | 2-nitrophenyl | H | H | Cl | 430.86 | 431 | 4.89 |
| 50 | S | 3,5-difluorophenyl | 2-nitrophenyl | H | H | F | 414.40 | 415 | 4.79 |
| 51 | S | 3,5-difluorophenyl | 2-nitrophenyl | F | H | H | 414.40 | 415 | 4.72 |
| 52 | S | 3,5-difluorophenyl | 2-nitrophenyl | H | H | H | 396.41 | 397 | 4.22 |
| 53 | S | 3,5-difluorophenyl | 2-nitrophenyl | H | F | H | 414.40 | 415 | 4.75 |
| 54 | S | 3,5-difluorophenyl | 2-nitrophenyl | Cl | H | H | 430.86 | 431 | 5.14[b] |
| 55 | S | 3,5-difluorophenyl | 2-nitrophenyl | Me | H | H | 410.44 | 411 | 5.24[b] |
| 56 | S | 3,5-difluorophenyl | 2-nitrophenyl | H | OH | H | 412.41 | 413 | 4.50[b] |
| 60 | S | 3,5-difluorophenyl | 2-nitrophenyl | H | H | NO2 | 441.41 | 442 | 4.7 |
| 61 | S | 3,5-difluorophenyl | 2-nitrophenyl | H | H | OH | 412.41 | 413 | 4.54[b] |
| 63 | S | 3,5-difluorophenyl | 2-nitrophenyl | H | H | OMe | 426.45 | 274[d] | 4.01 |
| 66 | S | 3,5-difluorophenyl | 2-pyridyl-N-oxide | H | H | OMe | 398.43 | 399 | 3.96 |
| 90 | S | phenyl | 2-nitrophenyl | H | H | H | 360.43 | 361 | 4.19 |
| 91 | S | phenyl | 2-nitrophenyl | H | OMe | H | 390.46 | 391 | 4.14 |
| 92 | S | Phenyl | 2-nitrophenyl | H | H | OMe | 390.46 | 391 | 4.12 |

[a]7 min LCMS method was used, unless stated otherwise.
[b]10 min LCMS method was used.
[c]M + Cl. nd = not detected.
[d]= [M—S(PhNO$_2$)]H$^+$.

Example 2

1-(3,5-Difluoro-benzyl)-3-(2-nitro-phenylsulfanyl)-1H-indole-6-carboxylic acid methyl ester (Compound 31, Structure 3 of Scheme I, where $R^1$=3,5-difluorophenyl, $R^2$=2-nitrophenyl, $R^3$=$R^4$=H, $R^5$=$CO_2$Me)

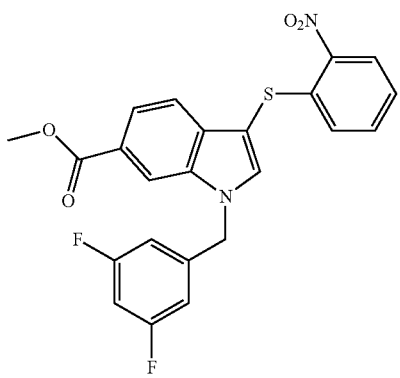

(a) 1H-Indole-6-carboxylic acid methyl ester (Structure 1 of Scheme I, where $R^3$=$R^4$=H, $R^5$=$CO_2$Me)

To a solution of 1H-Indole-6-carboxylic acid (1.500 g, 9.31 mmol) in methanol (50 mL) was added concentrated $H_2SO_4$ (550 μL, 10.24 mmol). The mixture was stirred overnight at reflux temperature. The mixture was then neutralised to pH 7 by addition of saturated aqueous $NaHCO_3$ and the mixture was extracted twice with ethyl acetate. The combined organic layers were dried over $Na_2SO_4$ and concentrated in vacuo to give a yellow powder. The product was recrystallised from heptane/ethyl acetate to give the title compound as green/yellow crystals (688 mg, yield=53%)

$^1$H NMR (CDCl$_3$): δ 3.94 (s, 3H, CH$_3$OCO), 6.60 (m, 1H), 7.37 (t, 1H, J=4.7 Hz), 7.66 (d, 1H, J=8.2 Hz), 7.82 (dd, 1H, J1=8.2 Hz, J2=1.0 Hz), 8.18 (s, 1H), 8.73 (s, 1H, NH)

(b) 1-(3,5-Difluoro-benzyl)-1H-indole-6-carboxylic acid methyl ester (Structure 2 of Scheme I, where $R^1$=3,5-difluorophenyl, $R^3$=$R^4$=H, $R^5$=$CO_2$Me)

Under a nitrogen atmosphere: to a solution of 1H-indole-6-carboxylic acid methyl ester (367 mg, 2.09 mmol) in DMF (10 mL) was added NaH (60% in oil, 101 mg, 2.52 mmol) at room temperature. After stirring for 15 min 1-bromomethyl-3,5-difluoro-benzene (325 μL, 2.51 mmol) was added and the mixture was stirred at room temperature for 4 h. The reaction was quenched with 3% aqueous citric acid (10 mL) and ethyl acetate (30 mL) was added. The mixture was washed with 3% aqueous citric acid (3×20 mL) and brine (20 mL). The organic phase was dried (MgSO$_4$) and concentrated in vacuo to give a pale yellow oil (702 mg). The crude product was purified over a 20 g silica SPE cartridge (ethyl acetate/heptane 1:9) to give the title compound as a colourless oil, which slowly crystallised on standing (530 mg, yield=84%).

LCMS: 4.08 min (99%, MH$^+$=302); $^1$H NMR (CDCl$_3$): δ 3.92 (3, 3H, CO$_2$CH$_3$), 5.37 (s, 2H, NCH$_2$Ar), 6.54-6.60 (m, 2H), 6.64 (d, 1H, J=3.1 Hz), 6.67-6.74 (m, 1H), 7.27 (d, 1H, J=3.1 Hz), 7.68 (d, 1H, J=8.6 Hz), 7.83 (d, 1H, J=8.6 Hz), 8.01 (s, 1H).

(c) 1-(3,5-Difluoro-benzyl)-3-(2-nitro-phenylsulfanyl)-1H-indole-6-carboxylic acid methyl ester (Compound 31, Structure 3 of Scheme I, where $R^1$=3,5-difluorophenyl, $R^2$=2-nitrophenyl, $R^3$=$R^4$=H, $R^5$=$CO_2$Me)

To a solution of 1-(3,5-Difluoro-benzyl)-1H-indole-6-carboxylic acid methyl ester (330 mg, 1.10 mmol) in dichloromethane (30 mL) was added at room temperature a solution of 2-nitrobenzenesulfenyl chloride (210 mg, 1.11 mmol) in dichloromethane (10 mL). The mixture was stirred at room temperature for 4 days. The reaction mixture was concentrated and the crude product was purified over a 20 g silica SPE cartridge (ethyl acetate/heptane 1:5 to 1:2) to give the title compound as a yellow solid (392 mg, yield=78%).

HPLC: 4.60 min (97.8%); $^1$H NMR (CDCl$_3$): δ 3.93 (s, 3H, CO$_2$CH$_3$), 5.45 (s, 2H, NCH$_2$Ar), 6.63-6.69 (m, 2H), 6.74-6.80 (m, 1H), 6.88 (dd, 1H, J1=8.2 Hz, J2=1.2 Hz), 7.18-7.23 (m, 1H), 7.26-7.30 (m, 1H), 7.57 (d, 1H, J=7.8 Hz), 7.58 (s, 1H), 7.89 (dd, 1H, J1=7.8 Hz, J2=1.2 Hz), 8.12 (s, 1H), 8.28 (dd, 1H, J1=7.8 Hz, J2=1.2 Hz).

Example 3

1-(3,5-Difluoro-benzyl)-3-(2-nitro-phenylsulfanyl)-1H-indole-6-carboxylic acid (Compound 30, Structure 14 of Scheme IV, where $R^1$=3,5-difluorophenyl, $R^2$=2-nitrophenyl, $R^3$=$R^4$=H)

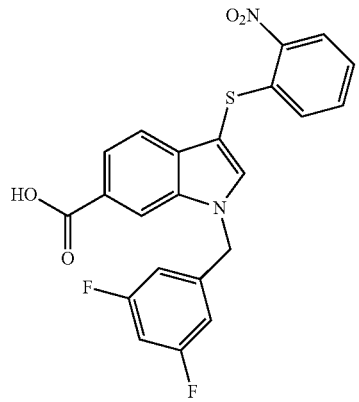

To a solution of 1-(3,5-Difluoro-benzyl)-3-(2-nitro-phenylsulfanyl)-1H-indole-6-carboxylic acid methyl ester (150.0 mg, 0.33 mmol) in dioxane (20 mL) and water (15 mL) was added LiOH.H$_2$O (83.1 mg, 2.0 mmol) in 5 ml water. The reaction mixture was stirred overnight at 60° C. The mixture was then acidified to pH 4 by addition of 15% aqueous HCl and the mixture was extracted twice with ethyl acetate. The combined organic layers were dried over Na$_2$SO$_4$ and concentrated in vacuo to give a yellow powder. The product was recrystallised from heptane/ethyl acetate to give the title compound as yellow/orange crystals (129.3 mg, y=89%)

$^1$H NMR (DMSO): δ 5.62 (s, 2H, CH$_2$Ar), 6.85 (dd, 1H, J1=8.6 Hz, J2=br), 7.05 (m, 2H, br), 7.20 (m, 1H, br), 7.32-7.38 (m, 1H), 7.40 (d, 1H, J=8.2 Hz), 7.44-7.50 (m, 1H), 7.68

(dd, 1H, J1=8.6 Hz, J2=br), 7.97 (s, 1H, COOH), 8.20 (s, 1H), 8.26 (s, 1H), 8.28 (d, 1H, J=8.2)

Example 4

1-(3,5-Difluoro-benzyl)-3-(2-nitro-phenylsulfanyl)-1H-indole-6-carboxylic acid methylamide (Compound 47, Structure 15 of Scheme IV, where $R^1$=3,5-difluorophenyl, $R^2$=2-nitrophenyl, $R^3$=$R^4$=$R^8$=H, $R^9$=Me)

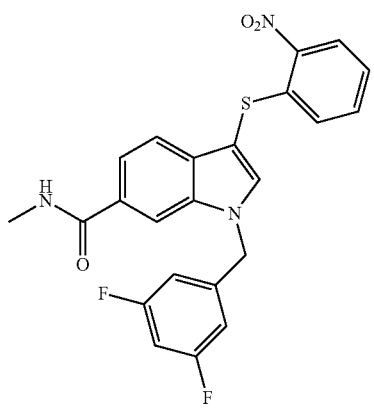

General method 2: amidation of 6-carboxyl indoles of structure 14 to give 6-carboxamideindoles of structure 15 (Scheme IV).

Under nitrogen atmosphere: to a solution of 1-(3,5-Difluoro-benzyl)-3-(2-nitro-phenylsulfanyl)-1H-indole-6-carboxylic acid (25.1 mg, 57.0 μmol) in dry DMF (10 mL) was added NMM (1 mL), HOBt (9.60 mg, 62.7 μmol), EDCI (12.1 mg, 62.7 μmol), and methylammonium chloride (19.2 mg, 285 μmol). The reaction mixture was stirred overnight at room temperature and then poured into ice water. The resulting precipitate was filtered and the residue was washed with excess water followed by little heptane. The product was dried in vacuo at 40° C. to give the title compound as a yellow solid (15.2 mg, y=60%).

LCMS: 4.31 min (100.0%, MH$^+$=454); $^1$H NMR (DMSO): δ 2.80(d, 3H, J=4.3, CH$_3$NHCO), 5.63 (s, 2H, CH$_2$Ar), 6.86 (dd, 1H, J1=8.2 Hz, J2=1.0 Hz), 7.04 (m, 2H), 7.20 (m, 1H), 7.33-7.37 (m, 1H), 7.41 (d, 1H, 8.6 Hz), 7.46-7.50 (m, 1H), 7.64 (dd, 1H, J1=8.2 Hz, J2=1.0 Hz), 8.15 (s, 1H), 8.25 (s, 1H), 8.27 (dd, 1H, J1=8.6 Hz, J2=1.0 Hz), 8.40 (m, 1H, MeNHCO).

According to General method 2 the following compounds were prepared:

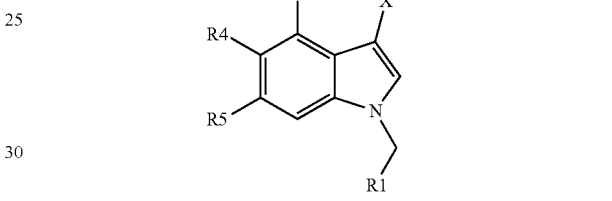

TABLE 2

Compounds synthesised according to General Method 2

| Compound number | X | $R^1$ | $R^2$ | $R^3$ | $R^4$ | $R^5$ | MWt | LCMS (MH+) | LCMS ret. Time$^a$ (min) |
|---|---|---|---|---|---|---|---|---|---|
| 27 | S | 3,5-difluorophenyl | 2-nitrophenyl | H | H | CO(1-pyrrolidinyl) | 493.53 | 494 | 4.66 |
| 28 | S | 3,5-difluorophenyl | 2-nitrophenyl | H | H | CO(4-morpholinyl) | 509.53 | 510 | 4.50 |
| 29 | S | 3,5-difluorophenyl | 2-nitrophenyl | H | H | CO[1-(4-methylpiperazinyl)] | 522.57 | 523 | 3.81 |
| 32 | S | 3,5-difluorophenyl | 2-nitrophenyl | H | H | CONEt2 | 495.55 | 496 | 4.82 |
| 34 | S | 3,5-difluorophenyl | 2-nitrophenyl | H | H | CONHCH2(2-furanyl) | 519.53 | 520 | 4.74 |
| 35 | S | 3,5-difluorophenyl | 2-nitrophenyl | H | H | CONHCH2(3-pyridyl) | 530.55 | 531 | 3.94 |
| 36 | S | 3,5-difluorophenyl | 2-nitrophenyl | H | H | CONHCH2CH2NMe2 | 510.56 | 511 | 3.90 |
| 37 | S | 3,5-difluorophenyl | 2-nitrophenyl | H | H | CONHCH2CH2OH | 483.49 | 484 | 4.21 |
| 38 | S | 3,5-difluorophenyl | 2-nitrophenyl | H | H | CONHCH2CH2OMe | 497.52 | 498 | 4.48 |
| 39 | S | 3,5-difluorophenyl | 2-nitrophenyl | H | H | CONHCH2CO2Me | 511.50 | 512 | 4.51 |
| 40 | S | 3,5-difluorophenyl | 2-nitrophenyl | H | H | CONHCH2CONMe2 | 524.55 | 525 | 4.33 |
| 41 | S | 3,5-difluorophenyl | 2-nitrophenyl | H | H | CONHCH2cPr | 493.53 | 494 | 4.75 |
| 42 | S | 3,5-difluorophenyl | 2-nitrophenyl | H | H | CONHCH2iPr | 495.55 | 496 | 4.85 |
| 43 | S | 3,5-difluorophenyl | 2-nitrophenyl | H | H | CONHCH2Ph | 529.56 | 530 | 4.90 |
| 44 | S | 3,5-difluorophenyl | 2-nitrophenyl | H | H | CONHcPr | 479.50 | 480 | 4.57 |
| 45 | S | 3,5-difluorophenyl | 2-nitrophenyl | H | H | CONHEt | 467.49 | 468 | 4.56 |
| 46 | S | 3,5-difluorophenyl | 2-nitrophenyl | H | H | CONHiPr | 481.52 | 482 | 4.71 |
| 47 | S | 3,5-difluorophenyl | 2-nitrophenyl | H | H | CONHMe | 453.47 | 454 | 4.31 |
| 48 | S | 3,5-difluorophenyl | 2-nitrophenyl | H | H | CONHnPr | 481.52 | 482 | 4.75 |
| 49 | S | 3,5-difluorophenyl | 2-nitrophenyl | H | H | CONMe2 | 467.49 | 468 | 4.30$^b$ |

$^a$7 min LCMS method was used, unless stated otherwise.
$^b$10 min LCMS method was used.

Example 5

1-(3,5-Difluoro-benzyl)-3(2-nitro-phenylsulfanyl)-1H-indole-6-carboxylic acid amide (Compound 33, Structure 16 of Scheme IV, where R¹=3,5-difluorophenyl, R²=2-nitrophenyl, R³=R⁴=H)

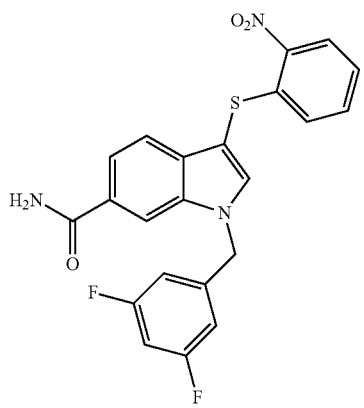

The title compound was prepared according to General method 2, using 51.1 mg (116 μmol) carboxylic acid, 19.5 mg (128 μmol) HOBt, 24.6 mg (128 μmol) EDCI and 31.1 mg (581 μmol) ammonium chloride. The title compound was obtained as a yellow solid (9.0 mg; 18%).

LCMS: 4.16 min (100.0%, MH⁺=440); ¹H NMR (CDCl₃): δ 5.46 (s, 2H, CH₂Ar), 6.65 (m, 2H), 6.77 (m, 1H), 6.88 (dd, 1H, J1=8.2 Hz, J2=1.0 Hz)), 7.21 (m, 1H), 7.29 (m, 1H), 7.51 (dd, 1H, J1=7.8 Hz, J2=1.0 Hz), 7.57 (d, 1H, J=7.7 Hz), 7.58 (s, 1H), 8.05 (s, 1H), 8.29 (dd, 1H, J1=8.2 Hz, J2=1.0 Hz).

Example 6

6-Methoxy-3-(2-nitro-phenylsulfanyl)-1-pyridin-2-ylmethyl-1H-indole (Compound 9, Structure 3 of Scheme I, where R¹=2-pyridyl, R²=2-nitrophenyl, R³=R⁴=H, R⁵=OMe)

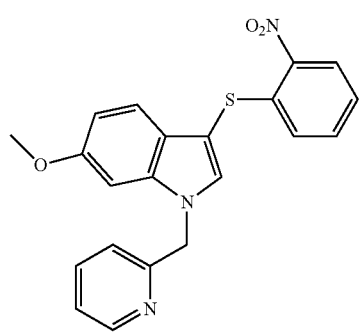

General method 3: 3-sulfonylation of a (un)substituted indole of structure 1 to give substituted indoles of structure 4, followed by indole-N-alkylation to give N-alkylated indole structure 3 (Scheme I).

(a) 6-Methoxy-3-(2-nitro-phenylsulfanyl)-1H-indole (Structure 4 of Scheme I, where R²=2-nitrophenyl, R¹=R³=R⁴=H, R⁵=OMe)

To a solution of 6-methoxyindole (1.5 g, 10.2 mmol) in Et₂O (100 mL) was added a solution of 2-nitrobenzenesulfenyl chloride (1.93 g, 10.2 mmol) in 50 mL Et₂O dropwise, over a 4 minute period. The resulting yellow solution was stirred at room temperature for 1 h. The solvent was evaporated and the crude product was purified over a silica column (heptane/ethyl acetate 9:1) to give the title compound (3.054 g, yield=97%).

HPLC: 3.72 min. purity 96.7%, TLC (heptane/ethyl acetate 1:1): R_f=0.6;
¹H NMR (CDCl₃): δ 3.87 (s, 3H, OCH3), 6.84 (dd, 1H, J1=7.8 Hz, J2=3.13 Hz), 6.97 (m, 2H), 7.16 (t, 1H, J=7.8 Hz), 7.25 (t, 1H, J=7.8 Hz), 7.36 (d, 1H, J=7.8 Hz), 7.44 (d, 1H, J=2.0 Hz), 8.26 (d, 1H, J=7.8 Hz), 8.45 (s, 1H, NH).

(b) 6-Methoxy-3-(2-nitro-phenylsulfanyl)-1-pyridin-2-ylmethyl-1H-indole (Compound 9, Structure 3 of Scheme I, where R¹=2-pyridyl, R²=2-nitrophenyl, R³=R⁴=H, R⁵=OMe)

To a solution of 6-Methoxy-3-(2-nitro-phenylsulfanyl)-1H-indole (1.5 g, 5 mmol) in DMF (150 mL) was added NaH (60% in oil; 500 mg, 12.5 mmol) in small portions, over a 4 minute period. The resulting dark solution was stirred for 5 min. at room temperature. Then 2-picolyl chloride hydrochloride (984 mg, 6 mmol) was added in small portions, over a 2 minute period. During stirring at room temperature (2 h) the colour of the solution slightly changed from dark to yellow. Ethyl acetate (100 mL) was added and the mixture was washed with 2% aqueous citric acid (2×100 mL) and water (100 mL). The organic phase was dried (MgSO4) and the solvent was evaporated. The crude product was purified by crystallisation (ethyl acetate/heptane) to give the title compound (1.437 g, yield=74%).

HPLC: 10.3 min, purity 99.6%, TLC (heptane/ethyl acetate 1:1): R_f=0.3;
¹H NMR (CDCl₃): δ 3.80 (s, 3H, OCH3), 5.47 (s, 2H, NCH₂), 6.82 (m, 2H), 6.88 (d, 1H, J=7.8 Hz), 7.01 (dd, 1H, J1=7.8 Hz, J2=1.6 Hz), 7.15-7.19 (m, 1H), 7.25 (m, 2H), 7.37 (d, 1H, j=8.6 Hz), 7.60-7.64 (m, 1H), 8.26 (dd, 1H, J1=7.8 Hz, J2=1.6 Hz), 8.63 (d, 1H, J=5.88 Hz).

According to General method 3 the following compounds were prepared:

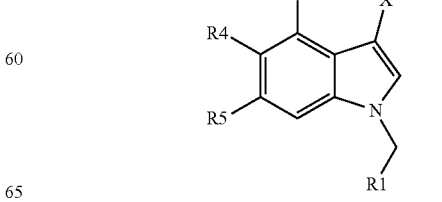

TABLE 3

Compounds synthesised according to General Method 3

| Compound number | X | R¹ | R² | R³ | R⁴ | R⁵ | MWt | LCMS (MH+) | LCMS ret. Time[a] (min) |
|---|---|---|---|---|---|---|---|---|---|
| 1 | S | 2,5-difluorophenyl | 2-nitrophenyl | H | H | OMe | 426.44 | 427 | 4.07 |
| 2 | S | 2,fluoro,3-methylphenyl | 2-nitrophenyl | H | H | OMe | 422.48 | 423 | 4.23 |
| 3 | S | 2-chlorophenyl | 2-nitrophenyl | H | H | OMe | 424.91 | 425 | 4.17 |
| 4 | S | 2-cyanophenyl | 2-nitrophenyl | H | H | OMe | 415.47 | 416 | 3.97 |
| 5 | S | 2-fluorophenyl | 2-nitrophenyl | H | H | OMe | 408.45 | 409 | 4.10 |
| 6 | S | 2-methyl,3-nitrophenyl | 2-nitrophenyl | H | H | OMe | 449.48 | 450 | 4.10 |
| 7 | S | 2-methylphenyl | 2-nitrophenyl | H | H | OMe | 404.49 | 405 | 4.16 |
| 8 | S | 2-nitrophenyl | 2-nitrophenyl | H | H | OMe | 435.46 | 436 | 4.08 |
| 9 | S | 2-pyridyl | 2-nitrophenyl | H | H | OMe | 391.45 | | 10.30[b] |
| 11 | S | 2-tetrahydropyranyl | 2-nitrophenyl | H | H | OMe | 398.48 | 399 | 4.68 |
| 12 | S | 2-trifluoromethylphenyl | 2-nitrophenyl | H | H | OMe | 458.46 | 459 | 4.29 |
| 13 | S | 3-(5-methylisoxazolyl) | 2-nitrophenyl | H | H | OMe | 395.44 | 396 | 4.66 |
| 14 | S | 3,4-dichlorophenyl | 2-nitrophenyl | H | H | OMe | 459.35 | 459 | 4.33 |
| 15 | S | 3,5-dichlorophenyl | 2-nitrophenyl | H | H | OMe | 459.35 | 459 | 4.36 |
| 67 | S | 3-chlorophenyl | 2-nitrophenyl | H | H | OMe | 424.91 | 425 | 4.34 |
| 68 | S | 3-cyanophenyl | 2-nitrophenyl | H | H | OMe | 415.47 | 416 | 3.92 |
| 69 | S | 3-fluoro,5-trifluoromethylphenyl | 2-nitrophenyl | H | H | OMe | 476.45 | 477 | 4.42 |
| 70 | S | 3-fluoro,6-trifluoromethylphenyl | 2-nitrophenyl | H | H | OMe | 476.45 | 477 | 4.27 |
| 71 | S | 3-fluorophenyl | 2-nitrophenyl | H | H | OMe | 408.45 | 409 | 4.22 |
| 72 | S | 3-methoxyphenyl | 2-nitrophenyl | H | H | OMe | 420.49 | 421 | 4.04 |
| 73 | S | 3-methylphenyl | 2-nitrophenyl | H | H | OMe | 404.49 | 405 | 4.16 |
| 74 | S | 3-nitrophenyl | 2-nitrophenyl | H | H | OMe | 435.46 | 436 | 4.00 |
| 75 | S | 3-pyridyl | 2-nitrophenyl | H | H | OMe | 391.45 | 392 | 3.28 |
| 76 | S | 3-trifluoromethyl,4-chlorophenyl | 2-nitrophenyl | H | H | OMe | 492.90 | 493 | 4.33 |
| 77 | S | 3-trifluoromethyloxyphenyl | 2-nitrophenyl | H | H | OMe | 474.46 | 475 | 4.43 |
| 78 | S | 3-trifluoromethylphenyl | 2-nitrophenyl | H | H | OMe | 458.46 | 459 | 4.21 |
| 79 | S | 4-(2-methylthiazolyl) | 2-nitrophenyl | H | H | OMe | 411.50 | 412 | 4.39 |
| 80 | S | 4-(3,5-dimethylisoxazolyl) | 2-nitrophenyl | H | H | OMe | 409.46 | 410 | 4.49 |
| 81 | S | 4-chlorophenyl | 2-nitrophenyl | H | H | OMe | 424.91 | 425 | 4.22 |
| 82 | S | 4-cyanophenyl | 2-nitrophenyl | H | H | OMe | 415.47 | 416 | 3.93 |
| 83 | S | 4-fluorophenyl | 2-nitrophenyl | H | H | OMe | 408.45 | 409 | 4.07 |
| 84 | S | 4-methoxyphenyl | 2-nitrophenyl | H | H | OMe | 420.49 | 421 | 4.03 |
| 85 | S | 4-methylphenyl | 2-nitrophenyl | H | H | OMe | 404.49 | 405 | 4.19 |
| 86 | S | 4-morpholinyl | 2-nitrophenyl | H | H | OMe | 413.50 | 414 | 3.54 |
| 87 | S | 5-(2-chlorothiazolyl) | 2-nitrophenyl | H | H | OMe | 431.92 | 432 | 4.61 |
| 88 | S | 5-(2-chlorothiophenyl) | 2-nitrophenyl | H | H | OMe | 430.93 | 431 | 4.92 |
| 89 | S | cyclohexyl | 2-nitrophenyl | H | H | OMe | 396.51 | 397 | 5.11 |

[a] 7 min LCMS method was used unless stated otherwise.
[b] a 20 min run on an HPLC system was used.

Example 7

1-(3,5-Difluoro-benzyl)-6-methoxy-3-(pyridin-2-ylsulfanyl)-1H-indole (Compound 65, Structure 3 of Scheme I, where R¹=3,5-difluorophenyl, R²=2-pyridyl, R³=R⁴=H, R⁵=OMe)

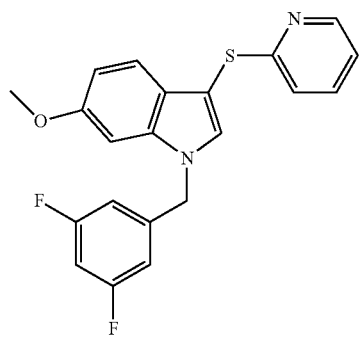

Under a nitrogen atmosphere: to a cooled (−10° C.) solution of 2-mercaptopyridine (25 mg, 0.22 mmol) in CCl₄ (2 mL) was passed Cl₂-gas during a period of 1 minute. The solvent was evaporated and a solution of 1-(3,5-Difluoro-benzyl)-6-methoxy-1H-indole (25 mg, 0.09 mmol) in Et₂O (2 mL) was added dropwise. The reaction mixture was concentrated and the crude product was purified by preparative LCMS to give the title compound (7.77 mg, yield=23%).

LCMS: 3.95 min (100%, MH⁺ 383); TLC (heptane/ethyl acetate 1:1): $R_f$=0.6;

¹H-NMR (CDCl₃): δ 2.23 (s, 1H, NH), 3.82 (s, 1H, OCH₃), 6.65 (m, 2H), 6.73 (d, 1H, J=2.7 Hz), 6.73-6.78 (m, 1H), 6.80 (d, 1H, J=7.8 Hz), 6.87 (dd, 1H, J1=7.8 Hz, J2=1.6 Hz), 7.00 (ddd, 1H, J1=9.8 Hz, J2=4.7 Hz, J3=0.8 Hz), 7.35 (s, 1H), 7.42 (ddd, 1H, J1=J2=7.8 Hz, J3=1.6 Hz), 7.50 (d, 1H, 8.6 Hz), 8.46 (d, 1H, J=4.7 Hz).

Example 8

{2-[1-(3,5-Difluoro-benzyl)-6-methoxy-1H-indol-3-ylsulfanyl]-phenyl}-methanol (Compound 16, Structure 8 of Scheme III, where $R^1$=3,5-difluorophenyl, $R^3$=$R^4$=H, $R^5$=OMe)

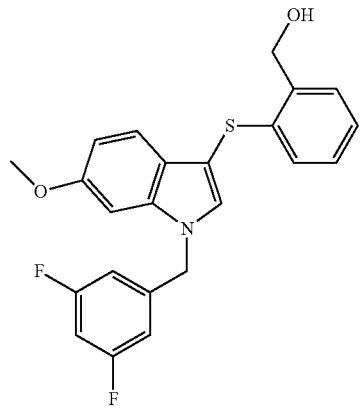

a) 2-[1-(3,5-Difluoro-benzyl)-6-methoxy-1H-indol-3-ylsulfanyl]-benzoic acid methyl ester (Compound 19, Structure 7 of Scheme III, where $R^1$=3,5-difluorophenyl, $R^3$=$R^4$=H, $R^5$=OMe)

Chlorine gas was bubbled through $CCl_4$ (5 mL) at −10° C. for 3 min. Then a solution of methylthiosalicylate (91 µL, 0.66 mmol) in $CCl_4$ (2 mL) was added. The mixture was stirred at −10° C. for 5 min and then at room temperature for 15 min. The mixture was concentrated and redissolved in $CH_2Cl_2$ (5 mL). To this solution a solution of 1-(3,5-Difluoro-benzyl)-6-methoxy-1H-indole (121 mg, 0.443 mmol) in $CH_2Cl_2$ (3 mL) was added dropwise. The mixture was stirred at room temperature for 2 h and was concentrated. The crude product was purified by column chromatography (ethyl acetate/heptane 1:9) to give the title compound as a white solid (161 mg, 83% yield). LCMS: 4.72 min (MH$^+$=440); $^1$H-NMR (CDCl$_3$): δ 3.82 (s, 3H, ArOCH$_3$), 3.99 (s, 3H, CO$_2$CH$_3$), 5.30 (s, 2H, CH$_2$Ar), 6.62-6.69 (m, 2H), 6.71-6.77 (m, 2H), 6.83 (dd, 1H, J1=8.6 Hz, J2=2.4 Hz), 6.87 (dd, 1H, J1=8.4 Hz, J2=1.2 Hz), 7.06-7.11 (m, 1H, 7.15-7.20 (m, 1H), 7.30 (s, 1H), 7.44 (d, 1H, J=8.6 Hz), 8.02 (dd, 1H, J1=8.0 Hz, J2=1.2 Hz).

b) {2-[1-(3,5-Difluoro-benzyl)-6-methoxy-1H-indol-3-ylsulfanyl]-phenyl}-methanol (Compound 16, Structure 8 of Scheme III, where $R^1$=3,5-difluorophenyl, $R^3$=$R^4$=H, $R^5$=OMe)

Under a nitrogen atmosphere: to a solution of 2-[1-(3,5-Difluoro-benzyl)-6-methoxy-1H-indol-3-ylsulfanyl]-benzoic acid methyl ester (13.5 mg, 0.031 mmol) in THF (2 mL) was added LiAlH$_4$ (1.0 M in THF, 0.040 mL, 0.040 mmol). The mixture was stirred at room temperature for 3 h. Then ethyl acetate (25 mL) was added and the mixture was washed with 3% aqueous citric acid (2×25 mL) and brine (25 mL). The organic phase was dried (MgSO$_4$) and concentrated to give a colourless oil (15 mg). The crude product was purified by prep. HPLC to give the title compound as a colourless oil (5.6 mg, 44% yield).

LCMS: 4.47 min (95.6%, MH$^+$=412); $^1$H-NMR (CDCl$_3$): δ 3.49 (s, 1H, OH), 3.81 (3, 3H, OCH$_3$), 4.92 (s, 2H, CH$_2$OH), 5.28 (s, 2H, CH$_2$Ar), 6.62-6.66 (m, 2H), 6.70-6.77 (m, 2H), 6.83 (dd, 1H, J1=8.8 Hz, J2=2.4 Hz), 6.89 (dd, 1H, J1=8.0 Hz, J2=1.2 Hz), 7.02-7.07 (m, 1H), 7.08-7.13 (m, 1H), 7.29 (s, 1H), 7.38 (dd, 1H, J1=8.0 Hz, J2=1.2 Hz), 7.44 (d, 1H, J=8.8 Hz).

Example 9

2-[1-(3,5-Difluoro-benzyl)-6-methoxy-1H-indol-3-ylsulfanyl]-benzamide (Compound 18, Structure 11 of Scheme III, where $R^1$=3,5-difluorophenyl, $R^3$=$R^4$=H, $R^5$=OMe)

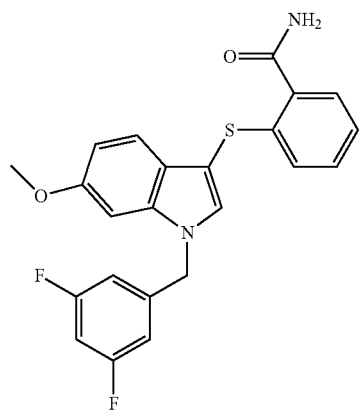

a) 2-[1-(3,5-Difluoro-benzyl)-6-methoxy-1H-indol-3-ylsulfanyl]-benzoic acid (Structure 9 of Scheme III, where $R^1$=3,5-difluorophenyl, $R^3$=$R^4$=H, $R^5$=OMe)

To a solution of 2-[1-(3,5-Difluoro-benzyl)-1H-indol-3-ylsulfanyl]-benzoic acid methyl ester (97 mg, 0.221 mmol) in THF (10 mL) was added a solution of LiOH.H$_2$O (71 mg, 1.69 mmol) in water (10 mL). The mixture was stirred at room temperature for 17 h and then at 60° C. for 24 h and was then acidified with 3% aqueous citric acid. Ethyl acetate (50 mL) was added and the mixture was washed with 3% aqueous citric acid (2×50 mL) and brine (50 mL). The organic phase was dried (MgSO$_4$) and concentrated to give a yellow solid (104 mg). The crude product was recrystallised from ethyl acetate/heptane to give the title compound as a yellow powder (49 mg, 52% yield).

LCMS: 4.37 min (MH$^+$=426); $^1$H-NMR (CDCl$_3$): δ 337 (s, 3H, OCH$_3$), 5.51 (s, 2H, CH$_2$Ar), 6.69 (d, 1H, J=8.0 Hz), 6.76 (dd, 1H, J1=8.4 Hz, J2=2.4 Hz), 6.98-7.04 (m, 2H), 7.11-7.15 (m, 1H), 7.16-7.25 (m, 4H), 7.83 (s, 1H), 7.92 (dd, 1H, J1=8.0 Hz, J2=1.6 Hz).

General method 4: Reaction of an amine with a carboxylic acid of structure 9, with TBTU and DIPEA, to give amides of structure 3, in which $R^2$=phenyl-2-carboxamide, exemplified by compounds of structure 10 and 11 (Scheme III).

b) 2-[1-(3,5-Difluoro-benzyl)-6-methoxy-1H-indol-3-ylsulfanyl]-benzamide (Compound 18, Structure 11 of Scheme III, where $R^1$=3,5-difluorophenyl, $R^3$=$R^4$=H, $R^5$=OMe)

Through a solution of 2-[1-(3,5-Difluoro-benzyl)-6-methoxy-1H-indol-3-ylsulfanyl]-benzoic acid (36 mg, 0.085 mmol), TBTU (28 mg, 0.087 mmol) and DIPEA (30 µL, 0.172 mmol) in DMF (1 mL) was bubbled NH$_3$ gas for 10 min. The mixture was then stirred at room temperature for 3 days. Then 3% aqueous citric acid (0.4 mL) was added and the crude reaction mixture was purified over a RP-SPE cartridge (2 g sorbent; 25% aqueous methanol to 100% methanol) to give a white solid (34 mg). The crude product was purified by column chromatography (ethyl acetate) to give the title compound as a colourless oil, which solidifies on standing (31 mg, yield: 86%).

LCMS: 4.20 min MH$^+$=425); $^1$H-NMR (CDCl$_3$): δ 3.81 (s, 3H, OCH$_3$), 5.39 (s, 2H, CH$_2$Ar), 6.05 (s, br, 1H, NH), 6.28 (s, br, 1H, NH), 6.61-6.67 (m, 2H), 6.70-6.72 (m, 1H), 6.73-6.77 (m, 1H), 6.83 (dd, 1H, J1=8.8 Hz, J2=2.0 Hz), 6.92 (dd, 1H, J1=8.0 Hz, J2=1.2 Hz), 7.07-7.17 (m, 2H), 7.31 (s, 1H), 7.45 (d, 1H, J=8.8 Hz), 7.60 (dd, 1H, J1=8.0 Hz, J2=1.2 Hz).

Example 10

2-[1-(3,5-Difluoro-benzyl)-6-methoxy-1H-indol-3-ylsulfanyl]-N-methyl-benzamide (Compound 17, Structure 10 of Scheme III, where R$^1$=3,5-difluorophenyl, R$^3$=R$^4$=H, R$^5$=OMe)

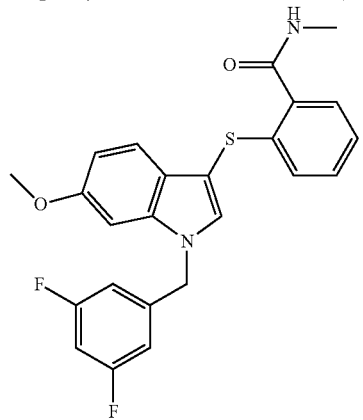

According to general method 4 compound 17 was synthesised from methylamine. LCMS: 4.07 min (MH$^+$=439).

Example 11

2-[1-(3,5-Difluoro-benzyl)-6-methoxy-1H-indol-3-ylsulfanyl]-benzonitrile (Compound 20, Structure 12 of Scheme III, where R$^1$=3,5-difluorophenyl, R$^3$=R$^4$=H, R$^5$=OMe)

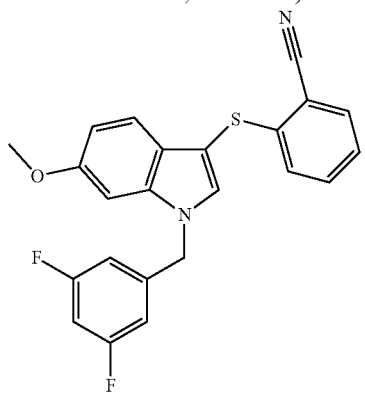

To a cooled (0° C.) solution of 2-[1-(3,5-Difluoro-benzyl)-6-methoxy-1H-indol-3-ylsulfanyl]-benzamide (8 mg, 0.019 mmol) and Et$_3$N (10 μL, 0.072 mmol) in CH$_2$Cl$_2$ (1.5 mL) was added Tf$_2$O (6 μL, 0.036 mmol). The mixture was stirred at 0° C. for 2 h and then at room temperature for 22 h. Water (25 mL) was added and the mixture was extracted with CH$_2$Cl$_2$ (2×25 mL). The combined organic phases were dried (Na$_2$SO$_4$) and concentrated to give a brown oil (25 mg). The crude product was purified by column chromatography (ethyl acetate/heptane 1:2) to give the title compound as a pale pink oil (3 mg, yield: 39%).

LCMS: 4.57 min (MH$^+$=407); $^1$H-NMR (CDCl$_3$): δ 3.82 (s, 3H, OCH$_3$), 5.30 (s, 2H, CH$_2$Ar), 6.62-6.67 (m, 2H), 6.71-6.73 (m, 1H), 6.74-6.78 (m, 1H), 6.86 (dd, 1H, J1=8.8 Hz, J2=2.0 Hz), 6.91 (d, 1H, J=8.4 Hz), 7.11-7.15 (m, 1H), 7.26-7.30 (m, 1H), 7.37 (s, 1H), 7.46 (d, 1H, J=8.8 Hz), 7.57-7.60 (m, 1H).

Example 12

1-(3,5-Difluoro-benzyl)-3-(2-nitro-phenylsulfanyl)-1H-indole-6-carbonitrile (Compound 26, Structure 17 of Scheme IV, where R$^1$=3,5-difluorophenyl, R$^2$=2-nitrophenyl, R$^3$=R$^4$=H)

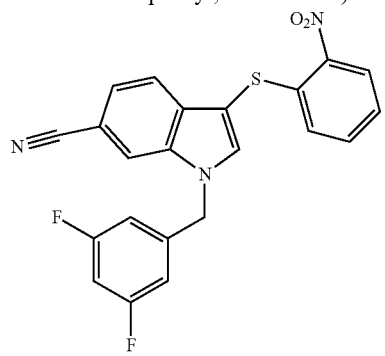

To a cooled (0° C.) suspension of 1-(3,5-Difluoro-benzyl)-3-(2-nitro-phenylsulfanyl)-1H-indole-6-carboxylic acid amide (15 mg, 0.034 mmol) and Et$_3$N (10 μL, 0.072 mmol) in CH$_2$Cl$_2$ (1.5 mL) was added Tf$_2$O (13 μL, 0.077 mmol). The mixture was stirred at 0° C. for 2 h and then at room temperature for 20 h. Water (25 mL) was added and the mixture was extracted with CH$_2$Cl$_2$ (2×25 mL). The combined organic phases were dried (Na$_2$SO$_4$) and concentrated to give the title compound as a yellow solid (13 mg, yield: 91%).

LCMS: 4.55 min (MH$^+$=not detectable); $^1$H-NMR (CDCl$_3$): δ 5.42 (s, 2H, CH$_2$Ar), 6.63-6.69 (m, 2H), 6.78-6.85 (m, 2H), 7.21-7.25 (m, 1H), 7.28-7.33 (m, 1H), 7.44 (dd, 1H, J1=8.4 Hz, J2=1.2 Hz), 7.62 (d, 1H, J=8.4 Hz), 7.66 (s, 1H), 8.29 (dd, 1H, J1=8.4 Hz, J2=1.6 Hz).

Example 13

1-(3,5-Difluoro-benzyl)-6-methoxy-3-(2-nitro-benzenesulfinyl)-1H-indole (Compound 64, Structure 5 of Scheme II, where R$^1$=3,5-difluorophenyl R$^2$=2-nitrophenyl, R$^3$=R$^4$=H, R$^5$=OMe)

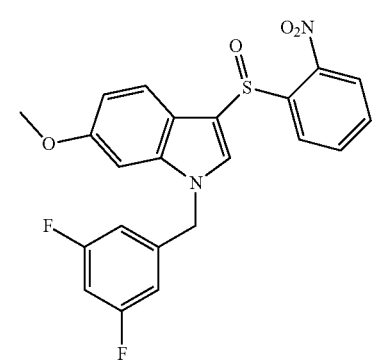

To a solution of 1-(3,5-Difluoro-benzyl)-6-methoxy-3-(2-nitro-phenylsulfanyl)-1H-indole (40 mg, 0.09 mmol) in CH$_2$Cl$_2$ (4 mL) was added meta-chloroperbenzoic acid (14.5, 0.08 mmol). The solution was stirred at room temperature for 2 h. The solvent was evaporated and the crude product was purified by prep LC-MS to give the title compound (14.3 mg, yield=34%).

HPLC: 4.13 min, purity 100%; TLC (heptane/ethyl acetate 1:1): Rf=0.4; $^1$H NMR (CDCl$_3$): δ 3.66 (s, 3H, OCH3), 5.12 (s, 2H), 6.57 (m, 3H), 6.75 (m, 2H), 7.47 (d, 1H, J=7.8 Hz), 7.52 (s, 1H), 7.66-7.70 (m, 1H), 8.28-8.32 (m, 1H), 8.23 (dd, 1H, J1=7.8 Hz, J2=1.9 Hz), 8.80 (dd, 1H, J1=7.8 Hz, J2=3.1 Hz).

Example 14

1-(3,5-Difluoro-benzyl)-6-methoxy-3-(2-nitro-benzenesulfonyl)-1H-indole (Compound 62, Structure 6 of Scheme II, where R$^1$=3,5-difluorophenyl, R$^2$=2-nitrophenyl, R$^3$=R$^4$=H, R$^5$=OMe)

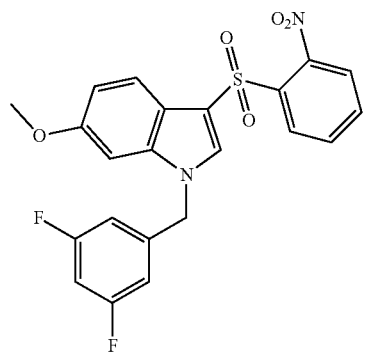

To a solution of 1-(3,5-Difluoro-benzyl)-6-methoxy-3-(2-nitro-phenylsulfanyl)-1H-indole (40 mg, 0.09 mmol) in CH$_2$Cl$_2$ (4 mL) was added meta-chloroperbenzoic acid (46.5 mg, 0.27 mmol). The solution was stirred at room temperature for 6 h. The solvent was evaporated and the crude product was purified by LC-MS to give the title compound (14.5 mg, yield=34%).

HPLC: 4.38 min. purity 100%; TLC (heptane/ethyl acetate 1:1): Rf=0.6; $^1$H NMR (CDCl$_3$): δ 3.71 (s, 3H, OCH3), 5.25 (s, 2H), 6.58 (d, 1H, J=3.1), 6.62 (m, 1H), 6.07-6.11 (m, 1H), 6.88 (dd, 1H, J1=7.8 Hz, J2=3.1 Hz), 7.63 (m, 4H), 7.72 (d, 1H, J=7.8 Hz), 7.83 (s, 1H), 8.37 (dd, 1H, J1=7.8 Hz, J2=1.9 Hz).

Example 15

6-Methoxy-3-(2-nitro-phenylsulfanyl)-1-pyridin-2-ylmethyl-1H-indole monohydrochloride (Compound 10)

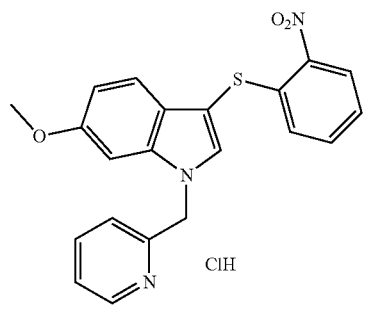

To a solution of 6-Methoxy-3-(2-nitro-phenylsulfanyl)-1-pyridin-2-ylmethyl-1H-indole in methylene chloride was passed HCl-gas till the organic salt crystallised. The title compound was isolated by filtration.

LC-MS: 4.04 min (MH$^+$=392); $^1$H NMR (DMSO): δ 3.78 (s, 3H, OCH3), 5.78 (s, 2H, NCH$_2$), 6.77 (dd, 1H, J1=7.8 Hz, J2=2.0 Hz), 6.93 (dd, 1H, J1=7.8 Hz, J2=0.8 Hz), 7.22 (d, 1H, J=7.8 Hz), 7.26 (d, 1H, J=2.0 Hz), 7.34 (m, 2H), 7.48-7.52 (m, 1H), 7.59 (t, 1H, J=7.0 Hz), 7.96 (s, 1H), 8.08 (t, 1H, J=7.0 Hz), 8.27 (dd, 1H, J1=7.8 Hz, J2=1.6 Hz), 8.74 (d, 1H, J=6.7 Hz).

Example 16

1-(3,5-Difluoro-benzyl)-3-(2-nitro-phenylsulfanyl)-1H-indol-6-ylamine (Compound 57, Structure 23 of Scheme V, where R$^1$=3,5-difluorophenyl, R$^2$=2-nitrophenyl, R$^3$=R$^4$=H)

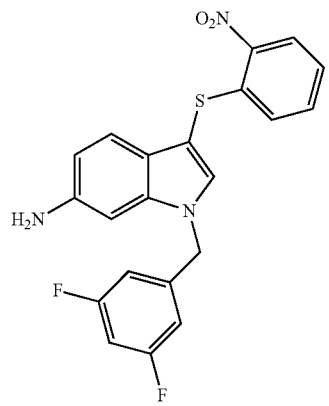

a) 1-(3,5-Difluoro-benzyl)-6-nitro-1H-indole (Structure 19 of Scheme V, where R$^1$=3,5-difluorophenyl, R$^3$=R$^4$=H)

To a solution of 6-nitroindole (162 mg, 1.0 mmol) in DMF (4 mL) was added NaH (60% dispersion on oil; 80 mg, 2.0 mmol). The resulting dark solution was stirred at room temperature for 15 minutes. 3,5-difluorobenzyl bromide (129 μL, 1.1 mmol) was added. The reaction mixture was stirred overnight, poured into acidified water and extracted twice with ethyl acetate. The combined organic layers were dried over Na$_2$SO$_4$ and concentrated in vacuo.

The product was purified over a SiO$_2$ column (heptane/ethyl acetate 9:1) to give the title compound as a yellow solid (270 mg, yield=94%).

LCMS: 5.54 min (100.0%, MH$^+$=289); $^1$H NMR (CDCl$_3$): δ 5.40 (s, 2H, CH$_2$Ar), 6.58 (m, 2H), 6.71 (d, 1H, J=3.5 Hz), 6.75 (m, 1H), 7.26 (s, 1H), 7.41 (d, 1H, J=3.5 Hz), 7.71 (d, 1H, J=8.3 Hz), 8.05 (dd, 1H, J1=8.3 Hz, J2=2.0 Hz), 8.21 (d, 1H, J=2.0 Hz).

b) 1-(3,5-Difluoro-benzyl)-1H-indol-6-ylamine (Structure 20 of Scheme V, where R$^1$=3,5-difluorophenyl, R$^3$=R$^4$=H)

To a solution of 1-(3,5-Difluoro-benzyl)-6-nitro-1H-indole (144 mg, 0.5 mmol) in ethanol (20 mL) was added hydrochloric acid 37% (80 μL) and SnCl$_2$.2H$_2$O (600 mg). The reaction mixture was stirred at 60° C. for 40 h and was then concentrated in vacuo. The residue was poured into ethyl acetate and a concentrated NaHCO$_3$-solution was added. The two-layer phase system was filtered over decalite to get rid of the tin salts and the filtrate was twice extracted with ethyl acetate. The combined organic layers were dried over Na$_2$SO$_4$ and concentrated in vacuo. The product was purified over a SiO$_2$ column (heptane/ethyl acetate 9:1) to give the title compound as a colourless oil (89 mg, yield=69%).

LCMS: 3.20 min (97.7%, MH$^+$=259); $^1$H NMR (CDCl$_3$): δ 5.12 (s, 2H, CH$_2$Ar), 6.52 (m, 2H), 6.56 (d, 1H, J=3.5 Hz), 6.63 (m, 1H), 7.97 (dd, 1H, J1=8.3 Hz, J2=2.0 Hz), 7.13 (d, 1H, J=3.5 Hz), 7.17 (d, 1H, J=2.0 Hz), 7.55 (d, 1H, J=8.3 Hz).

c) 1-(3,5-Difluoro-benzyl)-3-(2-nitro-phenylsulfanyl)-1H-indol-6-ylamine (Compound 57, Structure 23 of Scheme V, where R$^1$=3,5-difluorophenyl, R$^2$=2-nitrophenyl, R$^3$=R$^4$=H)

To a solution of 1-(3,5-Difluoro-benzyl)-1H-indol-6-ylamine (25 mg, 0.1 mmol) in DCM (4 mL) was added 2-nitrobenzenesulfenyl chloride. The resulting yellow solution was stirred at room temperature for 1 hour. The mixture was concentrated in vacuo and purified over a SiO$_2$ column (heptane/ethyl acetate 9:1) to give the title compound as an orange solid (11.6 mg, yield=28%).

LCMS: 5.11 min (100.0%, MH$^+$=412); $^1$H NMR (CDCl$_3$): δ 5.22 (s, 2H, CH$_2$Ar), 6.56 (m, 2H), 6.65 (m, 1H), 6.84 (dd, 1H, J1=8.2 Hz, J2=1.2 Hz), 7.00 (dd, 1H, J1=8.2 Hz, J2=1.2 Hz), 7.19 (m, 1H), 7.30 (d, 1H, J=1.2 Hz), 7.31 (s, 1H), 7.37 (d, 1H, J=8.2 Hz) 7.49 (m, 1H), 8.27 (dd, 1H, J1=8.2 Hz, J2=1.2 Hz).

Example 17

N-[1-(3,5-Difluoro-benzyl)-3-(2-nitro-phenylsulfanyl)-1H-indol-6-yl]-acetamide (Compound 58, Structure 22 of Scheme V, where R$^1$=3,5-difluorophenyl, R$^2$=2-nitrophenyl, R$^3$=R$^4$=H, Z=methyl)

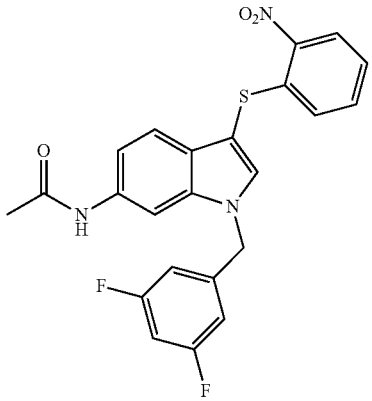

General method 5: Reaction of an acid anhydride with a 6-aminoindole of structure 20 to give compounds of structure 21, followed by sulfonylation of the indole 3-position to give compounds of structure 22 (Scheme V).

a) N-[1-(3,5-Difluoro-benzyl)-1H-indol-6-yl]-acetamide (Structure 21 of Scheme V, where R$^1$=3,5-difluorophenyl, R$^3$=R$^4$=H, Z=methyl)

To a solution of 1-(3,5-Difluoro-benzyl)-1H-indol-6-ylamine (25 mg, 0.1 mmol) in DCM (4 mL) was added pyridine (25 μL) and acetic anhydride (9.8 μL, 0.11 mmol) and stirred overnight at room temperature. The reaction mixture was poured into 10 mL of water and neutralised with NaHCO$_3$ and extracted twice with DCM. De combined organic layers were dried over Na$_2$SO$_4$ and concentrated in vacuo to give the crude compound as a off white solid (23.3 mg, yield=84%). The product was used without further purification.

LCMS: 4.10 min (97.4%, MH$^+$=301); $^1$H NMR (CDCl$_3$): δ 2.18 (s, 3H, CH$_3$CON), 5.28 (s, 2H, CH$_2$Ar), 6.53 (d, 1H, J=3.1), 6.58 (m, 2H), 6.68 (m, 1H), 6.87 (dd, 1H, J1=8.3 Hz, J2=1.6 Hz), 7.07 (d, 1H, J=3.1 Hz), 7.55 (d, 1H, J=8.3 Hz), 7.90 (s, 1H).

b) N-[1-(3,5-Difluoro-benzyl)-3-(2-nitro-phenylsulfanyl)-1H-indol-6-yl]-acetamide (Compound 58, Structure 22 of Scheme V, where R$^1$=3,5-difluorophenyl, R$^2$=2-nitrophenyl, R$^3$=R$^4$=H, Z=methyl)

To a solution of N-[1-(3,5-Difluoro-benzyl)-1H-indol-6-yl]-acetamide (23.3 mg, 0.08 mmol) in diethyl ether (4 mL) was added 2-nitrobenzenesulfenyl chloride (14.7 mg, 0.09 mmol). The resulting yellow solution was stirred overnight at room temperature. The mixture was concentrated in vacuo and purified over a SiO$_2$ column (heptane/ethyl acetate 9:1) to give the title compound as a yellow solid (35.0 mg, yield=96%).

LCMS: 4.26 min (98.6%, MH$^+$=454); $^1$H NMR (DMSO): δ 2.03 (s, 3H, CH$_3$CON), 5.51 (s, 2H, CH$_2$Ar), 6.89 (dd, 1H, J=8.3 Hz, J2=1.2 Hz), 6.95 (m, 2H), 7.17 (dd, 1H, J1=8.3 Hz, J2=2.0 Hz), 7.19 (d, 1H, J=8.3 Hz), 7.34 (m, 1H), 7.49 (m, 1H), 7.97 (d, 1H, J=1.2 Hz), 8.02 (s, 1H), 8.27 (dd, 1H, J1=8.3 Hz, J2=1.2 Hz).

Example 18

N-[1-(3,5-Difluoro-benzyl)-3-(2-nitro-phenylsulfanyl)-1H-indol-6-yl]-2,2,2-trifluoro-acetamide (Compound 59, Structure 22 of Scheme V, where R$^1$=3,5-difluorophenyl, R$^2$=2-nitrophenyl, R$^3$=R$^4$=H, Z=trifluoromethyl)

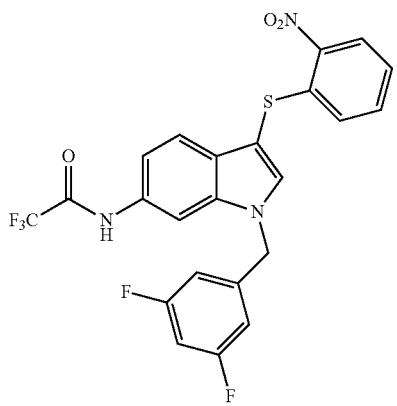

According to General method 5, step a); N-[1-(3,5-Difluoro-benzyl)-1H-indol-6-yl]-2,2,2-trifluoro-acetamide was prepared using 1-(3,5-Difluoro-benzyl)-1H-indol-6-ylamine (17.7 mg, 69 μmol), pyridine (17 μL) and trifluoroacetic anhydride (9.68 μL, 70 μmol). The compound was purified over a SiO$_2$ column (heptane/ethyl acetate 9:1) to give the title compound as a white solid (10.9 mg, yield=61%).

LCMS: 4.41 min (82.1%, MH$^+$=355)

According to General method 5, step b): N-[1-(3,5-Difluoro-benzyl)-3-(2-nitro-phenylsulfanyl)-1H-indol-6-yl]-2,2,2-trifluoro-acetamide was prepared using N-[1-(3,5-Difluoro-benzyl)-1H-indol-6-yl]-2,2,2-trifluoro-acetamide (10.9 mg, 31 μmol) and 2-nitrobenzenesulfenyl chloride (5.7 mg, 37 μmol). The compound was purified over an HPLC column (MeCN/H$_2$O) to give the title compound as a yellow solid (10.2 mg, yield=65%).

LCMS: 4.65 min (89.0%, MH$^+$=508); $^1$H NMR (DMSO): δ 5.56 (s, 2H, CH$_2$Ar), 6.87 (dd, 1H, J=8.3 Hz, J2=1.2 Hz), 7.01 (m, 2H), 7.20 (m, 1H), 7.35 (m, 1H), 7.37 (dd, 1H, J1=8.3 Hz, J2=2.0 Hz), 7.39 (d, 1H, J=8.3 Hz), 7.49 (m, 1H), 7.50 (d, 1H, J=2.0 Hz), 8.15 (s, 1H), 8.28 (dd, 1H, J1=8.3 Hz, J2=2.0 Hz).

Example 19

Compound 97: N-[1-(3,5-Difluoro-benzyl)-3-(2-nitro-phenylsulfanyl)-1H-indol-6-yl]-2-fluoro-acetamide, Structure 28 of Scheme VII, where R$^1$=3,5-difluorophenyl, R$^2$=2-nitrophenyl, R$^3$=R$^4$=H, Z$^1$=monofluoromethyl

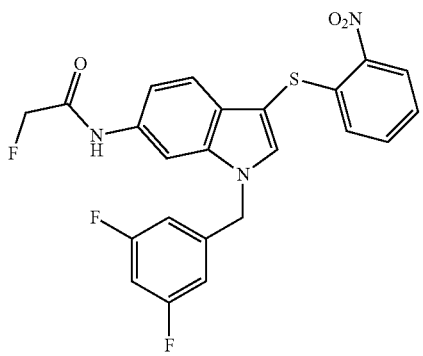

a) 1-(3,5-Difluoro-benzyl)-6-nitro-1H-indole, Structure 19 of Scheme VII, where R$^1$=3,5-difluorophenyl, R$^2$=R$^3$=R$^4$=H To a solution of 6-nitro-1H-indole (19.5 g, 120 mmol) in NMP (500 mL) was added at 0° C. cesium carbonate (39.1 g, 120 mmol). After stirring for 30 min at 0° C. 3,5-difluorobenzyl bromide (30.0 g, 144 mmol) was added and the mixture was allowed to warm to room temperature and stirred for 18 hrs. The mixture was poured into saturated aqueous ammonium chloride (1 L) and extracted with ethyl acetate (2×500 mL). The combined organic layers were washed with H$_2$O (2×500 mL) and brine (500 mL) and dried (Na$_2$SO$_4$) and concentrated to give the title compound (65 g, yellow solid) which was used without further purification.

b) 1-(3,5-Difluoro-benzyl)-1H-indol-6-ylamine, Structure 20 of Scheme VII, where R$^1$=3,5-difluorophenyl, R$^2$=R$^3$=R$^4$=H EtOH 96% (1 L) was added to 1-(3,5-difluoro-benzyl)-6-nitro-1H-indole and the mixture was stirred at 60° C. until all material was dissolved. 37% HCl (37 mL) was added followed by tin(II)chloride dihydrate (268 g, 1.19 mol) and stirring was continued at 60° C. for 18 hrs. After the mixture was cooled to room temperature the solvent was removed under reduced pressure. Ethyl acetate (800 mL) was added and the mixture was poured into saturated aqueous NaHCO$_3$ (1 L) and filtered over kieselguhr. The layers were separated and the organic layer was washed with H$_2$O (2×500 mL) and brine (500 mL), dried (Na$_2$SO$_4$) and concentrated to afford the the title compound (54 g, brown oil/solid) which was used without further purification.

c) [1-(3,5-Difluoro-benzyl)-1H-indol-6-yl]-carbamic acid tert-butyl ester, Structure 26 of Scheme VII, where R$^1$=3,5-difluorophenyl, R$^2$=R$^3$=R$^4$=H 1-(3,5-Difluoro-benzyl)-1H-indol-6-ylamine was dissolved in NMP (1 L) and triethylamine (34 mL, 242 mmol) was added followed by di-tert-butyl dicarbonate (53 g, 242 mmol) and the mixture was stirred at room temperature for 18 hrs. The mixture was poured into saturated aqueous NaHCO$_3$ (1.5 L) and extracted with ethyl acetate (3×750 mL). The combined organic layers were washed with H$_2$O (1 L) and brine (1 L), dried (Na$_2$SO$_4$) and concentrated. The crude product was purified using column chromatography (heptane/ethyl acetate 4:1) to afford the title compound (39 g, 109 mmol, 91% (three steps), white solid).

d) [1-(3,5-Difluoro-benzyl)-3-(2-nitro-phenylsulfanyl)-1H-indol-6-yl]-carbamic acid tert-butyl ester, Structure 27 of Scheme VII, where R$^1$=3,5-difluorophenyl, R$^2$=2-nitrophenyl, R$^3$=R$^4$=H To a solution of [1-(3,5-difluoro-benzyl)-1H-indol-6-yl]-carbamic acid tert-butyl ester (39 g, 109 mmol) in diethylether (750 mL) was added 2-nitrobenzenesulfenyl chloride (20.4 g, 109 mmol) and the reaction mixture was stirred at room temperature for 18 hrs. The mixture was poured into saturated aqueous NaHCO$_3$ (1 L) and extracted with ethyl acetate (2×300 mL). The combined organic layers were washed with H$_2$O (400 ml) and brine (400 mL), dried and concentrated to afford the title compound (56 g, yellow solid) which was used without further purification.

e) 1-(3,5-Difluoro-benzyl)-3-(2-nitro-phenylsulfanyl)-1H-indol-6-ylamine, Structure 23 of Scheme VII, where R$^1$=3,5-difluorophenyl, R$^2$=2-nitrophenyl, R$^3$=R$^4$=H

[1-(3,5-Difluoro-benzyl)-3-(2-nitro-phenylsulfanyl)-1H-indol-6-yl]-carbamic acid tert-butyl ester was dissolved in CH$_2$Cl$_2$ (1 L) and under nitrogen atmosphere trifluoroacetic acid (48 mL, 624 mmol) was added dropwise at room temperature. After stirring for 1 h another portion of trifluoroacetic acid (48 mL, 624 mmol) was added and the reaction mixture was stirred for an additional hour. The mixture was diluted with CH$_2$Cl$_2$ (500 mL) and H$_2$O (1 L) and 3N NaOH solution was added until the pH of the mixture was 11-12. The layers were separated and the organic layer was washed with H$_2$O (500 mL) and brine (500 mL), dried (Na$_2$SO$_4$) and concentrated to afford the crude product. The product was purified using column chromatography (heptane/ethylacetate 1:1) to give the title compound (28 g, 68 mmol, 63% (two steps), red/brown solid).

General method 6: Reaction of an acid chloride (method a), carboxylic acid (method b) or sulfonyl chloride (method c) with a 6-aminoindole of structure 23 to give compounds of structure 28 and 29 (Scheme VII).

Method a, b and c can all be carried out using the same procedure which is exemplified below for method a.

To a solution of 1-(3,5-difluoro-benzyl)-3-(2-nitro-phenylsulfanyl)-1H-indol-6-ylamine (300 mg, 0.73 mmol) in CH$_2$Cl$_2$ (7 mL) was added at 0° C. triethylamine (0.12 mL, 0.87 mmol). Subsequently monofluroacetyl chloride (50 μL, 0.73 mmol) was added and the mixture was stirred at room temperature for 18 hrs. The mixture was concentrated and purified using flash column chromatography (CH$_2$Cl$_2$/MeOH 99:1) to afford compound 97 (317 mg, 0.67 mmol, 92%, yellow solid).

$^1$H NMR (DMSO) δ 4.82 (s, 1H), 5.03 (s, 1H), 5.52 (s, 2H), 6.89 (dd, 1H, J1=7.6 Hz, J2=1.1 Hz), 6.98-7.01 (m, 2H), 7.20 (tt, 1H, J1=9.5 Hz, J2=3.0 Hz), 7.28-7.32 (m, 2H), 7.33-7.37 (m, 1H), 7.46-7.51 (m, 1H), 7.98 (s, 1H), 8.08 (s, 1H), 8.27 (dd, 1H, J1=7.6 Hz, J2=1.1 Hz), 10.15 (s, 1H).

According to general method 6 the following compounds were prepared:

Compound 98: N-[1-(3,5-Difluoro-benzyl)-3-(2-nitro-phenylsulfanyl)-1H-indol-6-yl]-2,2-difluoro-acetamide, structure 28 of Scheme VII, where R$^1$ = 3,5-difluorophenyl, R$^2$ = 2-nitrophenyl, R$^3$ = R$^4$ = H, Z$^1$ = difluoromethyl. Method a was used.

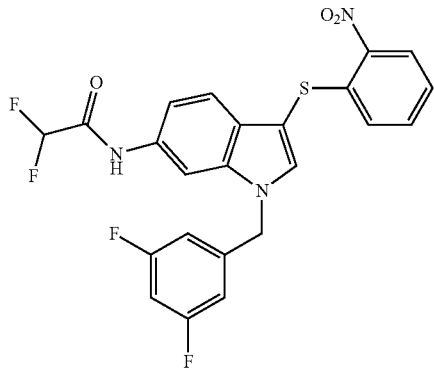

$^1$H-NMR (DMSO): δ 5.55 (s, 2H), 6.23-6.50 (m, 1H), 6.88 (dd, 1H, J1 = 7.6 Hz, J2 = 1.1 Hz), 6.97-7.03 (m, 2H), 7.20 (tt, 1H, J1 = 9.5 Hz, J2 = 3.0 Hz), 7.30-7.38 (m, 3H), 7.46-7.51 (m, 1H), 7.98 (d, 1H, J1 = 1.1 Hz), 8.12 (s, 1H), 8.28 (dd, 1H, J1 = 7.6 Hz, J2 = 1.1 Hz), 10.80 (s, 1H).

Compound 99: N-[1-(3,5-Difluoro-benzyl)-3-(2-nitro-phenylsulfanyl)-1H-indol-6-yl]-propionamide, structure 28 of Scheme VII, where R$^1$ = 3,5-difluorophenyl, R$^2$ = 2-nitrophenyl, R$^3$ = R$^4$ = H, Z$^1$ = ethyl. Method b was used.

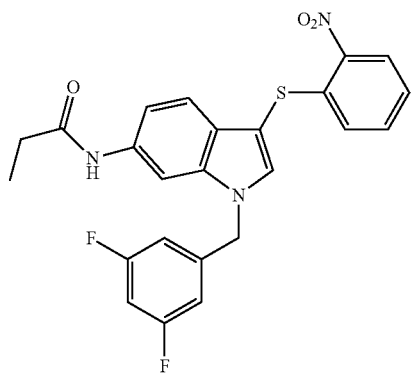

$^1$H-NMR (DMSO): δ 1.07 (t, 3H, J = 7.6 Hz), 2.31 (q, 2H, J = 7.6 Hz), 5.51 (s, 2H), 6.89 (dd, 1H, J1 = 7.6 Hz, J2 = 1.1 Hz), 6.93-6.97 (m, 1H), 7.16-7.23 (m, 3H), 7.27 (d, 1H, J = 8.4 Hz), 7.32-7.37 (m, 1H), 7.46-7.51 (m, 1H), 8.01 (d, 1H, J = 1.1 Hz), 8.02 (s, 1H), 8.27 (dd, 1H, J1 = 7.6 Hz, J2 = 1.1 Hz), 9.92 (s, 1H).

Compound 100: 2-Fluoro-N-[3-(2-nitro-phenylsulfanyl)-1-pyridin-2-ylmethyl-1H-indol-6-yl]-acetamide, structure 28 of Scheme VII, where R$^1$ = 2-pyridyl, R$^2$ = 2-nitrophenyl, R$^3$ = R$^4$ = H, Z$^1$ = monofluoromethyl. Method a was used.

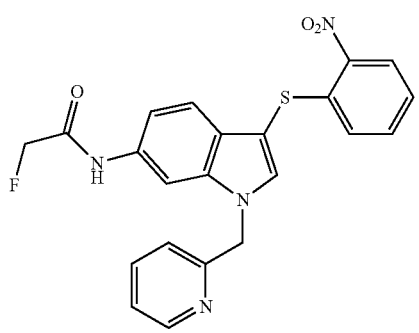

$^1$H-NMR (CDCl$_3$): δ 4.88 (s, 1H), 5.00 (s, 1H), 5.51 (s, 2H), 6.94-6.99 (m, 2H), 7.06 (dd, 1H, J1 = 7.6 Hz, J2 = 1.5 Hz), 7.18 (td, 1H, J1 = 8.4 Hz, J2 = 1.5 Hz), 7.22-7.29 (m, 2H), 7.46 (d, 1H, J = 8.4 Hz), 7.55 (s, 1H), 7.64 (td, 1H, J1 = 8.4 Hz, J2 = 1.5 Hz), 8.02 (s, 1H), 8.05 (d, 1H, J = 2.2 Hz), 8.27 (dd, 1H, J1 = 7.6 Hz, J2 = 1.5 Hz), 8.62 (d, 1H, J = 4.6 Hz).

Compound 101: N-[3-(2-Nitro-phenylsulfanyl]-1-pyridin-2-ylmethyl-1H-indol-6-yl]-
acetamide, structure 28 of Scheme VII, where R¹ = 2-pyridyl, R² = 2-nitrophenyl,
R³ = R⁴ = H, Z¹ = methyl. Method a was used.

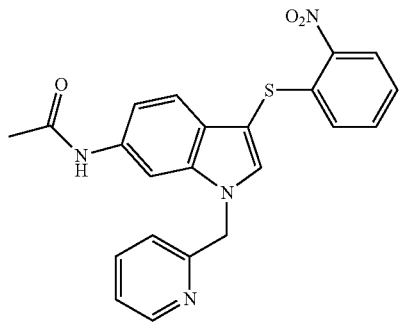

¹H-NMR (CDCl₃): δ 1.80 (s, 3H), 5.48 (s, 2H), 6.92-6.98 (m, 3H), 7.15-7.30 (m, 4H), 7.40 (d, 1H, J = 7.6 Hz), 7.51 (s, 1H), 7.63 (td, 1H, J1 = 7.6 Hz, J2 = 2.2 Hz), 8.04 (d, 1H, J = 1.5 Hz), 8,26 (dd, 1H, J1 = 7.6 Hz, J2 = 1.5 Hz), 8.61 (d, 1H, J = 4.6 Hz).

Compound 102: N-[3-(2-Nitro-phenylsulfanyl)-1-pyridin-2-ylmethyl-1H-indol-6-yl]-
propionamide, structure 28 of Scheme VII, where R¹ = 2-pyridyl, R² = 2-nitrophenyl,
R³ = R⁴ = H, Z¹ = methyl. Method b was used.

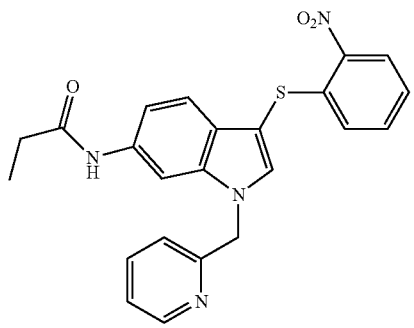

¹H-NMR (CDCl₃): δ 1.25 (t, 3H, J = 7.6 Hz), 2.41 (q, 2H, J = 7.6 Hz), 5.49 (s, 2H), 6.92-6.98 (m, 3H), 7.15-7.27 (m, 4H), 7.40 (d, 1H, J = 8.4 Hz), 7.51 (s, 1H), 7.63 (td, 1H, J1 = 7.6 Hz, J2 = 1.5 Hz), 8.12 (d, 1H, J = 1.5 Hz), 8.26 (dd, 1H, J1 = 7.6 Hz, J2 = 1.5 Hz), 8.61 (d, 1H, J = 4.6 Hz).

Compound 103: N-[3-(2-Nitro-phenylsulfanyl)-1-pyridin-3-ylmethyl-1H-indol-6-yl]-
acetamide, structure 28 of Scheme VII, where R¹ = 3-pyridyl, R² = 2-nitrophenyl,
R³ = R⁴ = H, Z¹ = methyl. Method a was used.

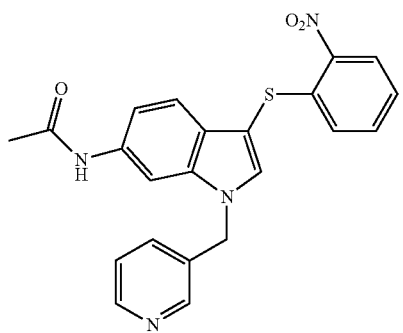

¹H-NMR (CDCl₃): δ 2.20 (s, 3H), 5.40 (s, 2H), 6.86 (dd, 1H, J1 = 7.6 Hz, J2 = 2.2 Hz), 6.72 (dd, 1H, J1 = 7.6 Hz, J2 = 1.1 Hz), 7.16-7.20 (m, 1H), 7.24-7.31 (m, 3H), 7.40 (d, 1H, J = 8.4 Hz), 7.42 (s, 1H), 7.49-7.52 (m, 1H), 8.15 (d, 1H, J = 2.2 Hz), 8.26 (dd, 1H, J1 = 8.4 Hz, J2 = 2.2 Hz), 8.55 (d, 1H, J = 3.0 Hz), 8.58 (dd, 1H, J1 = 8.4 Hz, J2 = 2.2 Hz).

Compound 104: 2-Fluoro-N-[3-(2-nitro-phenylsulfanyl)-1-pyridin-3-ylmethyl-1H-indol-6-yl]-acetamide, structure 28 of Scheme VII, where $R^1$ = 3-pyridyl, $R^2$ = 2-nitrophenyl, $R^3$ = $R^4$ = H, $Z^1$ = monofluoromethyl. Method a was used.

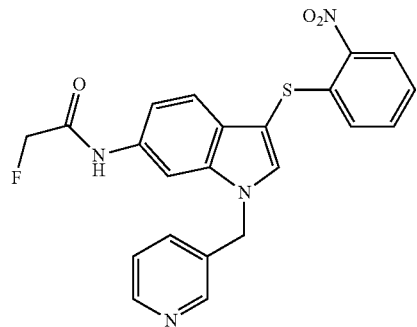

$^1$H-NMR (CDCl$_3$): δ 4.88 (s, 1H), 5.00 (s, 1H), 5.42 (s, 2H), 6.92 (dd, 1H, J1 = 7.6 Hz, J2 = 1.1 Hz), 7.00 (dd, 1H, J1 = 8.4 Hz, J2 = 1.8 Hz), 7.17-7.21 (m, 1H), 7.25-7.32 (m, 2H), 7.44-7.47 (d, 1H, J = 7.6 Hz), 7.45 (s, 1H), 7.49-7.53 (m, 1H), 8.04 (d, 1H, J = 4.6 Hz), 8.15 (d, 1H, J = 1.8 Hz), 8.27 (dd, 1H, J1 = 8.4 Hz, J2 = 1.8 Hz), 8.56 (d, 1H, J = 3.0 Hz), 8.58 (dd, 1H, J1 = 4.6 Hz, J2 = 1.2 Hz).

Compound 105: N-[3-(2-Nitro-phenylsulfany)-1-pyridin-3-ylmethyl-1H-indol-6-yl]-propionamide, structure 28 of Scheme VII, where $R^1$ = 3-pyridyl, $R^2$ = 2-nitrophenyl, $R^3$ = $R^4$ = H, $Z^1$ = methyl. Method b was used.

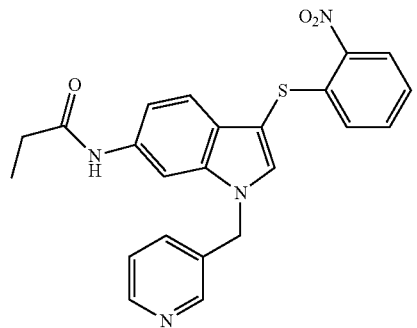

$^1$H-NMR (CDCl$_3$): δ 1.26 (t, 3H, J = 7.6 Hz), 2.42 (q, 2H, J = 7.6 Hz), 5.39 (s, 2H), 8.68 (dd, 1H, J1 = 8.4 Hz, J2 = 1.8 Hz), 6.91 (dd, 1H, J1 = 8.4 Hz, J2 = 1.1 Hz), 7.15-7.20 (m, 1H), 7.24-7.30 (m, 3H), 7.38-7.41 (m, 2H), 7.48-7.52 (m, 1H), 8.23 (d, 1H, J = 1.8 Hz), 8.27 (dd, 1H, J1 = 8.4 Hz, J2 = 1.8 Hz), 8.55 (d, 1H, J = 3.0 Hz), 8.57 (dd, 1H, J1 = 4.6 Hz, J2 = 1.1 Hz).

Compound 106: N-[1-(3,5-Difluoro-benzyl)-3-(2-nitro-phenylsulfanyl)-1H-indol-6-yl]-methanesulfonamide, structure 29 of Scheme VII, where $R^1$ = 3,5-difluorophenyl, $R^2$ = 2-nitrophenyl, $R^3$ = $R^4$ = H, $Z^2$ = Me. Method c was used.

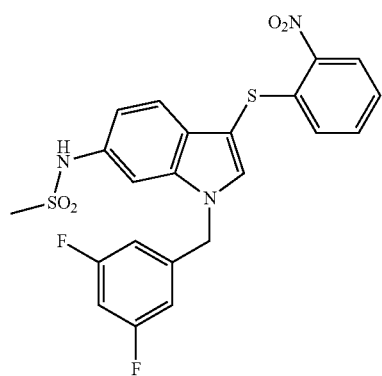

$^1$H-NMR (DMSO): δ 2.95 (s, 3H), 5.54 (s, 2H), 6.90 (dd, 1H, J1 = 7.6 Hz, J2 = 1.1 Hz), 6.98-7.04 (m, 3H), 7.20 (tt, 1H, J1 = 9.5 Hz, J2 = 3.0 Hz), 7.31-7.37 (m, 2H), 7.41 (d, 1H, J = 1.5 Hz), 7.47-7.52 (m, 1H), 8.08 (s, 1H), 8.27 (dd, 1H, J1 = 7.6 Hz, J2 = 1.1 Hz), 9.65 (s, 1H).

Compound 107: Thiophene-3-sulfonic acid [1-(3,5-difluoro-benzyl)-3-(2-nitro-phenylsulfanyl)-1H-indol-6-yl]-amide, structure 29 of Scheme VII, where $R^1$ = 3,5-difluorophenyl, $R^2$ = 2-nitrophenyl, $R^3$ = $R^4$ = H, $Z^1$ = 3-thiophene. Method c was used.

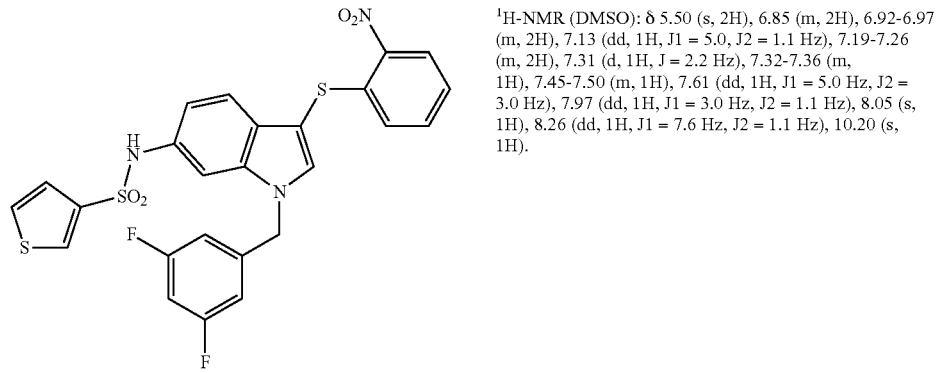

$^1$H-NMR (DMSO): δ 5.50 (s, 2H), 6.85 (m, 2H), 6.92-6.97 (m, 2H), 7.13 (dd, 1H, J1 = 5.0, J2 = 1.1 Hz), 7.19-7.26 (m, 2H), 7.31 (d, 1H, J = 2.2 Hz), 7.32-7.36 (m, 1H), 7.45-7.50 (m, 1H), 7.61 (dd, 1H, J1 = 5.0 Hz, J2 = 3.0 Hz), 7.97 (dd, 1H, J1 = 3.0 Hz, J2 = 1.1 Hz), 8.05 (s, 1H), 8.26 (dd, 1H, J1 = 7.6 Hz, J2 = 1.1 Hz), 10.20 (s, 1H).

Compound 108: 1-Methyl-1H-imidazole-4-sulfonic acid [1-(3,5-difluoro-benzyl)-3-(2-nitro-phenylsulfanyl)-1H-indol-6-yl]-amide, structure 29 of Scheme VII, where $R^1$ = 3,5-difluorophenyl, $R^2$ = 2-nitrophenyl, $R^3$ = $R^4$ = H, $Z^2$ = 4-(1-methyl-imidazole). Method c was used.

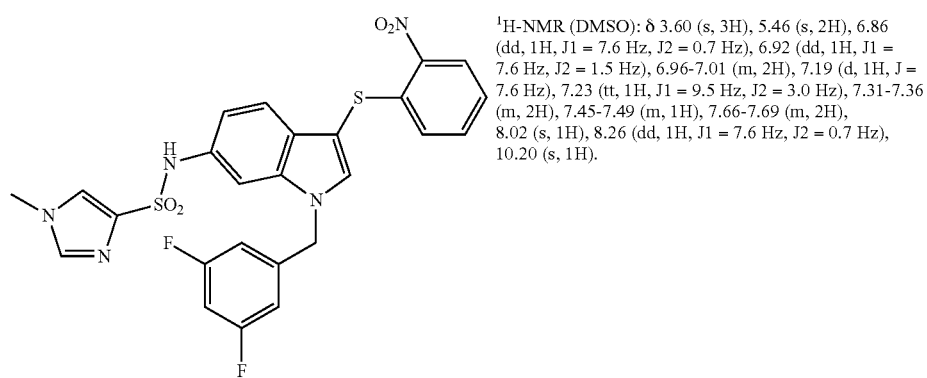

$^1$H-NMR (DMSO): δ 3.60 (s, 3H), 5.46 (s, 2H), 6.86 (dd, 1H, J1 = 7.6 Hz, J2 = 0.7 Hz), 6.92 (dd, 1H, J1 = 7.6 Hz, J2 = 1.5 Hz), 6.96-7.01 (m, 2H), 7.19 (d, 1H, J = 7.6 Hz), 7.23 (tt, 1H, J1 = 9.5 Hz, J2 = 3.0 Hz), 7.31-7.36 (m, 2H), 7.45-7.49 (m, 1H), 7.66-7.69 (m, 2H), 8.02 (s, 1H), 8.26 (dd, 1H, J1 = 7.6 Hz, J2 = 0.7 Hz), 10.20 (s, 1H).

40

Example 20

According to general method 3 the following compounds were prepared:

Compound 93: 6-Methoxy-3-(2-nitro-phenylsulfanyl)-1-pyridin-4-ylmethyl-1H-indole, structure 3 of scheme I, where $R^1$ = 4-pyridyl, $R^2$ = 2-nitrophenyl, $R^3$ = $R^4$ = H, $R^5$ = OMe. NaH and DMF were used.

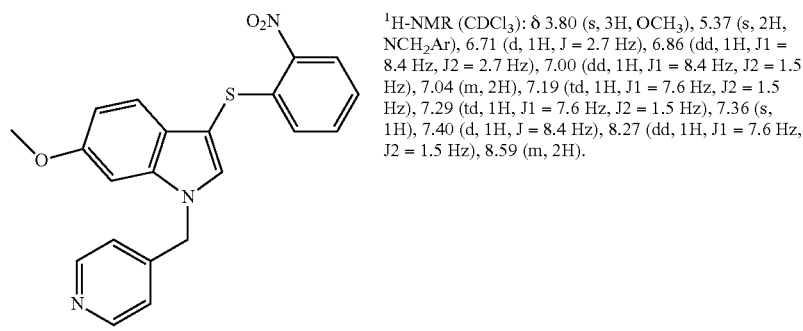

$^1$H-NMR (CDCl$_3$): δ 3.80 (s, 3H, OCH$_3$), 5.37 (s, 2H, NCH$_2$Ar), 6.71 (d, 1H, J = 2.7 Hz), 6.86 (dd, 1H, J1 = 8.4 Hz, J2 = 2.7 Hz), 7.00 (dd, 1H, J1 = 8.4 Hz, J2 = 1.5 Hz), 7.04 (m, 2H), 7.19 (td, 1H, J1 = 7.6 Hz, J2 = 1.5 Hz), 7.29 (td, 1H, J1 = 7.6 Hz, J2 = 1.5 Hz), 7.36 (s, 1H), 7.40 (d, 1H, J = 8.4 Hz), 8.27 (dd, 1H, J1 = 7.6 Hz, J2 = 1.5 Hz), 8.59 (m, 2H).

Compound 94: 6-Methoxy-3-(2-nitro-phenylsulfanyl)-1-(3,4,5-trifluoro-benzyl)-1H-indole, structure 3 of scheme I, where $R^1$ = 3,4,5-difluorophenyl, $R^2$ = 2-nitrophenyl, $R^3 = R^4$ = H, $R^5$ = OMe. $Cs_2CO_3$ and NMP were used.

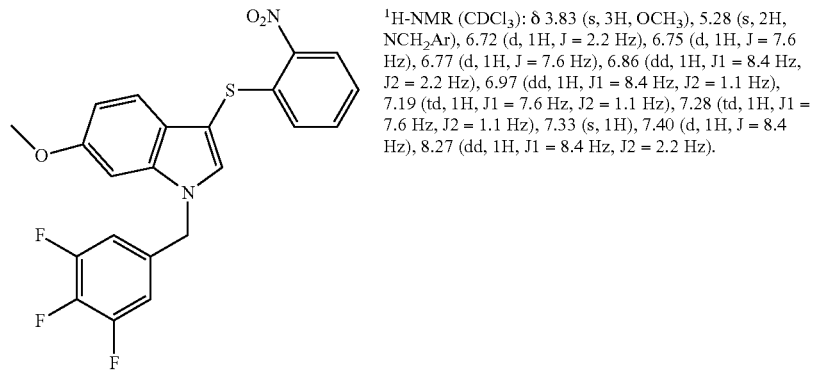

$^1$H-NMR (CDCl$_3$): δ 3.83 (s, 3H, OCH$_3$), 5.28 (s, 2H, NCH$_2$Ar), 6.72 (d, 1H, J = 2.2 Hz), 6.75 (d, 1H, J = 7.6 Hz), 6.77 (d, 1H, J = 7.6 Hz), 6.86 (dd, 1H, J1 = 8.4 Hz, J2 = 2.2 Hz), 6.97 (dd, 1H, J1 = 8.4 Hz, J2 = 1.1 Hz), 7.19 (td, 1H, J1 = 7.6 Hz, J2 = 1.1 Hz), 7.28 (td, 1H, J1 = 7.6 Hz, J2 = 1.1 Hz), 7.33 (s, 1H), 7.40 (d, 1H, J = 8.4 Hz), 8.27 (dd, 1H, J1 = 8.4 Hz, J2 = 2.2 Hz).

Compound 95: 6-Methoxy-3-(2-nitro-phenylsulfanyl)-1-(2,3,5-trifluoro-benzyl)-1H-indole, structure 3 of scheme I, where $R^1$ = 2,3,5-difluorophenyl, $R^2$ = 2-nitrophenyl, $R^3 = R^4$ = H, $R^2$ = OMe. $Cs_2CO_3$ and NMP were used.

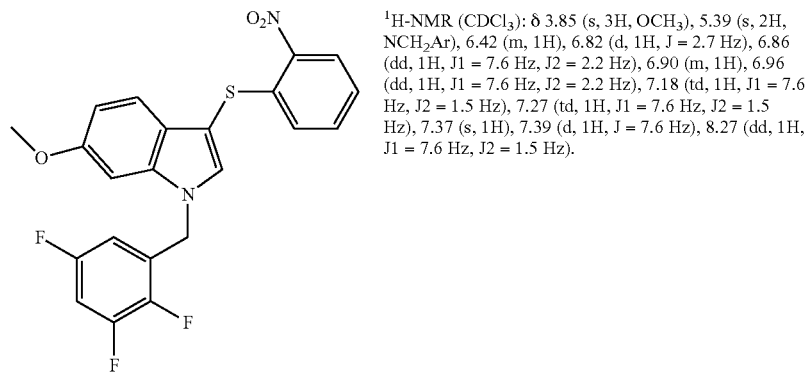

$^1$H-NMR (CDCl$_3$): δ 3.85 (s, 3H, OCH$_3$), 5.39 (s, 2H, NCH$_2$Ar), 6.42 (m, 1H), 6.82 (d, 1H, J = 2.7 Hz), 6.86 (dd, 1H, J1 = 7.6 Hz, J2 = 2.2 Hz), 6.90 (m, 1H), 6.96 (dd, 1H, J1 = 7.6 Hz, J2 = 2.2 Hz), 7.18 (td, 1H, J1 = 7.6 Hz, J2 = 1.5 Hz), 7.27 (td, 1H, J1 = 7.6 Hz, J2 = 1.5 Hz), 7.37 (s, 1H), 7.39 (d, 1H, J = 7.6 Hz), 8.27 (dd, 1H, J1 = 7.6 Hz, J2 = 1.5 Hz).

Compound 96: 1-(6-Chloro-pyridin-3-ylmethyl)-6-methoxy-3-(2-nitro-phenylsulfanyl)-1H-indole, structure 3 of Scheme I, where $R^1$ = 4-chloro-3-pyridyl, $R^2$ = 2-nitrophenyl, $R^3 = R^4$ = H, $R^5$ = OMe). $Cs_2CO_3$ and NMP were used.

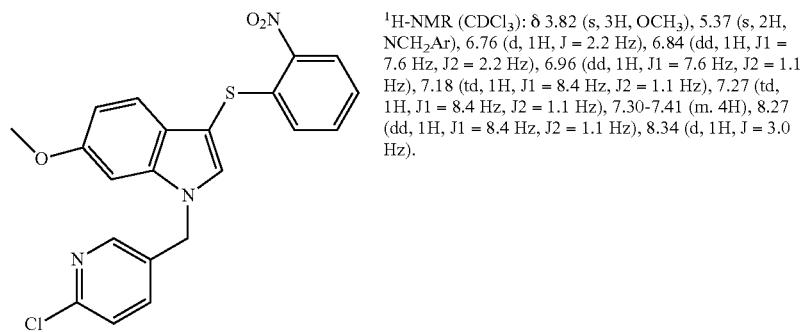

$^1$H-NMR (CDCl$_3$): δ 3.82 (s, 3H, OCH$_3$), 5.37 (s, 2H, NCH$_2$Ar), 6.76 (d, 1H, J = 2.2 Hz), 6.84 (dd, 1H, J1 = 7.6 Hz, J2 = 2.2 Hz), 6.96 (dd, 1H, J1 = 7.6 Hz, J2 = 1.1 Hz), 7.18 (td, 1H, J1 = 8.4 Hz, J2 = 1.1 Hz), 7.27 (td, 1H, J1 = 8.4 Hz, J2 = 1.1 Hz), 7.30-7.41 (m, 4H), 8.27 (dd, 1H, J1 = 8.4 Hz, J2 = 1.1 Hz), 8.34 (d, 1H, J = 3.0 Hz).

Compound 115: 6-Methoxy-3-(2-nitro-phenylsulfanyl)-1-pyrimidin-5-ylmethyl-1H-indole, structure 3 of Scheme I, where $R^1$ = 3,5-pyrimidyl, $R^2$ = 2-nitrophenyl, $R^3 = R^4$ = H, $R^1$ = OMe. NaH and DMF were used. The synthesis of methanesulfonic acid pyrimidin-5-ylmethyl ester is described in example 23a).

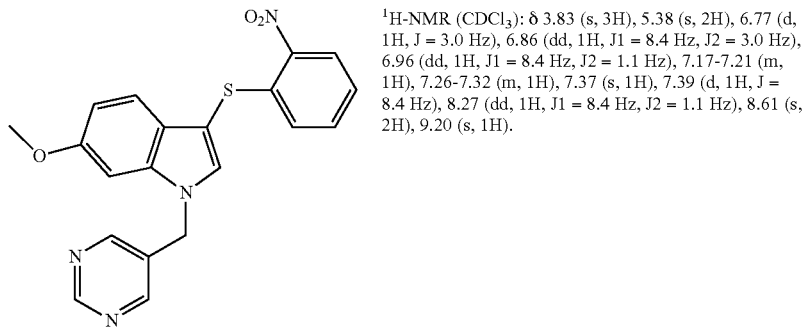

$^1$H-NMR (CDCl$_3$): δ 3.83 (s, 3H), 5.38 (s, 2H), 6.77 (d, 1H, J = 3.0 Hz), 6.86 (dd, 1H, J1 = 8.4 Hz, J2 = 3.0 Hz), 6.96 (dd, 1H, J1 = 8.4 Hz, J2 = 1.1 Hz), 7.17-7.21 (m, 1H), 7.26-7.32 (m, 1H), 7.37 (s, 1H), 7.39 (d, 1H, J = 8.4 Hz), 8.27 (dd, 1H, J1 = 8.4 Hz, J2 = 1.1 Hz), 8.61 (s, 2H), 9.20 (s, 1H).

Compound 116: 6-Methoxy-3-(2-nitro-phenylsulfanyl)-1-pyrimidin-4-ylmethyl-1H-indole structure 3 of Scheme I, where $R^1$ = 2,4-pyrimidyl, $R^2$ = 2-nitrophenyl, $R^3 = R^4$ = H, $R^5$ = OMe. Cs$_2$CO$_3$ and NMP were used.

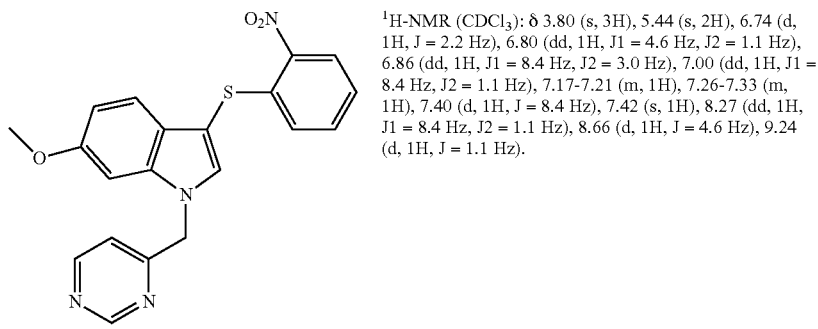

$^1$H-NMR (CDCl$_3$): δ 3.80 (s, 3H), 5.44 (s, 2H), 6.74 (d, 1H, J = 2.2 Hz), 6.80 (dd, 1H, J1 = 4.6 Hz, J2 = 1.1 Hz), 6.86 (dd, 1H, J1 = 8.4 Hz, J2 = 3.0 Hz), 7.00 (dd, 1H, J1 = 8.4 Hz, J2 = 1.1 Hz), 7.17-7.21 (m, 1H), 7.26-7.33 (m, 1H), 7.40 (d, 1H, J = 8.4 Hz), 7.42 (s, 1H), 8.27 (dd, 1H, J1 = 8.4 Hz, J2 = 1.1 Hz), 8.66 (d, 1H, J = 4.6 Hz), 9.24 (d, 1H, J = 1.1 Hz).

Compound 117: 6-Methoxy-3-(2-nitro-phenylsulfanyl)-1-pyrazin-2-ylmethyl-1H-indole, structure 3 of Scheme I, where $R^1$ = 2,5-pyrazyl, $R^2$ = 2-nitrophenyl, $R^3 = R^4$ = H, $R^5$ = OMe. Cs$_2$CO$_3$ and NMP were used.

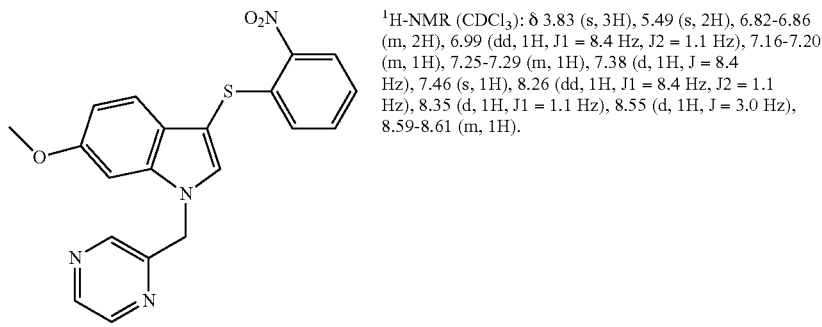

$^1$H-NMR (CDCl$_3$): δ 3.83 (s, 3H), 5.49 (s, 2H), 6.82-6.86 (m, 2H), 6.99 (dd, 1H, J1 = 8.4 Hz, J2 = 1.1 Hz), 7.16-7.20 (m, 1H), 7.25-7.29 (m, 1H), 7.38 (d, 1H, J = 8.4 Hz), 7.46 (s, 1H), 8.26 (dd, 1H, J1 = 8.4 Hz, J2 = 1.1 Hz), 8.35 (d, 1H, J1 = 1.1 Hz), 8.55 (d, 1H, J = 3.0 Hz), 8.59-8.61 (m, 1H).

Compound 61: 1-(3,5-Difluoro-benzyl)-3-(2-nitro-phenylsulfanyl)-1H-indol-6-ol, Structure 25 of Scheme VI, where $R^1$=3,5-difluorophenyl, $R^2$=2-nitrophenyl, $R^3$=$R^4$=H, $R^5$=OH

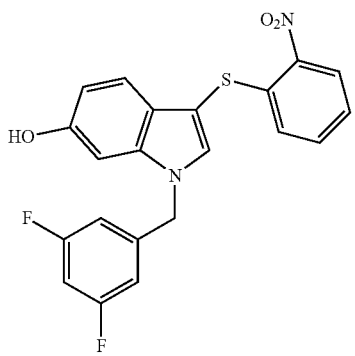

To a solution of compound 63 (240 mg, 0.56 mmol) in $CH_2Cl_2$ (10 mL) was added at 0° C. boron trifluoride-methyl sulfide complex (2.37 mL, 22.5 mmol). After stirring for 2 hrs at 0° C. the reaction mixture was allowed to warm to room temperature and stirring was continued for another 4 hrs. The reaction mixture was poured into ice water (20 mL) and after addition of ethyl acetate (10 mL) the layers were separated. The organic layer was washed with saturated aqueous $NaHCO_3$ (20 mL) and brine (20 mL) and dried over $Na_2SO_4$. Concentration gave the crude product which was purified using flash chromatography (heptane/ethylacetate 3:2) to afford compound 61 as a yellow oil (87 mg, 0.21 mmol, 38%).

$^1$H NMR ($CDCl_3$) δ 4.75 (2, 1H), 5.29 (s, 2H), 4.66 (m, 1H), 6.72-6.79 (m, 3H), 6.98 (dd, 1H, J1=8.4 Hz, J2=1.5 Hz), 7.17-7.21 (m, 1H), 7.27-7.31 (m, 1H), 7.35-7.37 (m, 3H), 8.27 (dd, 1H, J1=8.4 Hz, J2=1.5 Hz).

Example 22

Compound 109: 3-(2-Nitro-phenylsulfanyl)-1-pyridin-2-ylmethyl-1H-indole-6-carboxylic acid dimethylamide, Structure 15 of Scheme IV, where $R^1$=2-pyridyl, $R^2$=2-nitrophenyl, $R^3$=$R^4$=H, $R^8$=$R^9$=Me

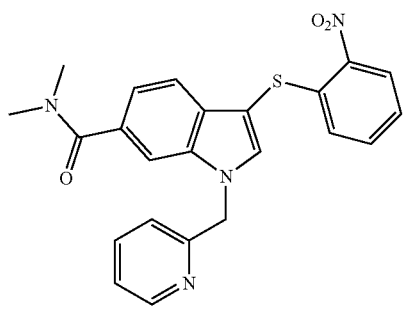

a) 1-Pyridin-2-ylmethyl-1H-indole-6-carboxylic acid methyl ester

Under a nitrogen atmosphere: to a solution of 1H-indole-6-carboxylic acid methyl ester (for synthesis see example 2a), 2.47 g, 14.1 mmol) in NMP (140 mL) was added $Cs_2CO_3$ (10.1 mg, 31 mmol) at 0° C. After stirring for 15 min 2-picolyl chloride hydrochloride (2.77 g, 16.9 mmol) was added and the mixture was stirred at room temperature for 18 h. Ethyl acetate (200 mL) was added and the mixture was washed with saturated aqueous ammonium chloride (3×150 mL) and brine (200 mL). The organic phase was dried ($Na_2SO_4$) and concentrated. The crude product was purified using column chromatography (ethyl acetate/heptane 1:3) to give the title compound as a colourless oil, which slowly crystallised on standing (2.72 g, 10.2 mmol, 72%).

b) 3-(2-Nitro-phenylsulfanyl)-1-pyridin-2-ylmethyl-1H-indole-6-carboxylic acid methyl ester, Structure 13 of Scheme IV, where $R^1$=2-pyridyl, $R^2$=2-nitrophenyl, $R^3$=$R^4$=H To a solution of 1-pyridin-2-ylmethyl-1H-indole-6-carboxylic acid methyl ester (2.72 g, 10.2 mmol) in dichloromethane (75 mL) was added at room temperature a solution of 2-nitrobenzenesulfenyl chloride (1.93 g, 10.2 mmol) in dichloromethane (75 mL). The mixture was stirred at room temperature for 24 hrs. The reaction mixture was concentrated and the crude product was purified using column chromatography (ethyl acetate/heptane 1:5 to 1:2) to give the title compound as a yellow solid (3.21 g, 7.65 mmol, 75%).

c) 3-(2-Nitro-phenylsulfanyl)-1-pyridin-2-ylmethyl-1H-indole-6-carboxylic acid, Structure 14 of Scheme IV, where $R^1$=2-pyridyl, $R^2$=2-nitrophenyl, $R^3$=$R^4$=H To a suspension of 3-(2-nitro-phenylsulfanyl)-1-pyridin-2-ylmethyl-1H-indole-6-carboxylic acid methyl ester (3.0 g, 6.58 mmol) in dioxane (65 mL) was added a solution of $LiOH.H_2O$ (1.66 g, 39.6 mmol) in water (65 mL). The reaction mixture was stirred overnight at 60° C. The mixture was then acidified to pH 6 by addition of 15% aqueous HCl and the mixture was extracted with ethyl acetate (2×100 mL). The combined organic layers were dried over $Na_2SO_4$ and concentrated to give a yellow powder. The product was recrystallised from heptane/ethyl acetate to give the title compound as yellow/orange crystals (2.47 g, 6.09 mmol, 93%)

General method 7: amidation of 6-carboxyl indoles of structure 14 to give 6-carboxamideindoles of structure 15 (Scheme IV).

Under nitrogen atmosphere: to a solution of 3-(2-nitro-phenylsulfanyl)-1-pyridin-2-ylmethyl-1H-indole-6-carboxylic acid (700 mg, 1.73 mmol) in dry $CH_2Cl_2$ (70 mL) was added DIPEA (0.9 mL, 5.2 mmol), TBTU (840 mg, 2.6 mmol) and dimethylamine hydrochloride (420 mg, 5.1 mmol). The reaction mixture was stirred overnight at room temperature and then poured into saturated aqueous $NaHCO_3$ (100 mL). The organic layer was washed with brine (50 mL), dried ($Na_2SO_4$) and concentrated. The crude product was purified by column chromatography (ethyl acetate/MeOH 95:5) to afford compound 109 (540 mg, 1.25 mmol, 72%, yellow solid).

$^1$H-NMR ($CDCl_3$): δ 2.97 (s, 3H), 3.11 (s, 3H), 5.53 (s, 2H), 6.90 (dd, 1H, J1=7.6 Hz, J2=1.5 Hz), 6.95 (d, 1H, J=7.6 Hz), 7.17-7.28 (m, 4H), 7.51 (d, 1H, J=7.6 Hz), 7.54 (s, 1H), 7.61-7.66 (m, 2H), 8.28 (dd, 1H, J1=8.4 Hz, J2=1.5 Hz), 8.61 (d, 1H, J=4.6 Hz).

The following compounds were prepared using general procedure 7:

Compound 110: 3-(2-Nitro-phenylsulfanyl)-1-pyridin-2-ylmethyl-1H-indole-6-carboxylic acid methylamide, structure 15 of Scheme IV, where $R^1$ = 2-pyridyl, $R^2$ = 2-nitrophenyl, $R^3 = R^4 = H$, $R^8 = H$, $R^9$ = Me.

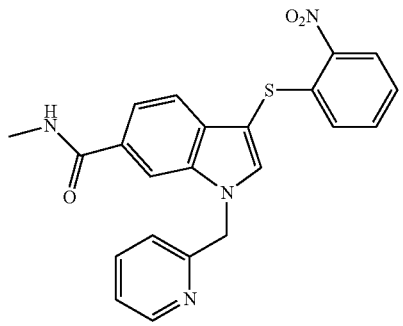

$^1$H-NMR (DMSO): δ 2.78 (d, 3H, J = 4.6 Hz), 5.70 (s, 2H), 6.88 (dd, 1H, J1 = 8.4 Hz, J2 = 1.5 Hz), 7.19 (d, 1H, J = 7.6 Hz), 7.30-7.37 (m, 2H), 7.41 (d, 1H, J1 = 8.4 Hz), 7.48-7.53 (m, 1H), 7.62 (dd, 1H, J1 = 7.6 Hz, J2 = 1.5 Hz), 7.79 (td, 1H, J1 = 7.6 Hz, J2 = 1.5 Hz), 8.13 (s, 1H), 8.20 (s, 1H), 8.28 (dd, 1H, J1 = 8.4 Hz, J2 = 1.5 Hz), 8.38 (q, 1H, J = 4.6 Hz), 8.55 (s, 1H, J = 4.6 Hz).

Compound 111: 3-(2-Nitro-phenylsulfanyl)-1-pyridin-2-ylmethyl-1H-indole-6-carboxylic acid amide, structure 15 of Scheme IV, where $R^1$ = 2-pyridyl, $R^2$ = 2-nitrophenyl, $R^3 = R^4 = H$, $R^8 = R^9 = H$.

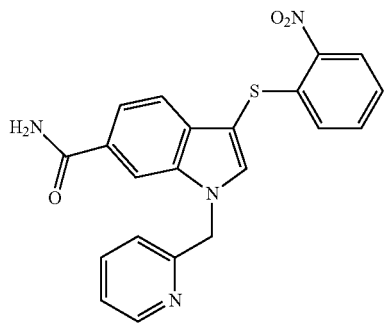

$^1$H-NMR (DMSO): δ 5.70 (s, 2H), 6.88 (dd, 1H, J1 = 8.4 Hz, J2 = 1.5 Hz), 7.21 (d, 1H, J = 7.6 Hz), 7.28-7.37 (m, 3H), 7.39 (d, 1H, J = 7.6 Hz), 7.48-7.53 (m, 1H), 7.66 (dd, 1H, J1 = 8.4 Hz, J2 = 1.5 Hz), 7.79 (td, 1H, J = 7.6 Hz, J2 = 1.5 Hz), 7.93 (s, 1H), 8.17 (s, 1H), 8.20 (s, 1H), 8.26 (dd, 1H, J1 = 7.6 Hz, J2 = 1.5 Hz), 8.55 (d, 1H, J = 4.6 Hz).

Compound 112: 3-(2-Nitro-phenylsulfanyl)-1-pyridin-3-ylmethyl-1H-indole-6-carboxylic acid methylamide, structure 15 of Scheme IV, where $R^1$ = 3-pyridyl, $R^2$ = 2-nitrophenyl, $R^3 = R^4 = H$, $R^8 = H$, $R^9$ = Me. 3-Picolyl chloride hydrochloride was used instead of 2-picolyl chloride hydrochloride.

$^1$H-NMR (DMSO): δ 2.80 (d, 3H, J = 4.6 Hz), 5.65 (s, 2H), 6.84 (dd, 1H, J1 = 7.6 Hz, J2 = 1.1 Hz), 7.33-7.42 (m, 3H), 7.46-7.51 (m, 1H), 7.62 (dd, 1H, J1 = 8.4 Hz, J2 = 1.1 Hz), 7.68 (dt, 1H, J1 = 7.6 Hz, J2 = 2.2 Hz), 8.19 (s, 1H), 8.26 (s, 1H), 8.28 (dd, 1H, J1 = 7.6 Hz, J2 = 1.1 Hz), 8.41 (q, 1H, J = 4.6 Hz), 8.51 (dd, 1H, J1 = 4.6 Hz, J2 = 1.1 Hz), 8.64 (d, 1H, J = 3.0 Hz).

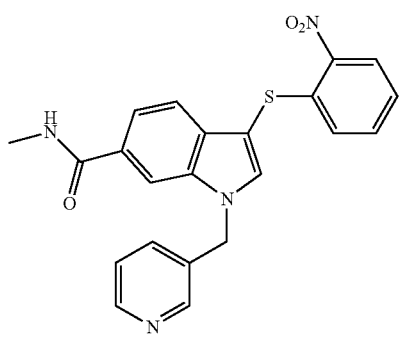

Compound 113: 3-(2-Nitro-phenylsulfanyl)-1-pyridin-3-ylmethyl-1H-indole-6-carboxylic acid ethylamide, structure 15 of Scheme IV, where $R^1$ = 3-pyridyl, $R^2$ = 2-nitrophenyl, $R^3$ = $R^4$ = H, $R^8$ = H, $R^9$ = Et. 3-Picolyl chloride hydrochloride was used instead of 2-picolyl chloride

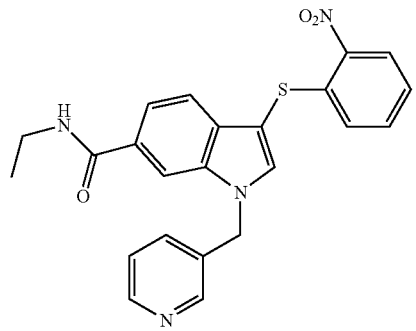

$^1$H-NMR (DMSO): δ 1.13 (t, 3H, J = 7.6 Hz), 3.30 (q, 2H, J = 7.6 Hz), 5.66 (s, 2H), 6.83 (dd, 1H, J1 = 7.6 Hz, J2 = 1.1 Hz), 7.33-7.41 (m, 3H), 7.46-7.51 (m, 1H), 7.64 (dd, 1H, J1 = 7.6 Hz, J2 = 1.1 Hz), 7.67 (dt, 1H, J1 = 7.6 Hz, J2 = 2.2 Hz), 8.19 (s, 1H), 8.26 (s, 1H), 8.27 (dd, 1H, J1 = 7.6 Hz, J2 = 1.1 Hz), 8.45 (t, 1H, J = 5.7 Hz), 8.52 (dd, 1H, J1 = 4.6 Hz, J2 = 1.5 Hz), 8.64 (d, 1H, J = 3.0 Hz).

Compound 114: 3-(2-Nitro-phenylsulfanyl)-1-pyridin-3-ylmethyl-1H-indole-6-carboxylic acid cyclopropylamide, structure 15 of Scheme IV, where $R^1$ = 3-pyridyl, $R^2$ = 2-nitrophenyl, $R^3$ = $R^4$ = H, $R^8$ = H, $R^9$ = cyclopropyl. 3-Picolyl chloride hydrochloride was used instead of 2-picoyl chloride hydrochloride.

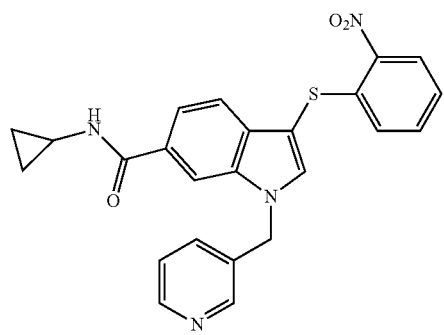

$^1$H-NMR (DMSO): δ 0.54-0.58 (m, 2H), 0.67-0.73 (m, 2H), 2.80-2.87 (m, 1H), 5.66 (s, 2H), 6.82 (d, 1H, J = 7.6 Hz), 7.33-7.41 (m, 3H), 7.46-7.50 (m, 1H), 7.61 (dd, 1H, J1 = 7.6 Hz, J2 = 1.1 Hz), 7.67 (dt, 1H, J1 = 7.6 Hz, J2 = 1.5 Hz), 8.17 (s, 1H), 8.25 (s, 1H), 8.28 (dd, 1H, J1 = 7.6 Hz, J2 = 1.1 Hz), 8.42 (t, 1H, J = 4.6 Hz), 8.52 (dd, 1H, J1 = 4.6 Hz, J2 = 1.5 Hz), 8.63 (d, 1H, J = 3.0 Hz).

Example 23

Compound 118: N-[3-(2-Nitro-phenylsulfanyl)-1-pyrimidin-5-ylmethyl-1H-indol-6-yl]-formamide, Structure 28 of Scheme VII, where $R^1$=3,5-pyrimidyl, $R^2$=2-nitrophenyl, $R^3$=$R^4$=H, Z=H

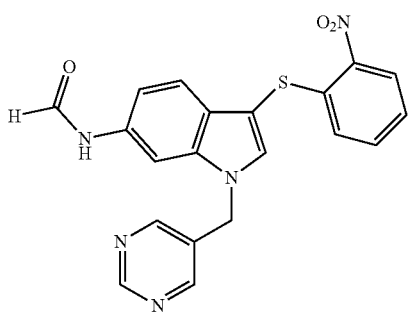

a) 6-Nitro-1-pyrimidin-5-ylmethyl-1H-indole 5-(Hydroxymethyl)pyrimidine (16.2 g, 147 mmol) was dissolved in 500 mL of $CH_2Cl_2$ and cooled to −40° C. MsCl (16.0 g, 140 mmol) was added at −40° C. The mixture was stirred for 1 hour allowing to reach −20° C. The solution was used as such.

6-Nitroindole-1H-indole (35.6 g, 220 mmol) was dissolved in 750 mL of DMF and NaH (50%, 12 g, 250 mmol) was added in portions and the mixture was stirred for 1 hour. The mixture was cooled to −40° C. and the solution of the mesylate was added dropwise. The mixture was allowed to reach room temperature overnight. The mixture was quenched with water and extracted with ethyl acetate (2×). The combined organic layers were washed with water (2×) and brine and dried over $Na_2SO_4$. After concentration in vacuo the material was purified by means of column chromatography (silica, heptane/ethyl acetate (1:1)→(1:4)) affording compound the title compound as a yellow solid (14 g, 55 mmol, 39%).

b) 1-Pyrimidin-5-ylmethyl-1H-indol-6-ylamine

6-Nitro-1-pyrimidin-5-ylmethyl-1H-indole (4.1 g, 16.1 mmol) was dissolved in 100 mL of THF and 100 mL of isopropanol. Pd/C (2 g) was added and the mixture was stirred under an $H_2$-atmosphere (balloon) for 2 hours. The mixture was filtered over Celite and washed with ethyl acetate affording the title compound after concentration (3.5 g, 15.6 mmol, 97%).

c) 1-Pyrimidin-5-ylmethyl-1H-indol-6-yl)-carbamic acid tert-butyl ester

1-Pyrimidin-5-ylmethyl-1H-indol-6-ylamine (5.5 g, 24.6 mmol) was dissolved in 100 mL of NMP and triethylamine (3.5 g, 35 mmol) and di-tert-butyl dicarbonate (7.0 g, 32 mmol) were added. The mixture was stirred overnight, quenched with NaHCO₃-sat and extracted with toluene (3×). The combined organic layers were washed with water (4×) and brine and dried over Na₂SO₄. Concentration of the layers afforded the title compound (3.1 g, 39%).

d) [3-(2-Nitro-phenylsulfanyl)-1-pyrimidin-5-ylmethyl-1H-indol-6-yl]-carbamic acid tert-butyl ester 1-Pyrimidin-5-ylmethyl-1H-indol-6-yl)-carbamic acid tert-butyl ester (3.1 g, 9.6 mmol) was dissolved in 150 mL of CH₂Cl₂ and 2-nitrobenzene sulfonylchloride (1.86 g, 9.8 mmol) was added. The mixture was stirred for 18 hours and quenched with NaHCO₃-sat and extracted with ethyl acetate (2×). The combined organic layers were washed with brine and dried over Na₂SO₄. The product was purified by means of column chromatography (silica, heptane/ethyl acetate (1:1) which gave the title compound as a yellow solid (3.8 g, 83%).

e) N-[3-(2-Nitro-phenylsulfanyl)-1-pyrimidin-5-ylmethyl-1H-indol-6-yl]-formamide

[3-(2-Nitro-phenylsulfanyl)-1-pyrimidin-5-ylmethyl-1H-indol-6-yl]-carbamic acid tert-butyl ester (3.8 g, 8.0 mmol) was dissolved in 150 mL of formic acid and stirred for 4 hours. The solution was concentrated in vacuo. NaHCO₃-sat was added and the mixture was extracted with CH₂Cl₂ (2×) The combined organic layers were washed with brine and dried over Na₂SO₄. The solution was allowed to stand overnight. The formed solid was filtered affording a mixture of compound 118 and structure 23 of Scheme VII, where R¹=3, 5-pyrimidyl, R²=2-nitrophenyl, R³=R⁴=H (2.4 g).

Compound 118: ¹H NMR (CDCl₃+drop MeOD) δ 5.47 (s, 2H), 6.91 (dd, 1H, J1=8.4 Hz, J2=1.1 Hz), 6.99 (dd, 1H, J1=8.4 Hz, J2=1.9 Hz), 7.19-7.23 (m, 1H), 7.27-7.31 (m, 1H), 7.33 (s, 1H), 7.42 (d, 1H, J=8.4 Hz), 7.49 (s, 1H), 8.22 (d, 1H, J=1.9 Hz), 8.27 (dd, 1H, J1=8.4 Hz, J2=1.1 Hz), 8.66 (s, 2H), 9.16 (s, 1H).

Example 24

Compound 119: 3-(2-Nitro-phenylsulfanyl)-1-pyridin-2-ylmethyl-1H-indole-6-carbonitrile, Structure 3 of Scheme I, where R¹=2-pyridyl, R²=2-nitrophenyl, R³=R⁴=H, R⁵=CN

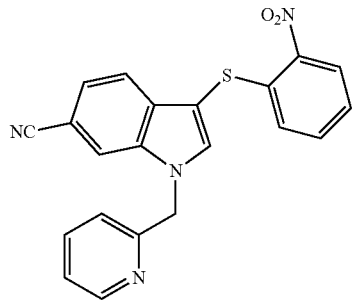

a) To a solution of 1H-indole-6-carbonitrile (1.00 g, 7.04 mmol) in diethyl ether (50 mL) was added at rt 2-nitrobenzenesulfenyl chloride (1.34 g, 7.04 mmol) and the reaction mixture was stirred for 18 hrs. The mixture was concentrated and the crude product was purified using column chromatography (ethyl acetate/heptane 1:4→4:1) to give 3-(2-Nitrophenylsulfanyl)-1H-indole-6-carbonitrile (1.62 g, 5.49 mmol, 78%).

b) To a solution of 3-(2-nitro-phenylsulfanyl)-1H-indole-6-carbonitrile (200 mg, 0.68 mmol) in DMF (5 mL) was added at 0° C. Cs₂CO₃ (442 mg, 1.36 mmol) and the mixture was stirred for 20 min. Subsequently 2-picolylchloride hydrochloride (112 mg, 0.68 mmol) was added and the mixture was stirred for 18 hrs at room temperature. Aqueous saturated NaHCO₃ was added and the mixture was extracted with ethyl acetate (2×). The combined organic layers were washed with brine, dried (Na₂SO₄) and concentrated. The crude product was purified using column chromatography to afford compound 119 (223 mg, 0.58 mmol, 85%).

¹H NMR (CDCl₃) δ 5.54 (s, 2H), 6.86 (dd, 1H, J1=8.4 Hz, J2=1.1 Hz), 7.04 (d, 1H, J=8.4 Hz), 7.19-7.23 (m, 1H), 7.26-7.31 (m, 2H), 7.40 (dd, 1H, J1=8.4 Hz, J2=1.1 Hz), 7.59 (d, 1H, J=8.4 Hz), 7.70 (td, 1H, J1=8.4 Hz, J2=1.9 Hz), 7.76 (s, 1H), 7.78 (s, 1H), 8.29 (dd, 1H, J1=8.4 Hz, J2=1.1 Hz), 8.63 (d, 1H, J=3.0 Hz).

According to general method 3 the following compounds were prepared:

Compound 121: 3-(2-Nitro-phenylsulfanyl)-1-pyridin-3-ylmethyl-1H-indole-6-carbonitrile, structure 3 of scheme I, where $R^1$ = 3-pyridyl, $R^2$ = 2-nitrophenyl, $R^3$ = $R^4$ = H, $R^5$ = CN. $Cs_2CO_3$ and DMF were used.

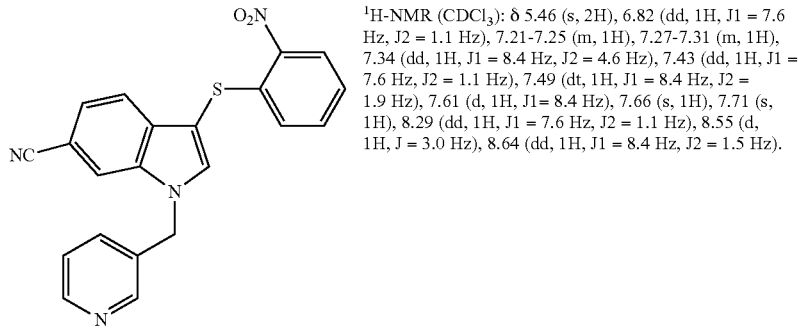

$^1$H-NMR (CDCl$_3$): δ 5.46 (s, 2H), 6.82 (dd, 1H, J1 = 7.6 Hz, J2 = 1.1 Hz), 7.21-7.25 (m, 1H), 7.27-7.31 (m, 1H), 7.34 (dd, 1H, J1 = 8.4 Hz, J2 = 4.6 Hz), 7.43 (dd, 1H, J1 = 7.6 Hz, J2 = 1.1 Hz), 7.49 (dt, 1H, J1 = 8.4 Hz, J2 = 1.9 Hz), 7.61 (d, 1H, J1 = 8.4 Hz), 7.66 (s, 1H), 7.71 (s, 1H), 8.29 (dd, 1H, J1 = 7.6 Hz, J2 = 1.1 Hz), 8.55 (d, 1H, J = 3.0 Hz), 8.64 (dd, 1H, J1 = 8.4 Hz, J2 = 1.5 Hz).

Compound 122: 3-(2-Nitro-phenylsulfanyl)-1-pyridin-4-ylmethyl-1H-indole-6-carbonitrile, structure 3 of scheme I, where $R^1$ = 4-pyridyl, $R^2$ = 2-nitrophenyl, $R^3$ = $R^4$ = H, $R^5$ = CN.

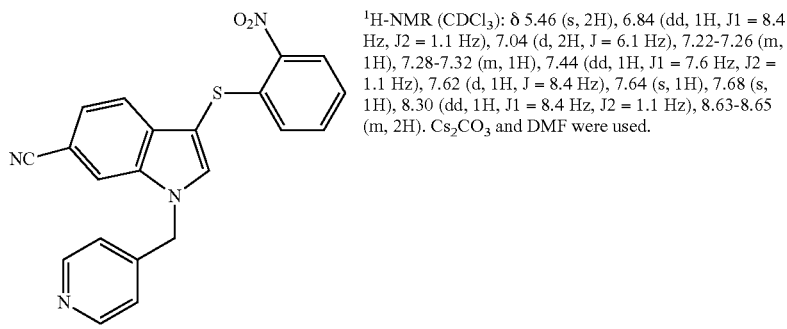

$^1$H-NMR (CDCl$_3$): δ 5.46 (s, 2H), 6.84 (dd, 1H, J1 = 8.4 Hz, J2 = 1.1 Hz), 7.04 (d, 2H, J = 6.1 Hz), 7.22-7.26 (m, 1H), 7.28-7.32 (m, 1H), 7.44 (dd, 1H, J1 = 7.6 Hz, J2 = 1.1 Hz), 7.62 (d, 1H, J = 8.4 Hz), 7.64 (s, 1H), 7.68 (s, 1H), 8.30 (dd, 1H, J1 = 8.4 Hz, J2 = 1.1 Hz), 8.63-8.65 (m, 2H). $Cs_2CO_3$ and DMF were used.

Compound 123: 3-(2-Nitro-phenylsulfanyl)-1-pyrimidin-5-ylmethyl-1H-indole-6-carbonitrile, structure 3 of scheme I, where $R^1$ = 3,5-pyrimidyl, $R^2$ = 2-nitrophenyl, $R^3$ = $R^4$ = H, $R^5$ = CN. NaH and DMF were used.

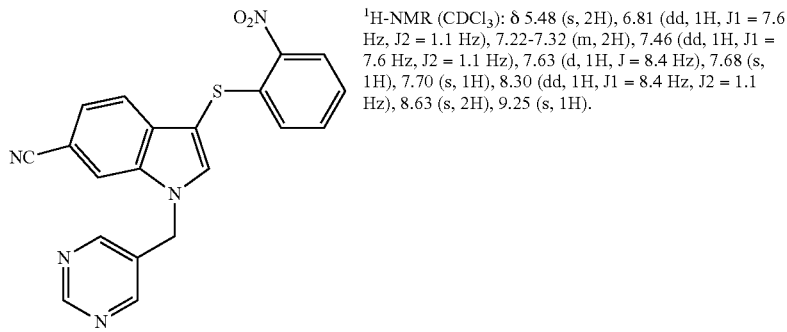

$^1$H-NMR (CDCl$_3$): δ 5.48 (s, 2H), 6.81 (dd, 1H, J1 = 7.6 Hz, J2 = 1.1 Hz), 7.22-7.32 (m, 2H), 7.46 (dd, 1H, J1 = 7.6 Hz, J2 = 1.1 Hz), 7.63 (d, 1H, J = 8.4 Hz), 7.68 (s, 1H), 7.70 (s, 1H), 8.30 (dd, 1H, J1 = 8.4 Hz, J2 = 1.1 Hz), 8.63 (s, 2H), 9.25 (s, 1H).

Compound 124: 3-(2-Nitro-phenylsulfanyl)-1-pyrimidin-4-ylmethyl-1H-indole-6-carbonitrile, structure 3 of scheme I, where $R^1$ = 2,4-pyrimidyl, $R^2$ = 2-nitrophenyl, $R^3$ = $R^4$ = H, $R^5$ = CN. $Cs_2CO_3$ and DMF were used.

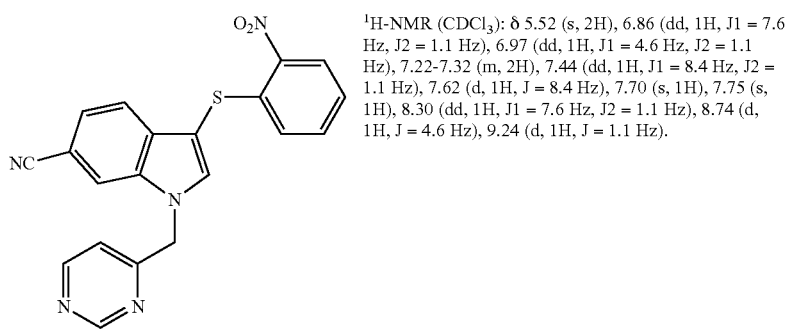

$^1$H-NMR (CDCl$_3$): δ 5.52 (s, 2H), 6.86 (dd, 1H, J1 = 7.6 Hz, J2 = 1.1 Hz), 6.97 (dd, 1H, J1 = 4.6 Hz, J2 = 1.1 Hz), 7.22-7.32 (m, 2H), 7.44 (dd, 1H, J1 = 8.4 Hz, J2 = 1.1 Hz), 7.62 (d, 1H, J = 8.4 Hz), 7.70 (s, 1H), 7.75 (s, 1H), 8.30 (dd, 1H, J1 = 7.6 Hz, J2 = 1.1 Hz), 8.74 (d, 1H, J = 4.6 Hz), 9.24 (d, 1H, J = 1.1 Hz).

Compound 125: 1-(3-Cyano-benzyl)-3-(2-nitro-phenylsulfanyl)-1H-indole-6-carbonitrile, structure 3 of scheme I, where $R^1$ = 3-cyanophenyl, $R^2$ = 2-nitrophenyl, $R^3 = R^4$ = H, $R^5$ = CN. $Cs_2CO_3$ and DMF were used.

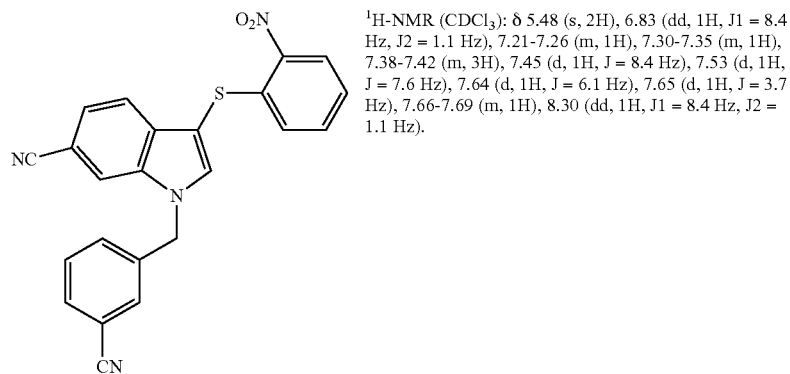

$^1$H-NMR (CDCl$_3$): δ 5.48 (s, 2H), 6.83 (dd, 1H, J1 = 8.4 Hz, J2 = 1.1 Hz), 7.21-7.26 (m, 1H), 7.30-7.35 (m, 1H), 7.38-7.42 (m, 3H), 7.45 (d, 1H, J = 8.4 Hz), 7.53 (d, 1H, J = 7.6 Hz), 7.64 (d, 1H, J = 6.1 Hz), 7.65 (d, 1H, J = 3.7 Hz), 7.66-7.69 (m, 1H), 8.30 (dd, 1H, J1 = 8.4 Hz, J2 = 1.1 Hz).

Example 25

Compound 120: 3-(2-Nitro-phenylsulfanyl)-1-pyridin-2-ylmethyl-1H-indol-6-carbonitrile monohydrochloride

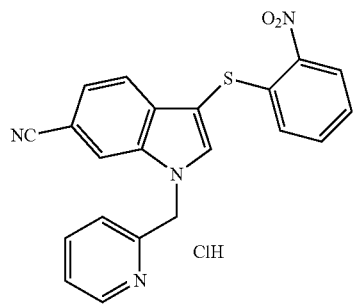

Concentrated hydrochloric acid (0.0225 ml) was added to a solution of compound 119 (0.093 g) in dioxane. The mixture was stirred for 20 min. and then concentrated under reduced pressure, to give compound 120 (0.096 g).

$^1$H NMR (MeOD) δ 6.01 (s, 2H), 6.98 (dd, 1H, J1=7.6 Hz, J2=1.1 Hz), 7.28-7.32 (m, 1H), 7.36-7.41 (m, 1H), 7.48 (dd, 1H, J1=7.6 Hz, J2=1.1 Hz), 7.53 (d, 1H, J=8.4 Hz), 7.60 (d, 1H, J=8.4 Hz), 7.93 (t, 1H, J=6.1 Hz), 8.08 (s, 1H), 8.10 (s, 1H), 8.27 (dd, 1H, J1=8.4 Hz, J2=1.1 Hz), 8.44 (td, 1H, J1=8.4 Hz, J2=1.1 Hz), 8.85 (dd, 1H, J1=6.1 Hz, J2=1.9 Hz).

Compounds were tested for their Androgen Receptor activity in a transactivation assay and in a binding assay.

The (anti-)androgenic activity of test compounds (EC50 and intrinsic activity) was determined in an in vitro bioassay of Chinese hamster ovary (CHO) cells stably transfected with the human androgen receptor expression plasmid and a reporter plasmid in which the MMTV-promoter is linked to the luciferase reporter gene. The cell-line CHO-AR-pM-MTV-LUC 1G12-A5-CA is described in Schoonen et al. (2000), Journal of Steroid Biochemistry and Molecular Biology 74(4):213-222. The antiandrogenic activity of a test compound was determined by the inhibition of the transactivation via the androgen receptor of the enzyme luciferase in the presence of 1 nM DHT (5α-dihydrotestosterone, 17β-hydroxy-5α-androstan-3-one). Intrinsic activity of antiandrogenic activity was determined in the presence of the reference antiandrogen 2-Hydroxy-2-methyl-N-(4-nitro-3-trifluoromethyl-phenyl)-propionamide(Hydroxyflutamide), and set at 100%. For androgenic activity, maximal intrinsic activity in the presence of 100 nM DHT was set at 100%. The results are presented in Table 4.

TABLE 4

| Androgen receptor activity | | | | | | | | | | |
|---|---|---|---|---|---|---|---|---|---|---|
| Cpd. number | X | $R^1$ | $R^2$ | $R^3$ | $R^4$ | $R^5$ | ago EC50 | ago efficacy | ant EC50 | ant efficacy |
| 1 | S | 2,5-difluorophenyl | 2-nitrophenyl | H | H | OMe | ++ | + | − | − |
| 2 | S | 2,fluoro,3-methylphenyl | 2-nitrophenyl | H | H | OMe | + | + | − | − |
| 3 | S | 2-chlorophenyl | 2-nitrophenyl | H | H | OMe | + | + | − | − |
| 4 | S | 2-cyanophenyl | 2-nitrophenyl | H | H | OMe | + | ± | ++ | ± |
| 5 | S | 2-fluorophenyl | 2-nitrophenyl | H | H | OMe | + | + | − | − |
| 6 | S | 2-methyl,3-nitrophenyl | 2-nitrophenyl | H | H | OMe | + | + | − | − |
| 7 | S | 2-methylphenyl | 2-nitrophenyl | H | H | OMe | ++ | ++ | − | − |
| 8 | S | 2-nitrophenyl | 2-nitrophenyl | H | H | OMe | ++ | + | − | − |
| 9 | S | 2-pyridyl | 2-nitrophenyl | H | H | OMe | +++ | + | +++ | ± |
| 10 | S | 2-pyridyl HCl salt | 2-nitrophenyl | H | H | OMe | ++ | + | − | − |
| 11 | S | 2-tetrahydropyranyl | 2-nitrophenyl | H | H | OMe | ++ | + | − | − |
| 12 | S | 2-trifluoromethylphenyl | 2-nitrophenyl | H | H | OMe | + | + | − | − |
| 13 | S | 3-(5-methylisoxazolyl) | 2-nitrophenyl | H | H | OMe | + | ± | − | − |
| 14 | S | 3,4-dichlorophenyl | 2-nitrophenyl | H | H | OMe | + | + | − | − |
| 15 | S | 3,5-dichlorophenyl | 2-nitrophenyl | H | H | OMe | ++ | ++ | − | − |

TABLE 4-continued

Androgen receptor activity

| Cpd. number | X | R¹ | R² | R³ | R⁴ | R⁵ | ago EC50 | ago efficacy | ant EC50 | ant efficacy |
|---|---|---|---|---|---|---|---|---|---|---|
| 16 | S | 3,5-difluorophenyl | 2-(hydroxymethylphenyl) | H | H | OMe | ++ | + | ++ | ± |
| 17 | S | 3,5-difluorophenyl | 2-(N-methylbenzamide) | H | H | OMe | − | − | + | + |
| 18 | S | 3,5-difluorophenyl | 2-benzamide | H | H | OMe | ++ | + | ++ | ± |
| 19 | S | 3,5-difluorophenyl | 2-benzoic acid methyl ester | H | H | OMe | + | + | − | − |
| 20 | S | 3,5-difluorophenyl | 2-cyanophenyl | H | H | OMe | ++ | ++ | − | − |
| 21 | S | 3,5-difluorophenyl | 2-methoxyphenyl | H | H | OMe | ++ | | | |
| 22 | S | 3,5-difluorophenyl | 2-nitrophenyl | H | H | Br | ++ | | ++ | − |
| 23 | S | 3,5-difluorophenyl | 2-nitrophenyl | H | H | CF3 | +++ | ++ | − | − |
| 24 | S | 3,5-difluorophenyl | 2-nitrophenyl | H | H | CH2OH | ++ | ++ | − | − |
| 25 | S | 3,5-difluorophenyl | 2-nitrophenyl | H | H | Cl | +++ | ++ | − | − |
| 26 | S | 3,5-difluorophenyl | 2-nitrophenyl | H | H | CN | +++ | ++ | − | − |
| 27 | S | 3,5-difluorophenyl | 2-nitrophenyl | H | H | CO(1-pyrrolidinyl) | ++ | + | − | − |
| 28 | S | 3,5-difluorophenyl | 2-nitrophenyl | H | H | CO(4-morpholinyl) | ++ | + | − | − |
| 29 | S | 3,5-difluorophenyl | 2-nitrophenyl | H | H | CO[1-(4-methylpiperazinyl)] | ++ | ++ | − | − |
| 30 | S | 3,5-difluorophenyl | 2-nitrophenyl | H | H | CO2H | + | + | − | − |
| 31 | S | 3,5-difluorophenyl | 2-nitrophenyl | H | H | CO2Me | +++ | + | − | − |
| 32 | S | 3,5-difluorophenyl | 2-nitrophenyl | H | H | CONEt2 | ++ | + | + | ± |
| 33 | S | 3,5-difluorophenyl | 2-nitrophenyl | H | H | CONH2 | +++ | ++ | − | − |
| 34 | S | 3,5-difluorophenyl | 2-nitrophenyl | H | H | CONHCH2(2-furanyl) | ++ | + | − | − |
| 35 | S | 3,5-difluorophenyl | 2-nitrophenyl | H | H | CONHCH2(3-pyridyl) | ++ | ± | − | − |
| 36 | S | 3,5-difluorophenyl | 2-nitrophenyl | H | H | CONHCH2CH2Nme2 | ++ | + | − | − |
| 37 | S | 3,5-difluorophenyl | 2-nitrophenyl | H | H | CONHCH2CH2OH | +++ | ++ | − | − |
| 38 | S | 3,5-difluorophenyl | 2-nitrophenyl | H | H | CONHCH2CH2OMe | +++ | ++ | − | − |
| 39 | S | 3,5-difluorophenyl | 2-nitrophenyl | H | H | CONHCH2CO2Me | ++ | ++ | − | − |
| 40 | S | 3,5-difluorophenyl | 2-nitrophenyl | H | H | CONHCH2CONMe2 | ++ | + | − | − |
| 41 | S | 3,5-difluorophenyl | 2-nitrophenyl | H | H | CONHCH2cPr | +++ | + | − | − |
| 42 | S | 3,5-difluorophenyl | 2-nitrophenyl | H | H | CONHCH2iPr | ++ | + | − | − |
| 43 | S | 3,5-difluorophenyl | 2-nitrophenyl | H | H | CONHCH2Ph | ++ | ± | + | ± |
| 44 | S | 3,5-difluorophenyl | 2-nitrophenyl | H | H | CONHePr | +++ | + | − | − |
| 45 | S | 3,5-difluorophenyl | 2-nitrophenyl | H | H | CONHEt | +++ | ++ | − | − |
| 46 | S | 3,5-difluorophenyl | 2-nitrophenyl | H | H | CONHiPr | ++ | + | ++ | ± |
| 47 | S | 3,5-difluorophenyl | 2-nitrophenyl | H | H | CONHMe | +++ | + | − | − |
| 48 | S | 3,5-difluorophenyl | 2-nitrophenyl | H | H | CONHnPr | ++ | + | + | ± |
| 49 | S | 3,5-difluorophenyl | 2-nitrophenyl | H | H | CONMe2 | +++ | + | − | − |
| 50 | S | 3,5-difluorophenyl | 2-nitrophenyl | H | H | F | ++ | ++ | − | − |
| 51 | S | 3,5-difluorophenyl | 2-nitrophenyl | F | H | H | +++ | ++ | − | − |
| 52 | S | 3,5-difluorophenyl | 2-nitrophenyl | H | H | H | ++ | ++ | − | − |
| 53 | S | 3,5-difluorophenyl | 2-nitrophenyl | H | F | H | ++ | ++ | − | − |
| 54 | S | 3,5-difluorophenyl | 2-nitrophenyl | Cl | H | H | ++ | ++ | − | − |
| 55 | S | 3,5-difluorophenyl | 2-nitrophenyl | Me | H | H | ++ | + | − | − |
| 56 | S | 3,5-difluorophenyl | 2-nitrophenyl | H | OH | H | +++ | | | |
| 57 | S | 3,5-difluorophenyl | 2-nitrophenyl | H | H | NH2 | + | + | − | − |
| 58 | S | 3,5-difluorophenyl | 2-nitrophenyl | H | H | NHAc | +++ | ++ | − | − |
| 59 | S | 3,5-difluorophenyl | 2-nitrophenyl | H | H | NHCOCF3 | +++ | + | − | − |
| 60 | S | 3,5-difluorophenyl | 2-nitrophenyl | H | H | NO2 | +++ | ++ | − | − |
| 61 | S | 3,5-difluorophenyl | 2-nitrophenyl | H | H | OH | +++ | | | |
| 62 | SO2 | 3,5-difluorophenyl | 2-nitrophenyl | H | H | OMe | +++ | ++ | − | − |
| 63 | S | 3,5-difluorophenyl | 2-nitrophenyl | H | H | OMe | +++ | ++ | − | − |
| 64 | SO | 3,5-difluorophenyl | 2-nitrophenyl | H | H | OMe | − | ± | + | + |
| 65 | S | 3,5-difluorophenyl | 2-pyridyl | H | H | OMe | ++ | ++ | − | − |
| 66 | S | 3,5-difluorophenyl | 2-pyridyl-N-oxide | H | H | OMe | + | + | ++ | ± |
| 67 | S | 3-chlorophenyl | 2-nitrophenyl | H | H | OMe | ++ | ++ | − | − |
| 68 | S | 3-cyanophenyl | 2-nitrophenyl | H | H | OMe | +++ | ++ | − | − |
| 69 | S | 3-fluoro,5-trifluoromethylphenyl | 2-nitrophenyl | H | H | OMe | ++ | ++ | − | − |
| 70 | S | 3-fluoro,6-trifluoromethylphenyl | 2-nitrophenyl | H | H | OMe | ++ | + | − | − |
| 71 | S | 3-fluorophenyl | 2-nitrophenyl | H | H | OMe | +++ | ++ | − | − |
| 72 | S | 3-methoxyphenyl | 2-nitrophenyl | H | H | OMe | ++ | + | − | − |
| 73 | S | 3-methylphenyl | 2-nitrophenyl | H | H | OMe | ++ | ++ | − | − |
| 74 | S | 3-nitrophenyl | 2-nitrophenyl | H | H | OMe | +++ | ++ | − | − |
| 75 | S | 3-pyridyl | 2-nitrophenyl | H | H | OMe | +++ | ++ | − | − |
| 76 | S | 3-trifluoromethyl,4-chlorophenyl | 2-nitrophenyl | H | H | OMe | + | + | − | − |
| 77 | S | 3-trifluoromethyloxyphenyl | 2-nitrophenyl | H | H | OMe | ++ | ++ | − | − |
| 78 | S | 3-trifluoromethylphenyl | 2-nitrophenyl | H | H | OMe | ++ | ++ | − | − |
| 79 | S | 4-(2-methylthiazolyl) | 2-nitrophenyl | H | H | OMe | ++ | + | − | − |
| 80 | S | 4-(3,5-dimethylisoxazolyl) | 2-nitrophenyl | H | H | OMe | + | ± | + | ± |
| 81 | S | 4-chlorophenyl | 2-nitrophenyl | H | H | OMe | + | + | +++ | + |
| 82 | S | 4-cyanophenyl | 2-nitrophenyl | H | H | OMe | ++ | + | − | − |
| 83 | S | 4-fluorophenyl | 2-nitrophenyl | H | H | OMe | ++ | ++ | − | − |
| 84 | S | 4-methoxyphenyl | 2-nitrophenyl | H | H | OMe | + | ± | ± | ++ |
| 85 | S | 4-methylphenyl | 2-nitrophenyl | H | H | OMe | + | + | − | ± |

TABLE 4-continued

Androgen receptor activity

| Cpd. number | X | R¹ | R² | R³ | R⁴ | R⁵ | ago EC50 | ago efficacy | ant EC50 | ant efficacy |
|---|---|---|---|---|---|---|---|---|---|---|
| 86 | S | 4-morpholinyl | 2-nitrophenyl | H | H | OMe | ± | ± | + | + |
| 87 | S | 5-(2-chlorothiazolyl) | 2-nitrophenyl | H | H | OMe | ++ | + | − | − |
| 88 | S | 5-(2-chlorothiophenyl) | 2-nitrophenyl | H | H | OMe | ++ | ++ | − | − |
| 89 | S | Cyclohexyl | 2-nitrophenyl | H | H | OMe | ++ | + | +++ | ± |
| 90 | S | Phenyl | 2-nitrophenyl | H | H | H | + | + | − | − |
| 91 | S | Phenyl | 2-nitrophenyl | H | OMe | H | − | − | ± | ++ |
| 92 | S | Phenyl | 2-nitrophenyl | H | H | OMe | +++ | ++ | − | − | note 1:
EC50 scale: +++ <5 nM; ++ between 5 and 100 nM; + <1000 nM; ± between 1000 and 10000 nM; − >10000 nM note 2:
efficacy scale (maximal intrinsic activity, i.e. intrinsic activity observed in the presence of 100 nM DHT, was set at 1.00): ++ ≧0.80; + between 0.50 and 0.80; ± between 0.20 and 0.50; − <0.20

The androgenic activity (EC50, potency, and efficacy) of the compounds in Table 5 was determined in an in vitro bioassay of Chinese hamster ovary (CHO) cells stably transfected with the human androgen receptor expression plasmid and a reporter plasmid in which the MMTV promoter is linked to the luciferase reporter gene. The cell line CHO-AR-pMMTV-LUC 1G12-A5-CA is described in Schoonen et al. (J. Steroid Biochem. Moles. Biol. 2002; 74: 213-222). The androgen receptor activity of compounds was determined in the presence of 0.1 µmol/l onapristone. The maximal efficacy in the presence of 100 nmol/l DHT was set as 100%. The potencies are expressed as percentage of DHT activity.

TABLE 5

Androgen receptor activity

| Cpd. number | X | R¹ | R² | R³ | R⁴ | R⁵ | ago potency | ago efficacy |
|---|---|---|---|---|---|---|---|---|
| 93 | S | 4-pyridyl | 2-nitrophenyl | H | H | OMe | ± | + |
| 94 | S | 3,4,5-trifluorophenyl | 2-nitrophenyl | H | H | OMe | + | ++ |
| 95 | S | 2,3,5-trifluorophenyl | 2-nitrophenyl | H | H | OMe | ± | ++ |
| 96 | S | 4-chloro-3-pyridyl | 2-nitrophenyl | H | H | OMe | ± | ± |
| 97 | S | 3,5-difluorophenyl | 2-nitrophenyl | H | H | NHCOCH2F | + | ++ |
| 98 | S | 3,5-difluorophenyl | 2-nitrophenyl | H | H | NHCOCHF2 | ++ | + |
| 99 | S | 3,5-difluorophenyl | 2-nitrophenyl | H | H | NHCOEt | ± | + |
| 100 | S | 2-pyridyl | 2-nitrophenyl | H | H | NHCOCH2F | + | ++ |
| 101 | S | 2-pyridyl | 2-nitrophenyl | H | H | NHCOMe | + | + |
| 102 | S | 2-pyridyl | 2-nitrophenyl | H | H | NHCOEt | + | + |
| 103 | S | 3-pyridyl | 2-nitrophenyl | H | H | NHCOMe | + | + |
| 104 | S | 3-pyridyl | 2-nitrophenyl | H | H | NHCOCH2F | + | − |
| 105 | S | 3-pyridyl | 2-nitrophenyl | H | H | NHCOEt | + | ± |
| 106 | S | 3,5-difluorophenyl | 2-nitrophenyl | H | H | NHSO2Me | + | ++ |
| 107 | S | 3,5-difluorophenyl | 2-nitrophenyl | H | H | NHSO2-(3-thiophene) | + | ++ |
| 108 | S | 3,5-difluorophenyl | 2-nitrophenyl | H | H | NHSO2-(1-Me-4-imidazolyl) | + | ++ |
| 109 | S | 2-pyridyl | 2-nitrophenyl | H | H | CONMe2 | + | ++ |
| 110 | S | 2-pyridyl | 2-nitrophenyl | H | H | CONHMe | + | + |
| 111 | S | 2-pyridyl | 2-nitrophenyl | H | H | CONH2 | ± | ± |
| 112 | S | 3-pyridyl | 2-nitrophenyl | H | H | CONHMe | + | ± |
| 113 | S | 3-pyridyl | 2-nitrophenyl | H | H | CONHEt | + | + |
| 114 | S | 3-pyridyl | 2-nitrophenyl | H | H | CONHcyclopropyl | + | ++ |
| 115 | S | 3,5-pyrimidyl | 2-nitrophenyl | H | H | OMe | ++ | + |
| 116 | S | 2,4-pyrimidyl | 2-nitrophenyl | H | H | OMe | + | + |
| 117 | S | 2,5-pyrazyl | 2-nitrophenyl | H | H | OMe | + | + |
| 118 | S | 3,5-pyrimidyl | 2-nitrophenyl | H | H | NHCHO | ++ | + |
| 119 | S | 2-pyridyl | 2-nitrophenyl | H | H | CN | ++ | ++ |
| 120 | S | 2-pyridyl HCl salt | 2-nitrophenyl | H | H | CN | ++ | ++ |
| 121 | S | 3-pyridyl | 2-nitrophenyl | H | H | CN | + | ++ |
| 122 | S | 4-pyridyl | 2-nitrophenyl | H | H | CN | + | + |
| 123 | S | 3,5-pyrimidyl | 2-nitrophenyl | H | H | CN | ++ | ++ |
| 124 | S | 2,4-pyrimidyl | 2-nitrophenyl | H | H | CN | ++ | ++ |
| 125 | S | 3-cyanophenyl | 2-nitrophenyl | H | H | CN | + | ++ | note 1:
potency scale: ++ >5%; + between 1% and 5%; ± between 0.1% and 1%.

note 2:
efficacy scale (maximal intrinsic activity, i.e. intrinsic activity observed in the presence of 100 nM DHT, was set at 1.00): ++ ≧0.80; + between 0.50 and 0.80; ± between 0.20 and 0.50; − <0.20.

Determination of competitive binding to cytoplasmic human androgen receptor from recombinant CHO cells is used to estimate the relative binding affinity (RBA) of a test compound for androgen receptors present in the cytosol prepared of the recombinant CHO cell-line, CHO-AR-pMMTV-LUC 1G12-A5-CA.

Compound 63 and compound 92 were tested in this binding assay and both compounds were found to have a relative binding affinity >1% relative to DHT.

The invention claimed is:

1. A compound having the formula

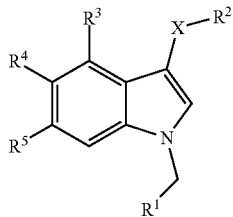

wherein
X is S, SO or $SO_2$;
$R^1$ is phenyl optionally substituted with one or more substituents selected from the group consisting of halogen, CN, (1C-4C)fluoroalkyl, nitro, (1C-4C)alkyl, (1C-4C)alkoxy and (1C-4C)fluoroalkoxy;
$R^2$ is 2-nitrophenyl, 2-cyanophenyl, 2-hydroxymethyl-phenyl, 2-benzamide, 2-benzoic acid methyl ester or 2-methoxyphenyl;
$R^3$ is H, halogen or (1C-4C)alkyl;
$R^4$ is H, OH, (1C-4C)alkoxy, or halogen;
$R^5$ is H, OH, (1C-4C)alkoxy, $NH_2$, CN, halogen, (1C-4C)fluoroalkyl, $NO_2$, hydroxy(1C-4C)alkyl, $CO_2H$, $CO_2$(1C-6C)alkyl, or
$R^5$ is $NHR^6$, wherein $R^6$ is (1C-6C)acyl optionally substituted with one or more halogens, $S(O)_2$(1C-4C)alkyl, or $S(O)_2$aryl optionally substituted with (1C-4C)alkyl or one or more halogens, or
$R^5$ is $C(O)N(R^8,R^9)$, wherein $R^8$ and $R^9$ each independently are H, (3C-6C)cycloalkyl, or $CH_2R^{10}$,
wherein $R^{10}$ is H, (1C-5C)alkyl, (1C-5C)alkenyl, hydroxy(1C-3C)alkyl, (1C-4C)alkylester of carboxy(1C-4C)alkyl, (1C-3C)alkoxy(1C-3C)alkyl, (mono- or di(1C-4C)alkyl)aminomethyl, (mono- or di(1C-4C)alkyl)aminocarbonyl, or a 3-, 4-, 5- or 6-membered monocyclic, homocyclic or, aromatic or non-aromatic ring;
or a salt thereof.

2. The compound according to claim 1, wherein,
$R^1$ phenyl optionally substituted with one or more substituents selected from the group consisting of halogen, CN, $CF_3$, nitro, methoxy, trifluoromethoxy and methyl;
$R^2$ is 2-nitrophenyl, 2-cyanophenyl, 2-hydroxymethyl-phenyl, 2-benzamide, 2-benzoic acid methyl ester or 2-methoxyphenyl;
$R^3$ is H, halogen or (1C-2C)alkyl; and
$R^4$ is H or F.

3. The compound according to claim 2, wherein,
$R^5$ is H, OH, (1C-4C)alkoxy, CN, halogen, (1C-4C)fluoroalkyl, $NO_2$, hydroxy(1C-4C)alkyl, $CO_2$(1C-6C)alkyl, or
$R^5$ is $NHR^6$, wherein $R^6$ is (1C-6C)acyl optionally substituted with one or more halogens, $S(O)_2$(1C-4C)alkyl, or $S(O)_2$aryl optionally substituted with (1C-4C)alkyl or one or more halogens, or
$R^5$ is $C(O)N(R^8,R^9)$, wherein $R^8$ and $R^9$ each independently are H, (3C-6C)cycloalkyl, or $CH_2R^{10}$, wherein $R^{10}$ is H, (1C-5C)alkyl, (1C-5C)alkenyl, hydroxy(1C-3C)alkyl, (1C-4C)alkylester of carboxy(1C-4C)alkyl, (1C-3C)alkoxy(1C-3C)alkyl, (mono- or di(1C-4C)alkyl)aminomethyl, (mono- or di(1C-4C)alkyl)-aminocarbonyl, or a 3-, 4-, 5- or 6-membered monocyclic, homocyclic or, aromatic or non-aromatic ring.

4. The compound according to claim 3, wherein,
$R^3$ is H or halogen;
$R^4$ is H;
$R^5$ is H, OH, (1C-4C)alkoxy, CN, F, Cl, $CF_3$, $NO_2$, hydroxy(1C-4C)alkyl, $CO_2$(1C-6C)alkyl, or
$R^5$ is $NHR^6$, wherein $R^6$ is (1C-3C)acyl optionally substituted with one or more halogens or
$R^5$ is $C(O)N(R^8,R^9)$, wherein $R^8$ and $R^9$ each independently are H, (3C-5C)cycloalkyl, or $CH_2R^{10}$,
wherein $R^{10}$ is H, (1C-5C)alkyl, (1C-5C)alkenyl, hydroxy(1C-3C)alkyl, (1C-2C)alkylester of carboxy(1C-2C)alkyl, (1C-3C)alkoxy(1C-3C)alkyl, (mono- or di(1C-4C)alkyl)aminomethyl, (mono- or di(1C-4C)alkyl)aminocarbonyl, or (3C-5C)cycloalkyl.

5. The compound according to claim 4, wherein,
X is S or $SO_2$;
$R^2$ is 2-nitrophenyl, 2-hydroxymethyl-phenyl, 2-benzamide, 2-methoxyphenyl, or 2-cyanophenyl;
$R^3$ is H or F;
$R^5$ is H, OH, (1C-2C)alkoxy, CN, F, Cl, $CF_3$, $NO_2$, hydroxy(1C-4C)alkyl, $CO_2$(1C-4C)alkyl, or
$R^5$ is $NHR^6$, wherein $R^6$ is formyl, acetyl, fluoroacetyl, difluoroacetyl, or trifluoroacetyl, or
$R^5$ is $C(O)N(R^8,R^9)$, wherein $R^8$ is H, and $R^9$ is H, cyclopropyl or
$R^9$ is $CH_2R^{10}$, wherein $R^{10}$ is H, (1C-2C)alkyl, hydroxy(1C-2C)alkyl, methoxy(1C-2C)alkyl, cyclopropyl.

6. The compound according to claim 5, wherein,
X is S;
$R^1$ is 3,5-difluorophenyl, 3-fluorophenyl, 3-cyanophenyl, or 3-nitrophenyl;
$R^2$ is 2-nitrophenyl, 2-hydroxymethyl-phenyl, 2-methoxyphenyl, or 2-cyanophenyl;
$R^3$ is H;
$R^5$ is OH, (1C-2C)alkoxy, CN, $CF_3$, $NO_2$, hydroxy(1C-4C)alkyl, $CO_2$(1C-4C)alkyl, or $NHR^6$,
wherein $R^6$ is formyl, acetyl, fluoroacetyl, difluoroacetyl, or trifluoroacetyl.

7. The compound according to claim 6, wherein,
$R^1$ is 3,5-difluorophenyl;
$R^2$ is 2-nitrophenyl, or 2-hydroxymethyl-phenyl;
$R^5$ is OH, (1C-2C)alkoxy, CN, hydroxy(1C-4C)alkyl, or $NHR^6$, wherein $R^6$ is formyl, acetyl, fluoroacetyl, difluoroacetyl, or trifluoroacetyl.

8. The compound according to claim 7, wherein,
$R^1$ is 3,5-difluorophenyl;
$R^2$ is 2-nitrophenyl;
$R^5$ is OH, (1C-2C)alkoxy, CN, or $NHR^6$, wherein $R^6$ is formyl, acetyl, fluoroacetyl, difluoroacetyl, or trifluoroacetyl.

9. The compound according to claim 8, which is N-[1-(3,5-Difluoro-benzyl)-3-(2-nitro-phenylsulfanyl)-1H-indol-6-yl]-2-fluoro-acetamide.

10. The compound according to claim 5, wherein,
X is S;
$R^1$ is 3,5-difluorophenyl, 3-fluorophenyl, 3-cyanophenyl, or 3-nitrophenyl;
$R^2$ is 2-nitrophenyl, 2-hydroxymethyl-phenyl, 2-methoxyphenyl, or 2-cyanophenyl;

R³ is H;
R⁵ is C(O)N(R⁸,R⁹), wherein R⁸ is H, and R⁹ is H, or CH₂R¹⁰, wherein R¹⁰ is H, (1C-2C)alkyl, hydroxy(1C-2C)alkyl, or methoxy(1C-2C)alkyl.

11. The compound according to claim 10, wherein,
R¹ is 3,5-difluorophenyl;
R² is 2-nitrophenyl, or 2-hydroxymethyl-phenyl;
R⁵ is C(O)N(R⁸,R⁹), wherein R⁸ is H, and R⁹ is CH₂R¹⁰, wherein R¹⁰ is H, or (1C-2C)alkyl.

12. The compound according to claim 11, which is 1-(3,5-Difluoro-benzyl)-3-(2-nitro-phenylsulfanyl)-1H-indole-6-carboxylic acid methylamide.

13. The compound according to claim 4, wherein,
X is S;
R¹ is 3,5-difluorophenyl, 3-fluorophenyl, 3-cyanophenyl, or 3-nitrophenyl;
R² is 2-nitrophenyl, 2-hydroxymethyl-phenyl, 2-methoxyphenyl, or 2-cyanophenyl;
R³ is H;
R⁵ is C(O)N(R⁸,R⁹), wherein R⁸ and R⁹ each independently are H, or CH₂R¹⁰, wherein R¹⁰ is H, (1C-5C)alkyl, (1C-5C)alkenyl, hydroxy(1C-3C)alkyl, (1C-3C)alkoxy(1C-3C)alkyl, or (mono- or di(1C-4C)alkyl)aminomethyl.

14. The compound according to claim 13, wherein,
R¹ is 3,5-difluorophenyl;
R² is 2-nitrophenyl, or 2-hydroxymethyl-phenyl;
R⁵ is C(O)N(R⁸,R⁹), wherein R⁸ and R⁹ each independently are H, or CH₂R¹⁰, wherein R¹⁰ is H, (1C-5C)alkyl, hydroxy(1C-3C)alkyl, or (1C-3C)alkoxy(1C-3C)alkyl.

15. The compound according to claim 14, which is 1-(3,5-Difluoro-benzyl)-3-(2-nitro-phenylsulfanyl)-1H-indole-6-carboxylic acid dimethylamide.

16. A pharmaceutical composition, comprising:
the compound according to claim 1 or salt thereof and a pharmaceutically acceptable carrier.

17. A method of treating osteoporosis in a subject in need thereof, comprising:
administering to the subject a pharmaceutically effective amount of the compound or salt thereof according to claim 1.

18. A method of treating an androgen insufficiency, comprising:
administering a pharmaceutically effective amount of the compound according to claim 1 or a salt thereof to a subject in need thereof.

* * * * *